United States Patent [19]

Fuller et al.

[11] Patent Number: 5,981,195
[45] Date of Patent: *Nov. 9, 1999

[54] CHIMERIC RECEPTORS AND METHODS FOR IDENTIFYING COMPOUNDS ACTIVE AT METABOTROPIC GLUTAMATE RECEPTORS

[75] Inventors: Forrest H. Fuller, La Jolla, Calif.; Karen J. Krapcho, Salt Lake City; Lance G. Hammerland, Bountiful, both of Utah

[73] Assignee: NPS Pharmaceuticals, Inc., Salt Lake City, Utah

[*] Notice: This patent issued on a continued prosecution application filed under 37 CFR 1.53(d), and is subject to the twenty year patent term provisions of 35 U.S.C. 154(a)(2).

[21] Appl. No.: 08/687,289

[22] Filed: Jul. 25, 1996

Related U.S. Application Data

[60] Provisional application No. 60/001,526, Jul. 26, 1995.
[51] Int. Cl.$^6$ .......................... C07K 19/00; C12N 15/62
[52] U.S. Cl. .......................... 435/7.1; 435/7.2; 435/69.7; 435/252.3; 435/320.1; 530/350; 536/23.4
[58] Field of Search .......................... 435/69.7, 6, 7.1, 435/7.2, 252.3, 32.7; 530/350; 536/23.4

[56] References Cited

U.S. PATENT DOCUMENTS

| | | |
|---|---|---|
| 4,859,609 | 8/1989 | Dull et al. . |
| 4,945,050 | 7/1990 | Sanford ................................ 435/172.1 |
| 5,030,576 | 7/1991 | Dull et al. . |
| 5,688,938 | 11/1997 | Brown et al. .......................... 536/23.5 |

FOREIGN PATENT DOCUMENTS

| | | |
|---|---|---|
| 0568384 | 11/1993 | European Pat. Off. . |
| 0569240 | 11/1993 | European Pat. Off. . |
| 9210583 | 6/1992 | WIPO . |
| 9220642 | 11/1992 | WIPO . |
| 9418959 | 9/1994 | WIPO . |
| 9429449 | 12/1994 | WIPO . |
| 9508627 | 5/1995 | WIPO . |

OTHER PUBLICATIONS

Flor et al., "The C–Terminal Domain of the mGluR1 Metabotropic Glutamate Receptor Affects Sensitivity to Agonists," *Journal of Neurochemistry* 67:58–63 (1996).
Gomeza et al., "The Second Intracellular Loop of Metabotropic Glutamate Receptor 1 Cooperates with the Other Intracellular Domains to Control Coupling to G–proteins," *J. Biol. Chem.* 271(4):2199–2205 (1966).
Hammerland et al., "Mechanism of Action of the Calcimimetic Compounds NPS R–467 and NPS R–568 in Xenopus Oocytes Expressing a Bovine Parathyroid Cell Calcium Receptor," *Journal of Bone and Mineral Research* 8(Supplement 1):S133 at abstract No. 65 (1993).
Tones et al., "The agonist selectivity of a class III metabotropic glutamate receptor, human mGlur4a, is determined by the N–terminal extracellular domain," *NeuroReport* 7:117–120 (1995).
Abe et al., "Molecular Characterization of a Novel Metabotropic Glutamate Receptor mGluR5 Coupled to Inositol Phosphate/Ca$^{2+}$ Signal Transduction," *J. Biol. Chem.* 267:13361–13368 (1992).
Aiba et al., "Reduced Hippocampal Long–Term Potentiation and Context–Specific Deficit in Associative Learning in mGluR1 Mutant Mice," *Cell* 79:365–375 (1994).
Aiba et al., "Deficient Cerebellar Long–Term Depression and Impaired Motor Learning in mGluR1 Mutant Mice," *Cell* 79:377–388 (1994).
Ambrosini et al., "Metabotropic Glutamate Receptors Negatively Coupled to Adenylate Cyclase Inhibit N–Methyl–D–aspartate Receptor Activity and Prevent Neurotoxicity in Mesencephalic Neurons In Vitro," *Mol. Pharmacol.* 47:1057–1064 (1995).
Aramori and Nakanishi, "Signal Transduction and Pharmacological Characteristics of a Metabotropic Glutamate Receptor, mGluR1, in Transfected CHO Cells," *Neuron* 8:757–765 (1992).
Bashir et al., "Induction of LTP in the hippocampus needs synaptic activation of glutamate metabotropic receptors," *Nature* 363:347–350 (1993).
Baskys, "Metabotropic receptors and 'slow' excitatory actions of glutamate agonists in the hippocampus," *Trends in Neurosciences* 15:92–96 (1992).
Birrell et al., "(1S, 3R)–1–Aminocyclopentane–1,3–Dicarboxylic Acid Attenuates N–Methyl–D–Aspartate–Induced Neuronal Cell Death in Cortical Cultures Via A Reduction in Delayed Ca$^{2+}$ Accumulation," *Neuropharmacology* 32(12):1351–1358 (1993).
Bortolotto et al., "A molecular switch activated by metabotropic glutamate receptors regulates induction of long–term potentiation," *Nature* 368:740–743 (1994).
Brinster et al., "Factors affecting the efficiency of introducing foreign DNA into mice by microinjecting eggs," *Proc. Natl. Acad. Sci. USA* 82:4438–4442 (1985).

(List continued on next page.)

*Primary Examiner*—JOhn Ulm
*Attorney, Agent, or Firm*—Lyon & Lyon LLP

[57] ABSTRACT

The present invention provides chimeric receptors. The chimeric receptors comprise at least one region homologous to a region of a metabotropic glutamate receptor and at least one region homologous to a region of a calcium receptor. The invention also includes methods of preparing such chimeric receptors, and methods of using such receptors to identify and characterize compounds which modulate the activity of metabotropic glutamate receptors or calcium receptors. The invention also relates to compounds and methods for modulating metabotropic glutamate receptor activity and binding to metabotropic glutamate receptors. Modulation of metabotropic glutamate receptor activity can be used for different purposes such as treating neurological disorders and diseases, inducing an analgesic effect, cognition enhancement, and inducing a muscle-relaxant effect.

48 Claims, 34 Drawing Sheets

OTHER PUBLICATIONS

Brown, "Cloning and characterization of an extracellular $Ca^{2+}$–sensing receptor from bovine parathyroid," *Nature* 366:575–580 (1993).

Calabresi et al., "Activation of quisqualate metabotropic receptors reduces glutamate and GABA–mediated synaptic potentials in the rat striatum," *Neurosci. Lett.* 139:41–44 (1992).

Capecchi, "Altering the Genome by Homologous Recombination," *Science* 244:1288–1292 (1989).

Cheng and Prusoff, "Relationship Between the Inhibition Constant ($K_1$) and the Concentration of Inhibitor Which Causes 50 Per Cent Inhibition ($I_{50}$) of an Enzymatic Reaction," *Biochemical Pharmacology* 22:3099–3108 (1973).

Chiamulera et al., *Eur. J. Pharmacol.* 216:335 (1992).

Cockcroft et al., "Homologies and Disparities of Glutamate Receptors: A Critical Analysis," *Neurochem. Int.* 23(6):583–594 (1993).

Cotecchia et al., *Proc. Natl. Acad. Sci. USA* 87:2896 (1990).

Cotecchia et al., *J. Biol. Chem.* 267:1633 (1992).

Cunningham et al., "Excitatory Amino Acid Receptors: A Gallery of New Targets For Pharmacological Intervention," *Life Sciences* 54:135–148 (1993).

Duvoisin et al., "A Novel Metabotropic Glutamate Receptor Expressed in the Retina and Olfactory Bulb," *J. Neuroscience* 15:3075–3083 (1995).

Eaton et al., "Competitive antagonism at metabotropic glutamate receptors by (S)–4–carboxyphenylglycine and (RS)–α–methyl–4–carboxyphenylglycine," *European Journal of Pharmacology* 244:195–197 (1993).

Ferguson and Williams, "Cell–Surface Anchoring of Proteins Via Glycosylphosphatidylinositol Structures," *Ann. Rev. Biochem.* 57:285–320 (1988).

Flor et al., *Neuropharmacology* 34:149 (1994).

Flor et al., *Soc. Neurosci. Abst.* 20:468 (1994).

Gabellini et al., "Is the Heterologous Expression of Metabotropic Glutamate Receptors (mGluRs) an Appropriate Method to Study the mGluR Function? Experience With Human Embryonic Kidney 293 Cells Transfected with mGluR1," *Neurochem. Int.* 24:533–539 (1994).

Garrett et al., *J. Biol. Chem.* 210:12919–12925 (1995).

Goldberger and Anfinsen, "The Reversible Masking of Amino Groups in Ribonuclease and Its Possible Usefulness in the Synthesis of the Protein," *Biochemistry* ed. H. Neurath (Easton, PA:Mack Printing Company) 1:401–405 (1962).

Greene et al., "Metabotropic receptor mediated afterdepolarization in neocortical neurons," *Eur. J. Pharmacol.* 226:279–280 (1992).

Gross and Witkop, "Selective Cleavage of the Methionyl Peptide Bonds in Ribonuclease with Cyanogen Bromide," *J. Amer. Chem. Soc.* 83:1510–1511 (1961).

Hammer et al., "Spontaneous Inflammatory Disease in Transgenic Rats Expressing HLA–B27 and Human $\beta_2m$: An Animal Model of HLA–B27–Associated Human Disorders," *Cell* 63:1099–1112 (1990).

Hayashi et al., "Role of a metabotropic glutamate receptor in synaptic modulation in the accessory olfactory bulb," *Nature* 366:687–690 (1993).

Hill, "A New Mathematical Treatment of Changes of Ionic Concentration in Muscle and Nerve Under the Action of Electric Currents, with a Theory as to Their Mode of Excitation," *J. Physiology* 40:190–224 (1910).

Hollmann and Heinemann, "Cloned Glutamate Receptors," *Ann. Rev. Neurosci.* 17:31–108 (1994).

Houdebine and Chourrout, "Transgenesis in Fish," *Experientia* 47:891–897 (1991).

Hu and Storm, "Excitatory amino acids acting on metabotropic glutamate receptors broaden the action potential in hippocampal neurons," *Brain Res.* 568:339–344 (1991).

Ikeda et al., "Heterologous Expression of Metabotropic Glutamate Receptors in Adult Rat Sympathetic Neurons: Subtype–Specific Coupling to Ion Channels," *Neuron* 14:1029–1038 (1995).

Jane et al., *Br. J. Pharmacol.* 112:809 (1994).

Joly et al., "Molecular, Functional, and Pharmacological Characterization of the Metabotropic Glutamate Receptor Type 5 Splice Variants: Comparison with mGluR1," *J. Neuroscience* 15:3970–3981 (1995).

Joyner et al., "Production of a mutation in mouse En–2 gene by homologous recombination in embryonic stem cells," *Nature* 338:153–156 (1989).

Knopfel et al., "Metabotropic Glutamate Receptors: Novel Targets for Drug Development," *J. Med. Chem.* 38:1417–1428 (1995).

Kobilka et al., *Science* 240:1310 (1988).

Koerner and Johnson, "Ch. 14—L–AP4 receptor ligands," *Excitatory Amino Acid Receptors; Design of Agonists and Antagonists* pp. 308–330 (1992).

Koh et al., "Activation of the metabotropic glutamate receptor attenuates N–methyl–D–aspartate neurotoxicity in cortical cultures," *Proc. Natl. Acad. Sci. USA* 88:9431–9435 (1991).

Lechleiter et al., *EMBO J.* 9:4381 (1990).

Liggett et al., *J. Biol. Chem.* 267:4740 (1992).

Lin et al., *Soc. Neurosci. Abstr.* 20:468 (1994).

Lindley, "A New Synthetic Substrate for Trypsin and its Application to the Determination of the Amino–acid Sequence of Proteins," *Nature* 178:647–658 (1956).

Lombardi et al., "Pharmacological characterization of the metabotropic glutamate receptor inhibiting D–[$^3$H]–aspartate output in rat striatum," *Br. J. Pharmacol.* 110:1407–1412 (1993).

Marcus–Sekura and Hitchcock, "Preparation of Oocytes for Microinjection of RNA and DNA," *Methods in Enzymology* 152:284–288 (1987).

Martin et al., "Cellular Localization of a Metabotropic Glutamate Receptor in Rat Brain," *Neuron* 9:259–270 (1992).

Masu et al., "Sequence and expression of a metabotropic glutamate receptor," *Nature* 349:760–765 (1991).

Meller et al., "Acute mechanical hyperalgesia is produced by coactivation of AMPA and metabotropic glutamate receptors," *NeuroReport* 4:879–882 (1993).

Minakami et al., "Molecular Cloning and the Functional Expression of Two Isoforms of Human Metabotropic Glutamate Receptor Subtype 5," *Biochem. Biophys. Res. Commun.* 199:1136–1143 (1994).

Nakajima et al., "Molecular Characterization of a Novel Retinal Metabotropic Glutamate Receptor mGluR6 with a High Agonist Selectively for L–2–Amino–4–phosphonobutyrate," *J. Biol. Chem.* 268:11868–11873 (1993).

Nakanishi, "Molecular Diversity of Glutamate Receptors and Implications for Brain Function," *Science* 258:597–603 (1992).

Nakanishi, "Metabotropic Glutamate Receptors: Synaptic Transmission, Modulation, and Plasticity," *Neuron* 13:1031–1037 (1994).

Namba et al., *Nature* 365:166 (1993).

Negishi et al., *J. Biol. Chem.* 268:9517 (1993).

Nicoletti et al., "Excitatory amino acid recognition sites coupled with inositol phospholipid metabolism: Developmental changes and interaction with $\alpha_1$–adrenoceptors," *Proc. Natl. Acad. Sci. USA* 83:1931–1935 (1986).

O'Hara et al., "The Ligand–Binding Domain in Metabotropic Glutamate Receptors Is Related to Bacterial Periplasmic Binding Proteins," *Neuron* 11:41–52 (1993).

Ohishi et al., "Distribution of the Messenger RNA for a Metabotropic Glutamate Receptor, mGluR2, in the Central Nervous System of the Rat," *Neuroscience* 53:1009–1018 (1993).

Ohishi et al., "Immunohistochemical Localization of Metabotropic Glutamate Receptors, mGluR2 and mGluR3, in Rat Cerebellar Cortex," *Neuron* 13:55–66 (1994).

Okamoto et al., "Molecular Characterization of a New Metabotropic Glutamate Receptor mGluR7 Coupled to Inhibitory Cyclic AMP Signal Transduction," *J. Biol. Chem.* 269:1231–1236 (1994).

Okamoto et al., *Cell* 67:723 (1991).

Opitz and Reymann, "Blockade of metabotropic glutamate receptors protects rat CA1 neurons from hypoxic injury," *NeuroReport* 2:455–457 (1991).

Pin et al., "Alternative splicing generates metabotropic glutamate receptors inducing different patterns of calcium relaease in Xenopus oocytes," *Proc. Natl. Acad. Sci. USA* 89:10331–10335 (1992).

Pin and Duvoisin, "Review: Neurotransmitter receptors I," *Neuropharmacology* 34:1–26 (1995).

Pin et al., *EMBO J.* 13:342 (1992).

Pin et al., *Current Drugs: Neurodegenerative Disorders* 1:111 (1993).

Pizzi et al., "Attenuation of Excitatory Amino Acid Toxicity by Metabotropic Glutamate Receptor Agonists and Aniracetam in Primary Cultures of Cerebellar Granule Cells," *J. Neurochemistry* 61:683–689 (1993).

Pollak et al., "Mutations in the Human $Ca^{2+}$–Sensing Receptor Gene Cause Familial Hypocalciuric Hypercalcemia and Neonatal Severe Hyperparathyroidism," *Cell* 75:1297–1303 (1993).

Pursel et al., "Genetic Engineering of Livestock," *Science* 244:1281–1288 (1989).

Riccardi et al., "Cloning and functional expression of a rat kidney extracellular calcium/polyvalent cation–sensing receptor," *Proc. Natl. Acad. Sci. USA* 92:131–135 (1995).

Sacaan and Schoepp, "Activation of hippocampal metabotropic excitatory amino acid receptors leads to seizures and neuronal damage," *Neuroscience Letters* 139:77–82 (1992).

Saugstad et al., *Mol. Pharmacol.* 45:367 (1994).

Scatchard, "The Attractions of Proteins For Small Molecules and Ions," *Ann. N.Y. Acad. Sci.* 51:660–672 (1949).

Schoepp and Johnson, "Comparision of Excitatory Amino Acid–Stimulated Phosphoinositide Hydrolysis and N–[$^3$H] Acetylaspartylglutamate Binding in Rat Brain: Selective Inhibition of Phosphoinositide Hydrolysis by 2–Amino–3–Phosphonopropionate," *J. Neurochemistry* 53(1):273–278 (1989).

Schoepp and Conn, "Metabotropic glutamate receptors in brain function and pathology," *TIPS* 14:13–20 (1993).

Schoepp, "Novel Functions for Subtypes of Metabotropic Glutamate Receptors," *Neurochem. Int.* 24:439–449 (1994).

Schoepp et al., "Pharmacological and functional characteristics of metabotropic excitatory amino acid receptors," *TIPS* 11:508–515 (1990).

Sgimoto et al., *J. Biol. Chem.* 268:2712 (1993).

Sheardown, "Metabotropic glutamate receptor agonists reduce epileptiform activity in the rat cortex," *NeuroReport* 3:916–918 (1992).

Shigemoto et al., "Antibodies Inactivating mGluR1 Metabotropic Glutamate Receptor Block Long–Term Depression in Cultured Purkinje Cells," *Neuron* 12:1245–1255 (1994).

Siliprandi et al., "Activation of the glutamate metabotropic receptor protects retina against N–methyl–D–aspartate toxicity," *European Journal of Pharmacology* 219:173–174 (1992).

Takahashi et al., "Role of the Large Exracellular Domain of Metabtropic Glutamate Receptors in Agonist Selectively Determination," *J. Biol. Chem.* 268:19341–19345 (1993).

Tanabe et al., "Signal Transduction, Pharmacological Properties, and Expression Patterns of Two Rat Metabotropic Glutamate Receptors, mGluR3 and mGluR4," *J. Neuroscience* 13:1372–1378 (1993).

Tanabe et al., "A Family of Metabotropic Glutamate Receptors," *Neuron* 8:169–179 (1992).

Taschenberger and Lowe, "Effects of a metabotropic glutamate agonist, trans–ACPD, on cortical epileptiform activity," *NeuroReport* 3:629–632 (1992).

Thomsen et al., "(S)–4–Carboxy–3–Hydroxyphenylglycine, and Antagonist of Metabotropic Glutamate Receptor (mGluR)1a and an Agonist of mGlurR2, Protects Against Audiogenic Seizures in DBA/2 Mice," *J. Neurochem.* 62:2492–2495 (1995).

Thomsen et al., *Eur. J. Pharmacol.* 227:361 (1992).

Thomsen et al., *Brain Res.* 619:22 (1992).

Titeler, *Multiple Dopamine Receptors: Receptor Binding Studies in Dopamine Pharmacology*, Marcel Dekker, Inc., New York, pp. 1–173 (1983).

Trombley and Westbrook, "L–AP4 Inhibits Calcium Currents and Synaptic Transmission via a G–Protein–coupled Glutamate Receptor," *J. Neuroscience* 12:2043–2050 (1992).

Wang et al., *J. Biol. Chem.* 270:16677 (1995).

Watkins and Collingridge, "Phenylglycine derivatives as antagonists of metabotropic glutamate receptors," *Trends Pharmacol Sci.* 15:333–342 (1994).

Wess et al., *Mol. Pharmacol.* 38:517 (1990).

Wess et al., *FEBS Letters* 258:133 (1989).

Williams et al., "Effects of Polyamines on the Binding of [$^3$H]MK–801 to the N–Methyl–D–Aspartate Receptor: Pharmacological Evidence for the Existence of a Polyamine Recognition Site," *Molec. Pharmacol.* 36:575–581 (1989).

Witkop, "Nonenzymatic Methods for the Preferential and Selective Cleavage and Modification of Proteins," *Advances in Protein Chemistry* eds. C.B. Anfinsen, K. Bailey, M.L. Anson, J.T. Edsall (New York:Academic Press) 16:221–321 (1961).

Wong et al., *J. Biol. Chem.* 265:6219 (1990).

Zheng and Gallagher, "Trans–ACPD (trans–D, L–1–amino–1,3–cyclopentanedicarboxylic acid) elicited oscillation of membrane potentials in rat dorsolateral septal nucleus neurons recorded intracellulary in vitro," *Neuroscience Letters* 125:147–150 (1991).

Hammerland et al.: "Functional Analysis of Chimeras Constructed from Metabotropic Glutamate and Calcium Receptors", $25^{th}$ Annual Meeting of the Society for Neuroscience, vol. 21, No. 1–3, Nov. 11–16, 1995, San Diego, California, USA, p. 844 XP000610222.

Strader et al.: "Structure and Function of G Protein—Coupled Receptors", Annu. Rev. Biochem. 1994, 63:101–32.

Huang, et al.: Localization of the Ligand Binding Site of the Neurokinin–1 Receptor: Interpretation of Chimeric Mutations and Single–Residue Substitutions, Molecular Pharmacology, 45:690–695, 1994.

Moyle et al.: Leutropin/β–Adrenergic Receptor Chimeras Bind Choriogonadotropin and Adrenergic Ligands but are not Expressed at the Cell Surface, The Journal of Biological Chemsitry, vol. 266, No. 17, Issue of Jun. 15, pp. 10807–10812, 1991.

a) mGluR b) CaR c) mGluR/CaR
(mGluR$_{ex}$/CaR)

d) CaR/mGluR
(CaR$_{ex}$/mGluR)

e) CH3
(mGluR/CaR$_{in}$)

f) CH3-2*
(mGluR/CaR$_{in}$)

Fig. 2A

```
Sequence Range: -7 to 3379
              3             13            23            33
         *    *    *   *    *    *   *    *    *    *
    CGCCACA ATG GTC CGG CTC CTC TTG ATT TTC TTC CCA ATG ATC TTT TTG
            Met Val Arg Leu Leu Leu Ile Phe Phe Pro Met Ile Phe Leu>
              b   CODING SEQUENCE CHIMERA:JUNCTION NUC.1776      b   >
        a     a   a    -8 TO 1775 OF MCRATMGL-1    30   a    a   a40 >

43           53            63            73            83
     *    *    *    *    *    *    *    *    *    *
    GAG ATG TCC ATT TTG CCC AGG ATG CCT GAC AGA AAA GTA TTG CTG GCA
    Glu Met Ser Ile Leu Pro Arg Met Pro Asp Arg Lys Val Leu Leu Ala>
     b   b   CODING SEQUENCE CHIMERA:JUNCTION NUC.1776    b   b    >
     a   a  50a   a    -8 TO 1775 OF MCRATMGL-1    a  80a   a   a    >

93           103           113           123           133
     *    *    *    *    *    *    *    *    *    *
    GGT GCC TCG TCC CAG CGC TCC GTG GCG AGA ATG GAC GGA GAT GTC ATC
    Gly Ala Ser Ser Gln Arg Ser Val Ala Arg Met Asp Gly Asp Val Ile>
     b   b   CODING SEQUENCE CHIMERA:JUNCTION NUC.1776    b   b    >
    90   a   a   100  a    -8 TO 1775 OF MCRATMGL-1 a   a   130 a   a   >

143          153           163           173           183
     *    *    *    *    *    *    *    *    *    *
    ATC GGA GCC CTC TTC TCA GTC CAT CAC CAG CCT CCA GCC GAG AAG GTA
    Ile Gly Ala Leu Phe Ser Val His His Gln Pro Pro Ala Glu Lys Val>
     b   b   CODING SEQUENCE CHIMERA:JUNCTION NUC.1776    b   b    >
    140a  a   a   150  -8 TO 1775 OF MCRATMGL-1    a    a   180  a    >

193          203           213           223           233
     *    *    *    *    *    *    *    *    *    *
    CCC GAA AGG AAG TGT GGG GAG ATC AGG GAA CAG TAT GGT ATC CAG AGG
    Pro Glu Arg Lys Cys Gly Glu Ile Arg Glu Gln Tyr Gly Ile Gln Arg>
     b   b   CODING SEQUENCE CHIMERA:JUNCTION NUC.1776    b   b    >
    190  a   a   a20 -8 TO 1775 OF MCRATMGL-1 20  a    a   a230a    >

243           253           263           273
         *    *    *    *    *    *    *    *    *    *
    GTG GAG GCC ATG TTC CAC ACG TTG GAT AAG ATT AAC GCG GAC CCG GTG
    Val Glu Ala Met Phe His Thr Leu Asp Lys Ile Asn Ala Asp Pro Val>
         b   b   CODING SEQUENCE CHIMERA:JUNCTION NUC.1776    b   b   >
     a  240  a   a    -8 TO 1775 OF MCRATMGL-1   270  a   a   280  >

283          293          303          313          323
     *    *    *    *    *    *    *    *    *    *
    CTC CTG CCC AAC ATC ACT CTG GGC AGT GAG ATC CGG GAC TCC TGC TGG
    Leu Leu Pro Asn Ile Thr Leu Gly Ser Glu Ile Arg Asp Ser Cys Trp>
     b   b   CODING SEQUENCE CHIMERA:JUNCTION NUC.1776    b   b    >
     a  a290a   a    -8 TO 1775 OF MCRATMGL-1    a320a   a    a    >

333          343          353          363          373
     *    *    *    *    *    *    *    *    *    *
    CAC TCT TCA GTG GCT CTC GAA CAG AGC ATC GAA TTC ATC AGA GAC TCC
    His Ser Ser Val Ala Leu Glu Gln Ser Ile Glu Phe Ile Arg Asp Ser>
     b   b   CODING SEQUENCE CHIMERA:JUNCTION NUC.1776    b   b    >
    330  a   a   340  a    -8 TO 1775 OF MCRATMGL-1 a    a   370 a   a  >

383          393          403          413          423
     *    *    *    *    *    *    *    *    *    *
    CTG ATT TCC ATC CGA GAT GAG AAG GAT GGG CTG AAC CGA TGC CTG CCT
    Leu Ile Ser Ile Arg Asp Glu Lys Asp Gly Leu Asn Arg Cys Leu Pro>
```

Fig. 2B

```
            b     b    CODING SEQUENCE CHIMERA:JUNCTION NUC.1776      b    b    >
        380a    a    a    390  -8 TO 1775 OF MCRATMGL-1    a    a   420   a    >

433           443           453           463           473
               *     *      *      *      *     *       *      *      *      *
         GAT GGC CAG ACC CTG CCC CCT GGC AGG ACT AAG AAG CCT ATT GCT GGA
         Asp Gly Gln Thr Leu Pro Pro Gly Arg Thr Lys Lys Pro Ile Ala Gly>
              b     b    CODING SEQUENCE CHIMERA:JUNCTION NUC.1776      b    b    >
            430 a   a    a44  -8 TO 1775 OF MCRATMGL-1 60  a    a    a470a    >

483           493           503           513
               *     *      *      *      *     *       *      *      *
         GTG ATC GGC CCT GGC TCC AGC TCT GTG GCC ATT CAA GTC CAG AAT CTT
         Val Ile Gly Pro Gly Ser Ser Ser Val Ala Ile Gln Val Gln Asn Leu>
              b     b    CODING SEQUENCE CHIMERA:JUNCTION NUC.1776      b    b    >
           a  480   a    a    -8 TO 1775 OF MCRATMGL-1   510  a    a    520   >

523           533           543           553           563
    *     *      *      *      *     *       *      *      *      *
    CTC CAG CTG TTC GAC ATC CCA CAG ATC GCC TAT TCT GCC ACA AGC ATA
    Leu Gln Leu Phe Asp Ile Pro Gln Ile Ala Tyr Ser Ala Thr Ser Ile>
         b     b    CODING SEQUENCE CHIMERA:JUNCTION NUC.1776      b    b    >
       a  a530a   a    -8 TO 1775 OF MCRATMGL-1    a560a   a    a    >

573           583           593           603           613
     *     *      *      *      *     *       *      *      *      *
     GAC CTG AGT GAC AAA ACT TTG TAC AAA TAC TTC CTG AGG GTG GTC CCT
     Asp Leu Ser Asp Lys Thr Leu Tyr Lys Tyr Phe Leu Arg Val Val Pro>
          b     b    CODING SEQUENCE CHIMERA:JUNCTION NUC.1776      b    b    >
      570  a    a   580  a    -8 TO 1775 OF MCRATMGL-1 a    a   610  a    a    >

623           633           643           653           663
     *     *      *      *      *     *       *      *      *
     TCT GAC ACT TTG CAG GCA AGG GCG ATG CTC GAC ATA GTC AAG CGT TAC
     Ser Asp Thr Leu Gln Ala Arg Ala Met Leu Asp Ile Val Lys Arg Tyr>
          b     b    CODING SEQUENCE CHIMERA:JUNCTION NUC.1776      b    b    >
      620a   a    a   630   -8 TO 1775 OF MCRATMGL-1   a    a   660  a    >

673           683           693           703           713
               *     *      *      *      *     *       *      *      *      *
         AAC TGG ACC TAT GTC TCA GCA GTC CAC ACA GAA GGG AAT TAC GGC GAG
         Asn Trp Thr Tyr Val Ser Ala Val His Thr Glu Gly Asn Tyr Gly Glu>
              b     b    CODING SEQUENCE CHIMERA:JUNCTION NUC.1776      b    b    >
            670 a   a    a68  -8 TO 1775 OF MCRATMGL-1 00  a    a    a710a    >

723           733           743           753
               *     *      *      *      *     *       *      *      *
         AGT GGA ATG GAT GCT TTC AAA GAA CTG GCT GCC CAG GAA GGC CTC TGC
         Ser Gly Met Asp Ala Phe Lys Glu Leu Ala Ala Gln Glu Gly Leu Cys>
              b     b    CODING SEQUENCE CHIMERA:JUNCTION NUC.1776      b    b    >
            a 720    a    a    -8 TO 1775 OF MCRATMGL-1   750  a    a   760    >

763           773           783           793           803
    *     *      *      *      *     *       *      *      *      *
    ATC GCA CAC TCG GAC AAA ATC TAC AGC AAT GCT GGC GAG AAG AGC TTT
    Ile Ala His Ser Asp Lys Ile Tyr Ser Asn Ala Gly Glu Lys Ser Phe>
         b     b    CODING SEQUENCE CHIMERA:JUNCTION NUC.1776      b    b    >
       a  a770a   a    -8 TO 1775 OF MCRATMGL-1    a800a   a    a    >

813           823           833           843           853
     *     *      *      *      *     *       *      *      *      *
         GAC CGG CTC CTG CGT AAA CTC CGG GAG CGG CTT CCC AAG GCC AGG GTT
```

Fig. 2C

```
              Asp Arg Leu Leu Arg Lys Leu Arg Glu Arg Leu Pro Lys Ala Arg Val>
                 b    b    CODING SEQUENCE CHIMERA:JUNCTION NUC.1776    b    b    >
             810  a    a    820  a   -8 TO 1775 OF MCRATMGL-1 a    a    850  a    a    >

863          873          883          893          903
               *    *    *    *    *    *    *    *    *    *
              GTG GTC TGC TTC TGC GAG GGC ATG ACA GTG CGG GGC TTA CTG AGT GCC
              Val Val Cys Phe Cys Glu Gly Met Thr Val Arg Gly Leu Leu Ser Ala>
                 b    b    CODING SEQUENCE CHIMERA:JUNCTION NUC.1776    b    b    >
             860a  a    a   870  -8 TO 1775 OF MCRATMGL-1 a    a    900  a    >

913          923          933          943          953
                   *    *    *    *    *    *    *    *    *    *
              ATG CGC CGC CTG GGC GTC GTG GGC GAG TTC TCA CTC ATT GGA AGT GAT
              Met Arg Arg Leu Gly Val Val Gly Glu Phe Ser Leu Ile Gly Ser Asp>
                 b    b    CODING SEQUENCE CHIMERA:JUNCTION NUC.1776    b    b    >
              910 a    a    a92  -8 TO 1775 OF MCRATMGL-1 40  a    a    a950a    >

963          973          983          993
                       *    *    *    *    *    *    *    *    *
              GGA TGG GCA GAC AGA GAT GAA GTC ATC GAA GGC TAT GAG GTG GAA GCC
              Gly Trp Ala Asp Arg Asp Glu Val Ile Glu Gly Tyr Glu Val Glu Ala>
                 b    b    CODING SEQUENCE CHIMERA:JUNCTION NUC.1776    b    b    >
               a   960  a    a   -8 TO 1775 OF MCRATMGL-1  990  a    a   1000 >

1003         1013         1023         1033         1043
           *    *    *    *    *    *    *    *    *    *
              AAC GGA GGG ATC ACA ATA AAG CTT CAG TCT CCA GAG GTC AGG TCA TTT
              Asn Gly Gly Ile Thr Ile Lys Leu Gln Ser Pro Glu Val Arg Ser Phe>
                 b    b    CODING SEQUENCE CHIMERA:JUNCTION NUC.1776    b    b    >
               a    1010a   a    -8 TO 1775 OF MCRATMGL-1   1040a    a    a    >

1053         1063         1073         1083         1093
           *    *    *    *    *    *    *    *    *    *
              GAT GAC TAC TTC CTG AAG CTG AGG CTG GAC ACC AAC ACA AGG AAT CCT
              Asp Asp Tyr Phe Leu Lys Leu Arg Leu Asp Thr Asn Thr Arg Asn Pro>
                 b    b    CODING SEQUENCE CHIMERA:JUNCTION NUC.1776    b    b    >
             1050 a    a   1060 a -8 TO 1775 OF MCRATMGL-1 a    a   1090 a    a    >

1103         1113         1123         1133         1143
                   *    *    *    *    *    *    *    *    *
              TGG TTC CCT GAG TTC TGG CAA CAT CGC TTC CAG TGT CGC CTA CCT GGA
              Trp Phe Pro Glu Phe Trp Gln His Arg Phe Gln Cys Arg Leu Pro Gly>
                 b    b    CODING SEQUENCE CHIMERA:JUNCTION NUC.1776    b    b    >
             1100a    a    a 1110 -8 TO 1775 OF MCRATMGL-1 a    a    a 1140 a    >

1153         1163         1173         1183         1193
                   *    *    *    *    *    *    *    *    *    *
              CAC CTC TTG GAA AAC CCC AAC TTT AAG AAA GTG TGC ACA GGA AAT GAA
              His Leu Leu Glu Asn Pro Asn Phe Lys Lys Val Cys Thr Gly Asn Glu>
                 b    b    CODING SEQUENCE CHIMERA:JUNCTION NUC.1776    b    b    >
             1150 a    a    116  -8 TO 1775 OF MCRATMGL-1 80  a    a    1190a    >

1203         1213         1223         1233
                      *    *    *    *    *    *    *    *    *
              AGC TTG GAA GAA AAC TAT GTC CAG GAC AGC AAA ATG GGA TTT GTC ATC
              Ser Leu Glu Glu Asn Tyr Val Gln Asp Ser Lys Met Gly Phe Val Ile>
                 b    b    CODING SEQUENCE CHIMERA:JUNCTION NUC.1776    b    b    >
               a 1200   a    a    -8 TO 1775 OF MCRATMGL-1 1230 a    a   1240 >

```
            AAT GCC ATC TAT GCC ATG GCA CAT GGG CTG CAG AAC ATG CAC CAT GCT
            Asn Ala Ile Tyr Ala Met Ala His Gly Leu Gln Asn Met His His Ala>
               b    b   CODING SEQUENCE CHIMERA:JUNCTION NUC.1776     b    b    >
               a   1250a    a    -8 TO 1775 OF MCRATMGL-1    1280a    a    a    >

1293          1303          1313          1323          1333
        *    *    *    *    *    *    *    *    *    *
      CTG TGT CCC GGC CAT GTG GGC CTG TGT GAT GCT ATG AAA CCC ATT GAT
      Leu Cys Pro Gly His Val Gly Leu Cys Asp Ala Met Lys Pro Ile Asp>
         b    b   CODING SEQUENCE CHIMERA:JUNCTION NUC.1776     b    b    >
      1290 a    a   1300 a -8 TO 1775 OF MCRATMGL-1   a    a   1330 a    a    >

1343          1353          1363          1373          1383
              *    *    *    *    *    *    *    *    *    *
            GGC AGG AAG CTC CTG GAT TTC CTC ATC AAA TCC TCT TTT GTC GGA GTG
            Gly Arg Lys Leu Leu Asp Phe Leu Ile Lys Ser Ser Phe Val Gly Val>
               b    b   CODING SEQUENCE CHIMERA:JUNCTION NUC.1776     b    b    >
            1340a    a    a 1350 -8 TO 1775 OF MCRATMGL-1 a    a    a 1380    a    >

1393          1403          1413          1423          1433
                    *    *    *    *    *    *    *    *    *    *
                  TCT GGA GAG GAG GTG TGG TTC GAT GAG AAG GGG GAT GCT CCC GGA AGG
                  Ser Gly Glu Glu Val Trp Phe Asp Glu Lys Gly Asp Ala Pro Gly Arg>
                     b    b   CODING SEQUENCE CHIMERA:JUNCTION NUC.1776     b    b    >
                  1390 a    a    140 -8 TO 1775 OF MCRATMGL-1 20 a    a    1430a    >

1443          1453          1463          1473
              *    *    *    *    *    *    *    *    *
            TAT GAC ATT ATG AAT CTG CAG TAC ACA GAA GCT AAT CGC TAT GAC TAT
            Tyr Asp Ile Met Asn Leu Gln Tyr Thr Glu Ala Asn Arg Tyr Asp Tyr>
               b    b   CODING SEQUENCE CHIMERA:JUNCTION NUC.1776     b    b    >
             a 1440    a    a    -8 TO 1775 OF MCRATMGL-1 1470    a    a 1480    >

1483          1493          1503          1513          1523
  *    *    *    *    *    *    *    *    *    *
GTC CAC GTG GGG ACC TGG CAT GAA GGA GTG CTG AAT ATT GAT GAT TAC
Val His Val Gly Thr Trp His Glu Gly Val Leu Asn Ile Asp Asp Tyr>
   b    b   CODING SEQUENCE CHIMERA:JUNCTION NUC.1776     b    b    >
   a   1490a    a    -8 TO 1775 OF MCRATMGL-1   1520a    a    a    >

1533          1543          1553          1563          1573
  *    *    *    *    *    *    *    *    *    *
AAA ATC CAG ATG AAC AAA AGC GGA ATG GTA CGA TCT GTG TGC AGT GAG
Lys Ile Gln Met Asn Lys Ser Gly Met Val Arg Ser Val Cys Ser Glu>
   b    b   CODING SEQUENCE CHIMERA:JUNCTION NUC.1776     b    b    >
1530 a    a   1540 a -8 TO 1775 OF MCRATMGL-1 a    a   1570 a    a    >

1583          1593          1603          1613          1623
        *    *    *    *    *    *    *    *    *    *
      CCT TGC TTA AAG GGT CAG ATT AAG GTC ATA CGG AAA GGA GAA GTG AGC
      Pro Cys Leu Lys Gly Gln Ile Lys Val Ile Arg Lys Gly Glu Val Ser>
         b    b   CODING SEQUENCE CHIMERA:JUNCTION NUC.1776     b    b    >
      1580a    a    a 1590 -8 TO 1775 OF MCRATMGL-1 a    a    a 1620    a    >

1633          1643          1653          1663          1673
              *    *    *    *    *    *    *    *    *    *
            TGC TGC TGG ATC TGC ACG GCC TGC AAA GAG AAT GAG TTT GTG CAG GAC
            Cys Cys Trp Ile Cys Thr Ala Cys Lys Glu Asn Glu Phe Val Gln Asp>
               b    b   CODING SEQUENCE CHIMERA:JUNCTION NUC.1776     b    b    >
            1630 a    a    164 -8 TO 1775 OF MCRATMGL-1 60 a    a    1670a    >

```
          *         *         *         *         *         *         *         *         *         *
      GAG TTC ACC TGC AGA GCC TGT GAC CTG GGG TGG TGG CCC AAC GCA GAG
      Glu Phe Thr Cys Arg Ala Cys Asp Leu Gly Trp Trp Pro Asn Ala Glu>
         b    b  CODING SEQUENCE CHIMERA:JUNCTION NUC.1776    b    b   >
         a 1680    a    a   -8 TO 1775 OF MCRATMGL-1  1710    a    a  1720 >

1723           1733          1743          1753          1763
   *       *       *       *       *       *       *       *       *       *
      CTC ACA GGC TGT GAG CCC ATT CCT GTC CGT TAT CTT GAG TGG AGT GAC
      Leu Thr Gly Cys Glu Pro Ile Pro Val Arg Tyr Leu Glu Trp Ser Asp>
         b    b  CODING SEQUENCE CHIMERA:JUNCTION NUC.1776    b    b   >
         a  1730a    a   -8 TO 1775 OF MCRATMGL-1    1760a    a    a   >

1773          1783           1793          1803         1813
   *      *       *       *       *       *       *       *       *       *
      ATA GAA GGG ATC GCA CTC ACC CTC TTT GCC GTG CTG GGC ATT TTC CTG
      Ile Glu Gly Ile Ala Leu Thr Leu Phe Ala Val Leu Gly Ile Phe Leu>
         b    b  CODING SEQUENCE CHIMERA:JUNCTION NUC.1776    b    b   >
1770    a    >
                1840   c  1837 TO 3437 OF MCPHUPCAR4.0 FINAL   c    c   >

1823           1833          1843          1853          1863
   *       *       *       *       *       *       *       *       *       *
      ACA GCC TTT GTG CTG GGT GTG TTT ATC AAG TTC CGC AAC ACA CCC ATT
      Thr Ala Phe Val Leu Gly Val Phe Ile Lys Phe Arg Asn Thr Pro Ile>
         b    b  CODING SEQUENCE CHIMERA:JUNCTION NUC.1776    b    b   >
1880 c    c   1 1837 TO 3437 OF MCPHUPCAR4.0 FINAL   1920c    c   >

1873          1883          1893          1903          1913
        *       *       *       *       *       *       *       *       *       *
      GTC AAG GCC ACC AAC CGA GAG CTC TCC TAC CTC CTC CTC TTC TCC CTG
      Val Lys Ala Thr Asn Arg Glu Leu Ser Tyr Leu Leu Leu Phe Ser Leu>
         b    b  CODING SEQUENCE CHIMERA:JUNCTION NUC.1776    b    b   >
      1930   c    c  1837 TO 3437 OF MCPHUPCAR4.0 FINAL  c   1970  c  >

1923          1933          1943         1953
        *       *       *       *       *       *       *       *       *
      CTC TGC TGC TTC TCC AGC TCC CTG TTC TTC ATC GGG GAG CCC CAG GAC
      Leu Cys Cys Phe Ser Ser Ser Leu Phe Phe Ile Gly Glu Pro Gln Asp>
         b    b  CODING SEQUENCE CHIMERA:JUNCTION NUC.1776    b    b   >
      1980c    c  1837 TO 3437 OF MCPHUPCAR4.0 FINAL   c    c 2020  >

1963          1973          1983          1993          2003
   *      *       *       *       *       *       *       *       *       *
      TGG ACG TGC CGC CTG CGC CAG CCG GCC TTT GGC ATC AGC TTC GTG CTC
      Trp Thr Cys Arg Leu Arg Gln Pro Ala Phe Gly Ile Ser Phe Val Leu>
         b    b  CODING SEQUENCE CHIMERA:JUNCTION NUC.1776    b    b   >
         c  2030  c  1837 TO 3437 OF MCPHUPCAR4.0 FINAL 0  c    c   2070>

2013          2023          2033          2043          2053
   *      *       *       *       *       *       *       *       *       *
      TGC ATC TCA TGC ATC CTG GTG AAA ACC AAC CGT GTC CTC CTG GTG TTT
      Cys Ile Ser Cys Ile Leu Val Lys Thr Asn Arg Val Leu Leu Val Phe>
         b    b  CODING SEQUENCE CHIMERA:JUNCTION NUC.1776    b    b   >
         c    c 2080 1837 TO 3437 OF MCPHUPCAR4.0 FINAL 2110   c    c   >

2063          2073          2083          2093          2103
        *       *       *       *       *       *       *       *       *
      GAG GCC AAG ATC CCC ACC AGC TTC CAC CGC AAG TGG TGG GGG CTC AAC
      Glu Ala Lys Ile Pro Thr Ser Phe His Arg Lys Trp Trp Gly Leu Asn>
         b    b  CODING SEQUENCE CHIMERA:JUNCTION NUC.1776    b    b   >
      2120 c    c   2 1837 TO 3437 OF MCPHUPCAR4.0 FINAL    2160c    c   >
```

Fig. 2F

```
            2113          2123          2133          2143          2153
     *   *   *   *   *   *   *   *   *   *
     CTG CAG TTC CTG CTG GTT TTC CTC TGC ACC TTC ATG CAG ATT GTC ATC
     Leu Gln Phe Leu Leu Val Phe Leu Cys Thr Phe Met Gln Ile Val Ile>
         b   b   CODING SEQUENCE CHIMERA:JUNCTION NUC.1776    b   b   >
     2170  c   c   1837 TO 3437 OF MCPHUPCAR4.0 FINAL     c  2210 c   >

2163          2173          2183          2193
     *   *   *   *   *   *   *   *   *   *
     TGT GTG ATC TGG CTC TAC ACC GCG CCC CCC TCA AGC TAC CGC AAC CAG
     Cys Val Ile Trp Leu Tyr Thr Ala Pro Pro Ser Ser Tyr Arg Asn Gln>
         b   b   CODING SEQUENCE CHIMERA:JUNCTION NUC.1776    b   b   >
       2220c   c   1837 TO 3437 OF MCPHUPCAR4.0 FINAL     c   c  2260 >

2203          2213          2223          2233          2243
     *   *   *   *   *   *   *   *   *   *
     GAG CTG GAG GAT GAG ATC ATC TTC ATC ACG TGC CAC GAG GGC TCC CTC
     Glu Leu Glu Asp Glu Ile Ile Phe Ile Thr Cys His Glu Gly Ser Leu>
         b   b   CODING SEQUENCE CHIMERA:JUNCTION NUC.1776    b   b   >
       c  2270 c   1837 TO 3437 OF MCPHUPCAR4.0 FINAL 0 c   c    2310>

2253          2263          2273          2283          2293
     *   *   *   *   *   *   *   *   *   *
     ATG GCC CTG GGC TTC CTG ATC GGC TAC ACC TGC CTG CTG GCT GCC ATC
     Met Ala Leu Gly Phe Leu Ile Gly Tyr Thr Cys Leu Leu Ala Ala Ile>
         b   b   CODING SEQUENCE CHIMERA:JUNCTION NUC.1776    b   b   >
         c   c  2320 1837 TO 3437 OF MCPHUPCAR4.0 FINAL 2350 c   c   >

2303          2313          2323          2333          2343
     *   *   *   *   *   *   *   *   *
     TGC TTC TTC TTT GCC TTC AAG TCC CGG AAG CTG CCG GAG AAC TTC AAT
     Cys Phe Phe Phe Ala Phe Lys Ser Arg Lys Leu Pro Glu Asn Phe Asn>
         b   b   CODING SEQUENCE CHIMERA:JUNCTION NUC.1776    b   b   >
     2360 c   c    2 1837 TO 3437 OF MCPHUPCAR4.0 FINAL    2400c   c   >

2353          2363          2373          2383          2393
     *   *   *   *   *   *   *   *   *   *
     GAA GCC AAG TTC ATC ACC TTC AGC ATG CTC ATC TTC TTC ATC GTC TGG
     Glu Ala Lys Phe Ile Thr Phe Ser Met Leu Ile Phe Phe Ile Val Trp>
         b   b   CODING SEQUENCE CHIMERA:JUNCTION NUC.1776    b  .b   >
     2410  c   c   1837 TO 3437 OF MCPHUPCAR4.0 FINAL     c  2450 c   >

2403          2413          2423          2433
     *   *   *   *   *   *   *   *   *
     ATC TCC TTC ATT CCA GCC TAT GCC AGC ACC TAT GGC AAG TTT GTC TCT
     Ile Ser Phe Ile Pro Ala Tyr Ala Ser Thr Tyr Gly Lys Phe Val Ser>
         b   b   CODING SEQUENCE CHIMERA:JUNCTION NUC.1776    b   b   >
       2460c   c   1837 TO 3437 OF MCPHUPCAR4.0 FINAL     c   c  2500 >

2443          2453          2463          2473          2483
     *   *   *   *   *   *   *   *   *   *
     GCC GTA GAG GTG ATT GCC ATC CTG GCA GCC AGC TTT GGC TTG CTG GCG
     Ala Val Glu Val Ile Ala Ile Leu Ala Ala Ser Phe Gly Leu Leu Ala>
         b   b   CODING SEQUENCE CHIMERA:JUNCTION NUC.1776    b   b   >
         c  2510 c   1837 TO 3437 OF MCPHUPCAR4.0 FINAL 0 c   c    2550>

2493          2503          2513          2523          2533
     *   *   *   *   *   *   *   *   *   *
     TGC ATC TTC TTC AAC AAG ATC TAC ATC ATT CTC TTC AAG CCA TCC CGC
     Cys Ile Phe Phe Asn Lys Ile Tyr Ile Ile Leu Phe Lys Pro Ser Arg>
         b   b   CODING SEQUENCE CHIMERA:JUNCTION NUC.1776    b   b   >
```

Fig. 2G

```
        c    c 2560 1837 TO 3437 OF MCPHUPCAR4.0 FINAL 2590     c      c    >
     2543         2553         2563         2573         2583
       *     *     *     *     *     *     *     *     *
     AAC ACC ATC GAG GAG GTG CGT TGC AGC ACC GCA GCT CAC GCT TTC AAG
     Asn Thr Ile Glu Glu Val Arg Cys Ser Thr Ala Ala His Ala Phe Lys>
         b     b  CODING SEQUENCE CHIMERA:JUNCTION NUC.1776    b     b     >
  2600 c     c    2 1837 TO 3437 OF MCPHUPCAR4.0 FINAL       2640c    c    >

2593         2603         2613         2623         2633
            *     *     *     *     *     *     *     *     *     *
          GTG GCT GCC CGG GCC ACG CTG CGC CGC AGC AAC GTC TCC CGC AAG CGG
          Val Ala Ala Arg Ala Thr Leu Arg Arg Ser Asn Val Ser Arg Lys Arg>
              b     b  CODING SEQUENCE CHIMERA:JUNCTION NUC.1776    b     b     >
           2650      c     c 1837 TO 3437 OF MCPHUPCAR4.0 FINAL     c  2690 c   >

2643         2653         2663         2673
                 *     *     *     *     *     *     *     *     *
               TCC AGC AGC CTT GGA GGC TCC ACG GGA TCC ACC CCC TCC TCC TCC ATC
               Ser Ser Ser Leu Gly Gly Ser Thr Gly Ser Thr Pro Ser Ser Ser Ile>
                   b     b  CODING SEQUENCE CHIMERA:JUNCTION NUC.1776    b     b     >
                 2700c   c 1837 TO 3437 OF MCPHUPCAR4.0 FINAL    c    c 2740   >

2683         2693         2703         2713         2723
    *     *     *     *     *     *     *     *     *     *
  AGC AGC AAG AGC AAC AGC GAA GAC CCA TTC CCA CAG CCC GAG AGG CAG
  Ser Ser Lys Ser Asn Ser Glu Asp Pro Phe Pro Gln Pro Glu Arg Gln>
      b     b  CODING SEQUENCE CHIMERA:JUNCTION NUC.1776    b     b     >
       c  2750 c  1837 TO 3437 OF MCPHUPCAR4.0 FINAL 0 c    c   2790>

2733         2743         2753         2763         2773
       *     *     *     *     *     *     *     *     *     *
     AAG CAG CAG CAG CCG CTG GCC CTA ACC CAG CAA GAG CAG CAG CAG CAG
     Lys Gln Gln Gln Pro Leu Ala Leu Thr Gln Gln Glu Gln Gln Gln Gln>
         b     b  CODING SEQUENCE CHIMERA:JUNCTION NUC.1776    b     b     >
          c     c 2800 1837 TO 3437 OF MCPHUPCAR4.0 FINAL 2830    c     c    >

2783         2793         2803         2813         2823
            *     *     *     *     *     *     *     *     *
          CCC CTG ACC CTC CCA CAG CAG CAA CGA TCT CAG CAG CAG CCC AGA TGC
          Pro Leu Thr Leu Pro Gln Gln Gln Arg Ser Gln Gln Gln Pro Arg Cys>
              b     b  CODING SEQUENCE CHIMERA:JUNCTION NUC.1776    b     b     >
       2840 c     c    2 1837 TO 3437 OF MCPHUPCAR4.0 FINAL       2880c    c    >

2833         2843         2853         2863         2873
                 *     *     *     *     *     *     *     *     *     *
               AAG CAG AAG GTC ATC TTT GGC AGC GGC ACG GTC ACC TTC TCA CTG AGC
               Lys Gln Lys Val Ile Phe Gly Ser Gly Thr Val Thr Phe Ser Leu Ser>
                   b     b  CODING SEQUENCE CHIMERA:JUNCTION NUC.1776    b     b     >
                 2890  c    c 1837 TO 3437 OF MCPHUPCAR4.0 FINAL    c  2930 c   >

2883         2893         2903         2913
                      *     *     *     *     *     *     *     *     *
                    TTT GAT GAG CCT CAG AAG AAC GCC ATG GCC CAC GGG AAT TCT ACG CAC
                    Phe Asp Glu Pro Gln Lys Asn Ala Met Ala His Gly Asn Ser Thr His>
                        b     b  CODING SEQUENCE CHIMERA:JUNCTION NUC.1776    b     b     >
                      2940c   c 1837 TO 3437 OF MCPHUPCAR4.0 FINAL    c    c 2980   >

2923         2933         2943         2953         2963
    *     *     *     *     *     *     *     *     *     *
  CAG AAC TCC CTG GAG GCC CAG AAA AGC AGC GAT ACG CTG ACC CGA CAC
  Gln Asn Ser Leu Glu Ala Gln Lys Ser Ser Asp Thr Leu Thr Arg His>
```

Fig. 2H

```
                   b    b  CODING SEQUENCE CHIMERA:JUNCTION NUC.1776    b     b   >
                   c 2990 c  1837 TO 3437 OF MCPHUPCAR4.0 FINAL 0 c     c    3030>

2973        2983         2993         3003         3013
    *    *     *    *      *    *       *    *       *    *
  CAG CCA TTA CTC CCG CTG CAG TGC GGG GAA ACG GAC TTA GAT CTG ACC
  Gln Pro Leu Leu Pro Leu Gln Cys Gly Glu Thr Asp Leu Asp Leu Thr>
                   b    b  CODING SEQUENCE CHIMERA:JUNCTION NUC.1776    b     b   >
                   c    c 3040 1837 TO 3437 OF MCPHUPCAR4.0 FINAL 3070  c     c   >

3023        3033         3043         3053         3063
    *    *     *    *      *    *       *    *       *    *
  GTC CAG GAA ACA GGT CTG CAA GGA CCT GTG GGT GGA GAC CAG CGG CCA
  Val Gln Glu Thr Gly Leu Gln Gly Pro Val Gly Gly Asp Gln Arg Pro>
                   b    b  CODING SEQUENCE CHIMERA:JUNCTION NUC.1776    b     b   >
   3080 c       c     3 1837 TO 3437 OF MCPHUPCAR4.0 FINAL    3120c     c     >

3073         3083          3093         3103          3113
         *    *      *    *        *    *       *    *        *    *
       GAG GTG GAG GAC CCT GAA GAG TTG TCC CCA GCA CTT GTA GTG TCC AGT
       Glu Val Glu Asp Pro Glu Glu Leu Ser Pro Ala Leu Val Val Ser Ser>
                       b    b  CODING SEQUENCE CHIMERA:JUNCTION NUC.1776    b     b   >
         3130 c     c  1837 TO 3437 OF MCPHUPCAR4.0 FINAL    c  3170 c     >

3123         3133          3143         3153
              *    *      *    *        *    *       *    *
            TCA CAG AGC TTT GTC ATC AGT GGT GGA GGC AGC ACT GTT ACA GAA AAC
            Ser Gln Ser Phe Val Ile Ser Gly Gly Gly Ser Thr Val Thr Glu Asn>
                         b    b  CODING SEQUENCE CHIMERA:JUNCTION NUC.1776    b     b   >
              3180c    c  1837 TO 3437 OF MCPHUPCAR4.0 FINAL    c     c 3220  >

3163         3173         3183          3193         3203         3213
    *    *      *    *       *    *        *    *       *    *       *    *
  GTA GTG AAT TCA T AAAATGGA AGGAGAAGAC TGGGCTAGGG AGAATGCAGA
  Val Val Asn Ser Xxx>
       CODING SEQ  b >
              c 3230  1837 TO 3437 OF MCPHUPCAR4.0 FINAL   c    3270      >

3223         3233         3243         3253         3263         3273
              *    *      *    *       *    *       *    *       *    *       *    *
          GAGGTTTCTT GGGGTCCCAG GGATGAGGAA TCGCCCCAGA CTCCTTTCCT CTGAGGAAGA
              3280  c       1837 TO 3437 OF MCPHUPCAR4.0 FINAL 0   c      3330     >

3283         3293         3303         3313         3323         3333
                 *    *      *    *       *    *       *    *       *    *       *    *
             AGGGATAATA GACACATCAA ATGCCCCGAA TTTAGTCACA CCATCTTAAA TGACAGTGAA
                 3340  c       1837 TO 3437 OF MCPHUPCAR4.0 FINAL 0   c      3390     >

3343         3353         3363         3373
                   *    *      *    *       *    *       *    *
               TTGACCCATG TTCCCTTTAA AAAAAAAAAA AAAAAAGCGG CCGC--
                   34 1837 TO 3437 OF MCPHUPCAR4.0 FINAL    c       >
```

Fig. 3A

```
Sequence Range: -40 to 3960

-31         -21         -11          -1          10
               *     *     *     *     *     *     *     *     *     *     *
          CTAGCTGTCT CATCCCTTGC CCTGGAGAGA CGGCAGAACC ATG GCA TTT TAT AGC
                                                     Met Ala Phe Tyr Ser>
                                                         TRANSLATION    >

20          30          40          50          60
           *     *     *     *     *     *     *     *     *
          TGC TGC TGG GTC CTC TTG GCA CTC ACC TGG CAC ACC TCT GCC TAC GGG
          Cys Cys Trp Val Leu Leu Ala Leu Thr Trp His Thr Ser Ala Tyr Gly>
           a   a   a   a   TRANSLATION OF CAR/R1 [A]  a   a   a   a     >

70          80          90          100         110
           *     *     *     *     *     *     *     *     *     *     *
          CCA GAC CAG CGA GCC CAA AAG AAG GGG GAC ATT ATC CTT GGG GGG CTC
          Pro Asp Gln Arg Ala Gln Lys Lys Gly Asp Ile Ile Leu Gly Gly Leu>
           a   a   a   a   TRANSLATION OF CAR/R1 [A]  a   a   a   a     >

120         130         140         150
           *     *     *     *     *     *     *     *     *
          TTT CCT ATT CAT TTT GGA GTA GCA GCT AAA GAT CAA GAT CTC AAA TCA
          Phe Pro Ile His Phe Gly Val Ala Ala Lys Asp Gln Asp Leu Lys Ser>
           a   a   a   a   TRANSLATION OF CAR/R1 [A]  a   a   a   a     >

160         170         180         190         200
     *     *     *     *     *     *     *     *     *     *
    AGG CCG GAG TCT GTG GAA TGT ATC AGG TAT AAT TTC CGT GGG TTT CGC
    Arg Pro Glu Ser Val Glu Cys Ile Arg Tyr Asn Phe Arg Gly Phe Arg>
     a   a   a   a   TRANSLATION OF CAR/R1 [A]  a   a   a   a     >

210         220         230         240         250
           *     *     *     *     *     *     *     *     *     *
          TGG TTA CAG GCT ATG ATA TTT GCC ATA GAG GAG ATA AAC AGC AGC CCA
          Trp Leu Gln Ala Met Ile Phe Ala Ile Glu Glu Ile Asn Ser Ser Pro>
           a   a   a   a   TRANSLATION OF CAR/R1 [A]  a   a   a   a     >

260         270         280         290         300
           *     *     *     *     *     *     *     *     *
          GCC CTT CTT CCC AAC TTG ACG CTG GGA TAC AGG ATA TTT GAC ACT TGC
          Ala Leu Leu Pro Asn Leu Thr Leu Gly Tyr Arg Ile Phe Asp Thr Cys>
           a   a   a   a   TRANSLATION OF CAR/R1 [A]  a   a   a   a     >

310         320         330         340         350
           *     *     *     *     *     *     *     *     *     *
          AAC ACC GTT TCT AAG GCC TTG GAA GCC ACC CTG AGT TTT GTT GCT CAA
          Asn Thr Val Ser Lys Ala Leu Glu Ala Thr Leu Ser Phe Val Ala Gln>
           a   a   a   a   TRANSLATION OF CAR/R1 [A]  a   a   a   a     >

360         370         380         390
           *     *     *     *     *     *     *     *     *
          AAC AAA ATT GAT TCT TTG AAC CTT GAT GAG TTC TGC AAC TGC TCA GAG
          Asn Lys Ile Asp Ser Leu Asn Leu Asp Glu Phe Cys Asn Cys Ser Glu>
           a   a   a   a   TRANSLATION OF CAR/R1 [A]  a   a   a   a     >

400         410         420         430         440
     *     *     *     *     *     *     *     *     *     *
    CAC ATT CCC TCT ACG ATT GCT GTG GTG GGA GCA ACT GGC TCA GGC GTC
    His Ile Pro Ser Thr Ile Ala Val Val Gly Ala Thr Gly Ser Gly Val>
     a   a   a   a   TRANSLATION OF CAR/R1 [A]  a   a   a   a     >
```

Fig. 3B

```
      450         460         470         480         490
       *     *     *     *     *     *     *     *     *     *
TCC ACG GCA GTG GCA AAT CTG CTG GGG CTC TTC TAC ATT CCC CAG GTC
Ser Thr Ala Val Ala Asn Leu Leu Gly Leu Phe Tyr Ile Pro Gln Val>
  a   a   a   a   TRANSLATION OF CAR/R1 [A]     a   a   a   a   >

500         510         520         530         540
       *     *     *     *     *     *     *     *     *     *
AGT TAT GCC TCC TCC AGC AGA CTC CTC AGC AAC AAG AAT CAA TTC AAG
Ser Tyr Ala Ser Ser Ser Arg Leu Leu Ser Asn Lys Asn Gln Phe Lys>
  a   a   a   a   TRANSLATION OF CAR/R1 [A]     a   a   a   a   >

550         560         570         580         590
         *     *     *     *     *     *     *     *     *     *
TCT TTC CTC CGA ACC ATC CCC AAT GAT GAG CAC CAG GCC ACT GCC ATG
Ser Phe Leu Arg Thr Ile Pro Asn Asp Glu His Gln Ala Thr Ala Met>
  a   a   a   a   TRANSLATION OF CAR/R1 [A]     a   a   a   a   >

600         610         620         630
             *     *     *     *     *     *     *     *     *
GCA GAC ATC ATC GAG TAT TTC CGC TGG AAC TGG GTG GGC ACA ATT GCA
Ala Asp Ile Ile Glu Tyr Phe Arg Trp Asn Trp Val Gly Thr Ile Ala>
  a   a   a   a   TRANSLATION OF CAR/R1 [A]     a   a   a   a   >

640         650         660         670         680
 *     *     *     *     *     *     *     *     *     *
GCT GAT GAC GAC TAT GGG CGG CCG GGG ATT GAG AAA TTC CGA GAG GAA
Ala Asp Asp Asp Tyr Gly Arg Pro Gly Ile Glu Lys Phe Arg Glu Glu>
  a   a   a   a   TRANSLATION OF CAR/R1 [A]     a   a   a   a   >

690         700         710         720         730
 *     *     *     *     *     *     *     *     *     *
GCT GAG GAA AGG GAT ATC TGC ATC GAC TTC AGT GAA CTC ATC TCC CAG
Ala Glu Glu Arg Asp Ile Cys Ile Asp Phe Ser Glu Leu Ile Ser Gln>
  a   a   a   a   TRANSLATION OF CAR/R1 [A]     a   a   a   a   >

740         750         760         770         780
         *     *     *     *     *     *     *     *     *     *
TAC TCT GAT GAG GAA GAG ATC CAG CAT GTG GTA GAG GTG ATT CAA AAT
Tyr Ser Asp Glu Glu Glu Ile Gln His Val Val Glu Val Ile Gln Asn>
  a   a   a   a   TRANSLATION OF CAR/R1 [A]     a   a   a   a   >

790         800         810         820         830
         *     *     *     *     *     *     *     *     *     *
TCC ACG GCC AAA GTC ATC GTG GTT TTC TCC AGT GGC CCA GAT CTT GAG
Ser Thr Ala Lys Val Ile Val Val Phe Ser Ser Gly Pro Asp Leu Glu>
  a   a   a   a   TRANSLATION OF CAR/R1 [A]     a   a   a   a   >

840         850         860         870
             *     *     *     *     *     *     *     *     *
CCC CTC ATC AAG GAG ATT GTC CGG CGC AAT ATC ACG GGC AAG ATC TGG
Pro Leu Ile Lys Glu Ile Val Arg Arg Asn Ile Thr Gly Lys Ile Trp>
  a   a   a   a   TRANSLATION OF CAR/R1 [A]     a   a   a   a   >

880         890         900         910         920
 *     *     *     *     *     *     *     *     *     *
CTG GCC AGC GAG GCC TGG GCC AGC TCC TCC CTG ATC GCC ATG CCT CAG
Leu Ala Ser Glu Ala Trp Ala Ser Ser Ser Leu Ile Ala Met Pro Gln>
  a   a   a   a   TRANSLATION OF CAR/R1 [A]     a   a   a   a   >

```
         TAC TTC CAC GTG GTT GGC GGC ACC ATT GGA TTC GCT CTG AAG GCT GGG
         Tyr Phe His Val Val Gly Gly Thr Ile Gly Phe Ala Leu Lys Ala Gly>
            a   a   a   a  TRANSLATION OF CAR/R1 [A]   a   a   a   a   >

980         990        1000        1010        1020
             *     *     *     *     *     *     *     *     *
         CAG ATC CCA GGC TTC CGG GAA TTC CTG AAG AAG GTC CAT CCC AGG AAG
         Gln Ile Pro Gly Phe Arg Glu Phe Leu Lys Lys Val His Pro Arg Lys>
            a   a   a   a  TRANSLATION OF CAR/R1 [A]   a   a   a   a   >

1030        1040        1050        1060        1070
             *     *     *     *     *     *     *     *     *     *
         TCT GTC CAC AAT GGT TTT GCC AAG GAG TTT TGG GAA GAA ACA TTT AAC
         Ser Val His Asn Gly Phe Ala Lys Glu Phe Trp Glu Glu Thr Phe Asn>
            a   a   a   a  TRANSLATION OF CAR/R1 [A]   a   a   a   a   >

1080        1090        1100        1110
             *     *     *     *     *     *     *     *     *
         TGC CAC CTC CAA GAA GGT GCA AAA GGA CCT TTA CCT GTG GAC ACC TTT
         Cys His Leu Gln Glu Gly Ala Lys Gly Pro Leu Pro Val Asp Thr Phe>
            a   a   a   a  TRANSLATION OF CAR/R1 [A]   a   a   a   a   >

1120        1130        1140        1150        1160
     *     *     *     *     *     *     *     *     *     *
         CTG AGA GGT CAC GAA GAA AGT GGC GAC AGG TTT AGC AAC AGC TCG ACA
         Leu Arg Gly His Glu Glu Ser Gly Asp Arg Phe Ser Asn Ser Ser Thr>
            a   a   a   a  TRANSLATION OF CAR/R1 [A]   a   a   a   a   >

1170        1180        1190        1200        1210
             *     *     *     *     *     *     *     *     *     *
         GCC TTC CGA CCC CTC TGT ACA GGG GAT GAG AAC ATC AGC AGT GTC GAG
         Ala Phe Arg Pro Leu Cys Thr Gly Asp Glu Asn Ile Ser Ser Val Glu>
            a   a   a   a  TRANSLATION OF CAR/R1 [A]   a   a   a   a   >

1220        1230        1240        1250        1260
             *     *     *     *     *     *     *     *     *
         ACC CCT TAC ATA GAT TAC ACG CAT TTA CGG ATA TCC TAC AAT GTG TAC
         Thr Pro Tyr Ile Asp Tyr Thr His Leu Arg Ile Ser Tyr Asn Val Tyr>
            a   a   a   a  TRANSLATION OF CAR/R1 [A]   a   a   a   a   >

1270        1280        1290        1300        1310
             *     *     *     *     *     *     *     *     *     *
         TTA GCA GTC TAC TCC ATT GCC CAC GCC TTG CAA GAT ATA TAT ACC TGC
         Leu Ala Val Tyr Ser Ile Ala His Ala Leu Gln Asp Ile Tyr Thr Cys>
            a   a   a   a  TRANSLATION OF CAR/R1 [A]   a   a   a   a   >

1320        1330        1340        1350
             *     *     *     *     *     *     *     *     *
         TTA CCT GGG AGA GGG CTC TTC ACC AAT GGC TCC TGT GCA GAC ATC AAG
         Leu Pro Gly Arg Gly Leu Phe Thr Asn Gly Ser Cys Ala Asp Ile Lys>
            a   a   a   a  TRANSLATION OF CAR/R1 [A]   a   a   a   a   >

1360        1370        1380        1390        1400
     *     *     *     *     *     *     *     *     *     *
         AAA GTT GAG GCG TGG CAG GTC CTG AAG CAC CTA CGG CAT CTA AAC TTT
         Lys Val Glu Ala Trp Gln Val Leu Lys His Leu Arg His Leu Asn Phe>
            a   a   a   a  TRANSLATION OF CAR/R1 [A]   a   a   a   a   >

1410        1420        1430        1440        1450
     *     *     *     *     *     *     *     *     *     *
         ACA AAC AAT ATG GGG GAG CAG GTG ACC TTT GAT GAG TGT GGT GAC CTG
         Thr Asn Asn Met Gly Glu Gln Val Thr Phe Asp Glu Cys Gly Asp Leu>
```

Fig.3D

```
             a    a    a    a    TRANSLATION OF CAR/R1 [A]    a    a    a    a    >

1460         1470         1480         1490         1500
             *    *    *    *    *    *    *    *    *    *
           GTG  GGG  AAC  TAT  TCC  ATC  ATC  AAC  TGG  CAC  CTC  TCC  CCA  GAG  GAT  GGC
           Val  Gly  Asn  Tyr  Ser  Ile  Ile  Asn  Trp  His  Leu  Ser  Pro  Glu  Asp  Gly>
             a    a    a    a    TRANSLATION OF CAR/R1 [A]    a    a    a    a    >

1510         1520         1530         1540         1550
             *    *    *    *    *    *    *    *    *    *
           TCC  ATC  GTG  TTT  AAG  GAA  GTC  GGG  TAT  TAC  AAC  GTC  TAT  GCC  AAG  AAG
           Ser  Ile  Val  Phe  Lys  Glu  Val  Gly  Tyr  Tyr  Asn  Val  Tyr  Ala  Lys  Lys>
             a    a    a    a    TRANSLATION OF CAR/R1 [A]    a    a    a    a    >

1560         1570         1580         1590
             *    *    *    *    *    *    *    *    *
           GGA  GAA  AGA  CTC  TTC  ATC  AAC  GAG  GAG  AAA  ATC  CTG  TGG  AGT  GGG  TTC
           Gly  Glu  Arg  Leu  Phe  Ile  Asn  Glu  Glu  Lys  Ile  Leu  Trp  Ser  Gly  Phe>
             a    a    a    a    TRANSLATION OF CAR/R1 [A]    a    a    a    a    >

1600         1610         1620         1630         1640
        *    *    *    *    *    *    *    *    *    *
        TCC  AGG  GAG  GTG  CCC  TTC  TCC  AAC  TGC  AGC  CGA  GAC  TGC  CTG  GCA  GGG
        Ser  Arg  Glu  Val  Pro  Phe  Ser  Asn  Cys  Ser  Arg  Asp  Cys  Leu  Ala  Gly>
             a    a    a    a    TRANSLATION OF CAR/R1 [A]    a    a    a    a    >

1650         1660         1670         1680         1690
             *    *    *    *    *    *    *    *    *    *
           ACC  AGG  AAA  GGG  ATC  ATT  GAG  GGG  GAG  CCC  ACC  TGC  TGC  TTT  GAG  TGT
           Thr  Arg  Lys  Gly  Ile  Ile  Glu  Gly  Glu  Pro  Thr  Cys  Cys  Phe  Glu  Cys>
             a    a    a    a    TRANSLATION OF CAR/R1 [A]    a    a    a    a    >

1700         1710         1720         1730         1740
             *    *    *    *    *    *    *    *    *    *
           GTG  GAG  TGT  CCT  GAT  GGG  GAG  TAT  AGT  GAT  GAG  ACA  GAT  GCC  AGT  GCC
           Val  Glu  Cys  Pro  Asp  Gly  Glu  Tyr  Ser  Asp  Glu  Thr  Asp  Ala  Ser  Ala>
             a    a    a    a    TRANSLATION OF CAR/R1 [A]    a    a    a    a    >

1750         1760         1770         1780         1790
             *    *    *    *    *    *    *    *    *    *
           TGT  AAC  AAG  TGC  CCA  GAT  GAC  TTC  TGG  TCC  AAT  GAG  AAC  CAC  ACC  TCC
           Cys  Asn  Lys  Cys  Pro  Asp  Asp  Phe  Trp  Ser  Asn  Glu  Asn  His  Thr  Ser>
             a    a    a    a    TRANSLATION OF CAR/R1 [A]    a    a    a    a    >

1800         1810         1820         1830
             *    *    *    *    *    *    *    *    *
           TGC  GAG  CCC  ATT  CCT  GTC  CGT  TAT  CTT  GAG  TGG  AGT  GAC  ATA  GAA  TCT
           Cys  Glu  Pro  Ile  Pro  Val  Arg  Tyr  Leu  Glu  Trp  Ser  Asp  Ile  Glu  Ser>
             a    a    a    a    TRANSLATION OF CAR/R1 [A]    a    a    a    a    >

1840         1850         1860         1870         1880
        *    *    *    *    *    *    *    *    *    *
        ATC  ATA  GCC  ATC  GCC  TTT  TCT  TGC  CTG  GGC  ATC  CTC  GTG  ACG  CTG  TTT
        Ile  Ile  Ala  Ile  Ala  Phe  Ser  Cys  Leu  Gly  Ile  Leu  Val  Thr  Leu  Phe>
             a    a    a    a    TRANSLATION OF CAR/R1 [A]    a    a    a    a    >

1890         1900         1910         1920         1930
             *    *    *    *    *    *    *    *    *    *
           GTC  ACC  CTC  ATC  TTC  GTT  CTG  TAC  CGG  GAC  ACA  CCC  GTG  GTC  AAA  TCC
           Val  Thr  Leu  Ile  Phe  Val  Leu  Tyr  Arg  Asp  Thr  Pro  Val  Val  Lys  Ser>
             a    a    a    a    TRANSLATION OF CAR/R1 [A]    a    a    a    a    >
```

Fig. 3E

```
              1940          1950          1960          1970          1980
                *             *             *             *             *
         TCC AGT AGG GAG CTC TGC TAT ATC ATT CTG GCT GGT ATT TTC CTC GGC
         Ser Ser Arg Glu Leu Cys Tyr Ile Ile Leu Ala Gly Ile Phe Leu Gly>
          a   a   a   a    TRANSLATION OF CAR/R1 [A]    a   a   a   a  >

1990          2000          2010          2020          2030
                *             *             *             *             *
         TAT GTG TGC CCT TTC ACC CTC ATC GCC AAA CCT ACT ACC ACA TCC TGC
         Tyr Val Cys Pro Phe Thr Leu Ile Ala Lys Pro Thr Thr Thr Ser Cys>
          a   a   a   a    TRANSLATION OF CAR/R1 [A]    a   a   a   a  >

2040          2050          2060          2070
                *             *             *             *
         TAC CTC CAG CGC CTC CTA GTT GGC CTC TCT TCT GCC ATG TGC TAC TCT
         Tyr Leu Gln Arg Leu Leu Val Gly Leu Ser Ser Ala Met Cys Tyr Ser>
          a   a   a   a    TRANSLATION OF CAR/R1 [A]    a   a   a   a  >

2080          2090          2100          2110          2120
  *             *             *             *             *             *
GCT TTA GTG ACC AAA ACC AAT CGT ATT GCA CGC ATC CTG GCT GGC AGC
Ala Leu Val Thr Lys Thr Asn Arg Ile Ala Arg Ile Leu Ala Gly Ser>
 a   a   a   a    TRANSLATION OF CAR/R1 [A]    a   a   a   a  >

2130          2140          2150          2160          2170
      *             *             *             *             *
    AAG AAG AAG ATC TGC ACC CGG AAG CCC AGA TTC ATG AGC GCT TGG GCC
    Lys Lys Lys Ile Cys Thr Arg Lys Pro Arg Phe Met Ser Ala Trp Ala>
     a   a   a   a    TRANSLATION OF CAR/R1 [A]    a   a   a   a  >

2180          2190          2200          2210          2220
           *             *             *             *             *
         CAA GTG ATC ATA GCC TCC ATT CTG ATT AGT GTA CAG CTA ACA CTA GTG
         Gln Val Ile Ile Ala Ser Ile Leu Ile Ser Val Gln Leu Thr Leu Val>
          a   a   a   a    TRANSLATION OF CAR/R1 [A]    a   a   a   a  >

2230          2240          2250          2260          2270
                *             *             *             *             *
         GTG ACC TTG ATC ATC ATG GAG CCT CCC ATG CCC ATT TTG TCC TAC CCG
         Val Thr Leu Ile Ile Met Glu Pro Pro Met Pro Ile Leu Ser Tyr Pro>
          a   a   a   a    TRANSLATION OF CAR/R1 [A]    a   a   a   a  >

2280          2290          2300          2310
                     *             *             *             *
              AGT ATC AAG GAA GTC TAC CTT ATC TGC AAT ACC AGC AAC CTG GGT GTA
              Ser Ile Lys Glu Val Tyr Leu Ile Cys Asn Thr Ser Asn Leu Gly Val>
               a   a   a   a    TRANSLATION OF CAR/R1 [A]    a   a   a   a  >

2320          2330          2340          2350          2360
  *             *             *             *             *             *
GTG GCC CCT GTG GGT TAC AAT GGA CTC CTC ATC ATG AGC TGT ACC TAC
Val Ala Pro Val Gly Tyr Asn Gly Leu Leu Ile Met Ser Cys Thr Tyr>
 a   a   a   a    TRANSLATION OF CAR/R1 [A]    a   a   a   a  >

2370          2380          2390          2400          2410
      *             *             *             *             *
    TAT GCC TTC AAG ACC CGC AAC GTG CCG GCC AAC TTC AAT GAG GCT AAA
    Tyr Ala Phe Lys Thr Arg Asn Val Pro Ala Asn Phe Asn Glu Ala Lys>
     a   a   a   a    TRANSLATION OF CAR/R1 [A]    a   a   a   a  >

```
         TAC ATC GCC TTC ACC ATG TAC ACT ACC TGC ATC ATC TGG CTG GCT TTC
         Tyr Ile Ala Phe Thr Met Tyr Thr Thr Cys Ile Ile Trp Leu Ala Phe>
           a   a   a   a   TRANSLATION OF CAR/R1 [A]   a   a   a   a   >

2470        2480        2490        2500        2510
           *     *     *     *     *     *     *     *     *     *
         GTT CCC ATT TAC TTT GGG AGC AAC TAC AAG ATC ATC ACT ACC TGC TTC
         Val Pro Ile Tyr Phe Gly Ser Asn Tyr Lys Ile Ile Thr Thr Cys Phe>
           a   a   a   a   TRANSLATION OF CAR/R1 [A]   a   a   a   a   >

2520        2530        2540        2550
              *     *     *     *     *     *     *     *     *
         GCG GTG AGC CTC AGT GTG ACG GTG GCC CTG GGG TGC ATG TTT ACT CCG
         Ala Val Ser Leu Ser Val Thr Val Ala Leu Gly Cys Met Phe Thr Pro>
           a   a   a   a   TRANSLATION OF CAR/R1 [A]   a   a   a   a   >

2560        2570        2580        2590        2600
        *     *     *     *     *     *     *     *     *     *
         AAG ATG TAC ATC ATC ATT GCC AAA CCT GAG AGG AAC GTC CGC AGT GCC
         Lys Met Tyr Ile Ile Ile Ala Lys Pro Glu Arg Asn Val Arg Ser Ala>
           a   a   a   a   TRANSLATION OF CAR/R1 [A]   a   a   a   a   >

2610        2620        2630        2640        2650
        *     *     *     *     *     *     *     *     *     *
         TTC ACG ACC TCT GAT GTT GTC CGC ATG CAC GTC GGT GAT GGC AAA CTG
         Phe Thr Thr Ser Asp Val Val Arg Met His Val Gly Asp Gly Lys Leu>
           a   a   a   a   TRANSLATION OF CAR/R1 [A]   a   a   a   a   >

2660        2670        2680        2690        2700
           *     *     *     *     *     *     *     *     *     *
         CCG TGC CGC TCC AAC ACC TTC CTC AAC ATT TTC CGG AGA AAG AAG CCC
         Pro Cys Arg Ser Asn Thr Phe Leu Asn Ile Phe Arg Arg Lys Lys Pro>
           a   a   a   a   TRANSLATION OF CAR/R1 [A]   a   a   a   a   >

2710        2720        2730        2740        2750
           *     *     *     *     *     *     *     *     *     *
         GGG GCA GGG AAT GCC AAT TCT AAC GGC AAG TCT GTG TCA TGG TCT GAA
         Gly Ala Gly Asn Ala Asn Ser Asn Gly Lys Ser Val Ser Trp Ser Glu>
           a   a   a   a   TRANSLATION OF CAR/R1 [A]   a   a   a   a   >

2760        2770        2780        2790
              *     *     *     *     *     *     *     *     *
         CCA GGT GGA AGA CAG GCG CCC AAG GGA CAG CAC GTG TGG CAG CGC CTC
         Pro Gly Gly Arg Gln Ala Pro Lys Gly Gln His Val Trp Gln Arg Leu>
           a   a   a   a   TRANSLATION OF CAR/R1 [A]   a   a   a   a   >

2800        2810        2820        2830        2840
        *     *     *     *     *     *     *     *     *     *
         TCT GTG CAC GTG AAG ACC AAC GAG ACG GCC TGT AAC CAA ACA GCC GTA
         Ser Val His Val Lys Thr Asn Glu Thr Ala Cys Asn Gln Thr Ala Val>
           a   a   a   a   TRANSLATION OF CAR/R1 [A]   a   a   a   a   >

2850        2860        2870        2880        2890
        *     *     *     *     *     *     *     *     *     *
         ATC AAA CCC CTC ACT AAA AGT TAC CAA GGC TCT GGC AAG AGC CTG ACC
         Ile Lys Pro Leu Thr Lys Ser Tyr Gln Gly Ser Gly Lys Ser Leu Thr>
           a   a   a   a   TRANSLATION OF CAR/R1 [A]   a   a   a   a   >

2900        2910        2920        2930        2940
           *     *     *     *     *     *     *     *     *     *
         TTT TCA GAT GCC AGC ACC AAG ACC CTT TAC AAT GTG GAA GAA GAG GAC
         Phe Ser Asp Ala Ser Thr Lys Thr Leu Tyr Asn Val Glu Glu Glu Asp>
```

Fig. 3G

```
            a    a    a    a    TRANSLATION OF CAR/R1 [A]      a    a    a    a    >
             2950          2960          2970          2980          2990
          *    *    *    *    *    *    *    *    *    *
         AAT ACC CCT TCT GCT CAC TTC AGC CCT CCC AGC AGC CCT TCT ATG GTG
         Asn Thr Pro Ser Ala His Phe Ser Pro Pro Ser Ser Pro Ser Met Val>
            a    a    a    a    TRANSLATION OF CAR/R1 [A]      a    a    a    a    >
             3000          3010          3020          3030
          *    *    *    *    *    *    *    *    *
         GTG CAC CGA CGC GGG CCA CCC GTG GCC ACC ACA CCA CCT CTG CCA CCC
         Val His Arg Arg Gly Pro Pro Val Ala Thr Thr Pro Pro Leu Pro Pro>
            a    a    a    a    TRANSLATION OF CAR/R1 [A]      a    a    a    a    >
    3040          3050          3060          3070          3080
      *    *    *    *    *    *    *    *    *    *
     CAT CTG ACC GCA GAA GAG ACC CCC CTG TTC CTG GCT GAT TCC GTC ATC
     His Leu Thr Ala Glu Glu Thr Pro Leu Phe Leu Ala Asp Ser Val Ile>
            a    a    a    a    TRANSLATION OF CAR/R1 [A]      a    a    a    a    >
    3090          3100          3110          3120          3130
      *    *    *    *    *    *    *    *    *    *    *
     CCC AAG GGC TTG CCT CCT CCT CTC CCG CAG CAG CAG CCA CAG CAG CCG
     Pro Lys Gly Leu Pro Pro Pro Leu Pro Gln Gln Gln Pro Gln Gln Pro>
            a    a    a    a    TRANSLATION OF CAR/R1 [A]      a    a    a    a    >
         3140          3150          3160          3170          3180
          *    *    *    *    *    *    *    *    *
         CCC CCT CAG CAG CCC CCG CAG CAG CCC AAG TCC CTG ATG GAC CAG CTG
         Pro Pro Gln Gln Pro Pro Gln Gln Pro Lys Ser Leu Met Asp Gln Leu>
            a    a    a    a    TRANSLATION OF CAR/R1 [A]      a    a    a    a    >
             3190          3200          3210          3220          3230
          *    *    *    *    *    *    *    *    *    *
         CAA GGC GTA GTC ACC AAC TTC GGT TCG GGG ATT CCA GAT TTC CAT GCG
         Gln Gly Val Val Thr Asn Phe Gly Ser Gly Ile Pro Asp Phe His Ala>
            a    a    a    a    TRANSLATION OF CAR/R1 [A]      a    a    a    a    >
             3240          3250          3260          3270
          *    *    *    *    *    *    *    *    *
         GTG CTG GCA GGC CCG GGG ACA CCA GGA AAC AGC CTG CGC TCT CTG TAC
         Val Leu Ala Gly Pro Gly Thr Pro Gly Asn Ser Leu Arg Ser Leu Tyr>
            a    a    a    a    TRANSLATION OF CAR/R1 [A]      a    a    a    a    >
    3280          3290          3300          3310          3320
      *    *    *    *    *    *    *    *    *    *
     CCG CCC CCG CCT CCG CCG CAA CAC CTG CAG ATG CTG CCC CTG CAC CTG
     Pro Pro Pro Pro Pro Pro Gln His Leu Gln Met Leu Pro Leu His Leu>
            a    a    a    a    TRANSLATION OF CAR/R1 [A]      a    a    a    a    >
         3330          3340          3350          3360          3370
          *    *    *    *    *    *    *    *    *    *
         AGC ACC TTC CAG GAG GAG TCC ATC TCC CCT CCT GGG GAG GAC ATC GAT
         Ser Thr Phe Gln Glu Glu Ser Ile Ser Pro Pro Gly Glu Asp Ile Asp>
            a    a    a    a    TRANSLATION OF CAR/R1 [A]      a    a    a    a    >
             3380          3390          3400          3410          3420
          *    *    *    *    *    *    *    *    *
         GAT GAC AGT GAG AGA TTC AAG CTC CTG CAG GAG TTC GTG TAC GAG CGC
         Asp Asp Ser Glu Arg Phe Lys Leu Leu Gln Glu Phe Val Tyr Glu Arg>
            a    a    a    a    TRANSLATION OF CAR/R1 [A]      a    a    a    a    >
```

Fig. 3H

```
          3430        3440        3450        3460        3470
           *     *     *     *     *     *     *     *     *     *
         GAA GGG AAC ACC GAA GAA GAT GAA TTG GAA GAG GAG GAG GAC CTG CCC
         Glu Gly Asn Thr Glu Glu Asp Glu Leu Glu Glu Glu Glu Asp Leu Pro>
          a   a   a   a   TRANSLATION OF CAR/R1 [A]   a   a   a   a   >

3480        3490        3500        3510
           *     *     *     *     *     *     *     *     *
         ACA GCC AGC AAG CTG ACC CCT GAG GAT TCT CCT GCC CTG ACG CCT CCT
         Thr Ala Ser Lys Leu Thr Pro Glu Asp Ser Pro Ala Leu Thr Pro Pro>
          a   a   a   a   TRANSLATION OF CAR/R1 [A]   a   a   a   a   >

3520        3530        3540        3550        3560
     *     *     *     *     *     *     *     *     *     *
   TCT CCT TTC CGA GAT TCC GTG GCC TCT GGC AGC TCA GTG CCC AGT TCC
   Ser Pro Phe Arg Asp Ser Val Ala Ser Gly Ser Ser Val Pro Ser Ser>
    a   a   a   a   TRANSLATION OF CAR/R1 [A]   a   a   a   a   >

3570        3580        3590        3600        3610
     *     *     *     *     *     *     *     *     *     *
   CCC GTA TCT GAG TCG GTC CTC TGC ACC CCT CCA AAT GTA ACC TAC GCC
   Pro Val Ser Glu Ser Val Leu Cys Thr Pro Pro Asn Val Thr Tyr Ala>
    a   a   a   a   TRANSLATION OF CAR/R1 [A]   a   a   a   a   >

3620        3630        3640        3650        3660
     *     *     *     *     *     *     *     *     *     *
   TCT GTC ATT CTG AGG GAC TAC AAG CAA AGC TCT TCC ACC CTG TAG
   Ser Val Ile Leu Arg Asp Tyr Lys Gln Ser Ser Ser Thr Leu ***>
    a   a   a       TRANSLATION OF CAR/R1 [A]   a   a   a   >

3670        3680        3690        3700        3710        3720
               *     *     *     *     *     *     *     *     *     *     *     *
             TGTGTGTGTG TGTGTGGGGG CGGGGGGAGT GCGCATGGAG AAGCCAGAGA TGCCAAGGAG 3730        3740        3750        3760        3770        3780
               *     *     *     *     *     *     *     *     *     *     *     *
             TGTCAACCCT TCCAGAAATG TGTAGAAAGC AGGGTGAGGG ATGGGGATGG AGGACCACGG 3790        3800        3810        3820        3830        3840
               *     *     *     *     *     *     *     *     *     *     *     *
             TCTGCAGGGA AGAAAAAAAA AATGCTGCGG CTGCCTTAAA GAAGGAGAGG GACGATGCCA 3850        3860        3870        3880        3890        3900
               *     *     *     *     *     *     *     *     *     *     *     *
             ACTGAACAGT GGTCCTGGCC AGGATTGTGA CTCTTGAATT ATTCAAAAAC CTTCTCTAGA 3910        3920        3930        3940        3950        3960
               *     *     *     *     *     *     *     *     *     *     *     *
             AAGAAAGGGA ATTATGACAA AGCACAATTC CATATGGTAT GTAACTTTTA TCGAAAAAAA
```

Fig. 4A

```
Sequence Range: -24 to 3195

-15          -5            6           16          26
               *            *            *            *           *
         GCGGTGGACC GCGTCTTCGC CACA ATG GTC CGG CTC CTC TTG ATT TTC TTC CCA
                              Met Val Arg Leu Leu Leu Ile Phe Phe Pro>
                              a  TRANSLATION OF PRATCH3 [A]    a     >

36           46           56           66          76
               *            *            *            *           *
         ATG ATC TTT TTG GAG ATG TCC ATT TTG CCC AGG ATG CCT GAC AGA AAA
         Met Ile Phe Leu Glu Met Ser Ile Leu Pro Arg Met Pro Asp Arg Lys>
          a   a   a   a TRANSLATION OF PRATCH3 [A]  a   a   a   a    >

86           96          106          116         126
               *            *            *            *           *
         GTA TTG CTG GCA GGT GCC TCG TCC CAG CGC TCC GTG GCG AGA ATG GAC
         Val Leu Leu Ala Gly Ala Ser Ser Gln Arg Ser Val Ala Arg Met Asp>
          a   a   a   a TRANSLATION OF PRATCH3 [A]  a   a   a   a    >

136          146          156         166
                    *            *            *           *
             GGA GAT GTC ATC ATC GGA GCC CTC TTC TCA GTC CAT CAC CAG CCT CCA
             Gly Asp Val Ile Ile Gly Ala Leu Phe Ser Val His His Gln Pro Pro>
              a   a   a   a TRANSLATION OF PRATCH3 [A]   a   a   a   a    >

176          186          196          206         216
          *            *            *            *           *
         GCC GAG AAG GTA CCC GAA AGG AAG TGT GGG GAG ATC AGG GAA CAG TAT
         Ala Glu Lys Val Pro Glu Arg Lys Cys Gly Glu Ile Arg Glu Gln Tyr>
          a   a   a   a TRANSLATION OF PRATCH3 [A]  a   a   a   a    >

226          236          246          256         266
               *            *            *            *           *
         GGT ATC CAG AGG GTG GAG GCC ATG TTC CAC ACG TTG GAT AAG ATT AAC
         Gly Ile Gln Arg Val Glu Ala Met Phe His Thr Leu Asp Lys Ile Asn>
          a   a   a   a TRANSLATION OF PRATCH3 [A]  a   a   a   a    >

276          286          296          306         316
               *            *            *            *           *
         GCG GAC CCG GTG CTC CTG CCC AAC ATC ACT CTG GGC AGT GAG ATC CGG
         Ala Asp Pro Val Leu Leu Pro Asn Ile Thr Leu Gly Ser Glu Ile Arg>
          a   a   a   a TRANSLATION OF PRATCH3 [A]  a   a   a   a    >

326  ,      336          346          356         366
                   *            *            *            *           *
             GAC TCC TGC TGG CAC TCT TCA GTG GCT CTC GAA CAG AGC ATC GAA TTC
             Asp Ser Cys Trp His Ser Ser Val Ala Leu Glu Gln Ser Ile Glu Phe>
              a   a   a   a TRANSLATION OF PRATCH3 [A]   a   a   a   a    >

376          386          396          406
                   *            *            *            *
             ATC AGA GAC TCC CTG ATT TCC ATC CGA GAT GAG AAG GAT GGG CTG AAC
             Ile Arg Asp Ser Leu Ile Ser Ile Arg Asp Glu Lys Asp Gly Leu Asn>
              a   a   a   a TRANSLATION OF PRATCH3 [A]   a   a   a   a    >

416          426          436          446         456
          *            *            *            *           *
         CGA TGC CTG CCT GAT GGC CAG ACC CTG CCC CCT GGC AGG ACT AAG AAG
         Arg Cys Leu Pro Asp Gly Gln Thr Leu Pro Pro Gly Arg Thr Lys Lys>
          a   a   a   a TRANSLATION OF PRATCH3 [A]  a   a   a   a    >
```

Fig. 4B

```
       466         476         486         496         506
        *           *           *           *           *
CCT ATT GCT GGA GTG ATC GGC CCT GGC TCC AGC TCT GTG GCC ATT CAA
Pro Ile Ala Gly Val Ile Gly Pro Gly Ser Ser Ser Val Ala Ile Gln>
   a   a   a   a  TRANSLATION OF PRATCH3 [A]   a   a   a   a   >

516         526         536         546         556
        *           *           *           *           *
GTC CAG AAT CTT CTC CAG CTG TTC GAC ATC CCA CAG ATC GCC TAT TCT
Val Gln Asn Leu Leu Gln Leu Phe Asp Ile Pro Gln Ile Ala Tyr Ser>
   a   a   a   a  TRANSLATION OF PRATCH3 [A]   a   a   a   a   >

566         576         586         596         606
        *           *           *           *           *
GCC ACA AGC ATA GAC CTG AGT GAC AAA ACT TTG TAC AAA TAC TTC CTG
Ala Thr Ser Ile Asp Leu Ser Asp Lys Thr Leu Tyr Lys Tyr Phe Leu>
   a   a   a   a  TRANSLATION OF PRATCH3 [A]   a   a   a   a   >

616         626         636         646
            *           *           *           *
AGG GTG GTC CCT TCT GAC ACT TTG CAG GCA AGG GCG ATG CTC GAC ATA
Arg Val Val Pro Ser Asp Thr Leu Gln Ala Arg Ala Met Leu Asp Ile>
   a   a   a   a  TRANSLATION OF PRATCH3 [A]   a   a   a   a   >

656         666         676         686         696
  *           *           *           *           *
GTC AAG CGT TAC AAC TGG ACC TAT GTC TCA GCA GTC CAC ACA GAA GGG
Val Lys Arg Tyr Asn Trp Thr Tyr Val Ser Ala Val His Thr Glu Gly>
   a   a   a   a  TRANSLATION OF PRATCH3 [A]   a   a   a   a   >

706         716         726         736         746
      *           *           *           *           *
AAT TAC GGC GAG AGT GGA ATG GAT GCT TTC AAA GAA CTG GCT GCC CAG
Asn Tyr Gly Glu Ser Gly Met Asp Ala Phe Lys Glu Leu Ala Ala Gln>
   a   a   a   a  TRANSLATION OF PRATCH3 [A]   a   a   a   a   >

756         766         776         786         796
          *           *           *           *           *
GAA GGC CTC TGC ATC GCA CAC TCG GAC AAA ATC TAC AGC AAT GCT GGC
Glu Gly Leu Cys Ile Ala His Ser Asp Lys Ile Tyr Ser Asn Ala Gly>
   a   a   a   a  TRANSLATION OF PRATCH3 [A]   a   a   a   a   >

806         816         826         836         846
        *           *           *           *           *
GAG AAG AGC TTT GAC CGG CTC CTG CGT AAA CTC CGG GAG CGG CTT CCC
Glu Lys Ser Phe Asp Arg Leu Leu Arg Lys Leu Arg Glu Arg Leu Pro>
   a   a   a   a  TRANSLATION OF PRATCH3 [A]   a   a   a   a   >

856         866         876         886
          *           *           *           *
AAG GCC AGG GTT GTG GTC TGC TTC TGC GAG GGC ATG ACA GTG CGG GGC
Lys Ala Arg Val Val Val Cys Phe Cys Glu Gly Met Thr Val Arg Gly>
   a   a   a   a  TRANSLATION OF PRATCH3 [A]   a   a   a   a   >

896         906         916         926         936
  *           *           *           *           *
TTA CTG AGT GCC ATG CGC CGC CTG GGC GTC GTG GGC GAG TTC TCA CTC
Leu Leu Ser Ala Met Arg Arg Leu Gly Val Val Gly Glu Phe Ser Leu>
   a   a   a  .a  TRANSLATION OF PRATCH3 [A]   a   a   a   a   >

```
        ATT GGA AGT GAT GGA TGG GCA GAC AGA GAT GAA GTC ATC GAA GGC TAT
        Ile Gly Ser Asp Gly Trp Ala Asp Arg Asp Glu Val Ile Glu Gly Tyr>
           a   a   a   a  TRANSLATION OF PRATCH3 [A]  a   a   a   a   >

996         1006        1016        1026        1036
       *    *    *    *    *    *    *    *    *    *
        GAG GTG GAA GCC AAC GGA GGG ATC ACA ATA AAG CTT CAG TCT CCA GAG
        Glu Val Glu Ala Asn Gly Gly Ile Thr Ile Lys Leu Gln Ser Pro Glu>
           a   a   a   a  TRANSLATION OF PRATCH3 [A]  a   a   a   a   >

1046        1056        1066        1076        1086
       *    *    *    *    *    *    *    *    *    *
        GTC AGG TCA TTT GAT GAC TAC TTC CTG AAG CTG AGG CTG GAC ACC AAC
        Val Arg Ser Phe Asp Asp Tyr Phe Leu Lys Leu Arg Leu Asp Thr Asn>
           a   a   a   a  TRANSLATION OF PRATCH3 [A]  a   a   a   a   >

1096        1106        1116        1126
            *    *    *    *    *    *    *    *
        ACA AGG AAT CCT TGG TTC CCT GAG TTC TGG CAA CAT CGC TTC CAG TGT
        Thr Arg Asn Pro Trp Phe Pro Glu Phe Trp Gln His Arg Phe Gln Cys>
           a   a   a   a  TRANSLATION OF PRATCH3 [A]  a   a   a   a   >

1136        1146        1156        1166        1176
  *    *    *    *    *    *    *    *    *    *
        CGC CTA CCT GGA CAC CTC TTG GAA AAC CCC AAC TTT AAG AAA GTG TGC
        Arg Leu Pro Gly His Leu Leu Glu Asn Pro Asn Phe Lys Lys Val Cys>
           a   a   a   a  TRANSLATION OF PRATCH3 [A]  a   a   a   a   >

1186        1196        1206        1216        1226
       *    *    *    *    *    *    *    *    *    *
        ACA GGA AAT GAA AGC TTG GAA GAA AAC TAT GTC CAG GAC AGC AAA ATG
        Thr Gly Asn Glu Ser Leu Glu Glu Asn Tyr Val Gln Asp Ser Lys Met>
           a   a   a   a  TRANSLATION OF PRATCH3 [A]  a   a   a   a   >

1236        1246        1256        1266        1276
       *    *    *    *    *    *    *    *    *    *
        GGA TTT GTC ATC AAT GCC ATC TAT GCC ATG GCA CAT GGG CTG CAG AAC
        Gly Phe Val Ile Asn Ala Ile Tyr Ala Met Ala His Gly Leu Gln Asn>
           a   a   a   a  TRANSLATION OF PRATCH3 [A]  a   a   a   a   >

1286        1296        1306        1316        1326
           *    *    *    *    *    *    *    *    *    *
        ATG CAC CAT GCT CTG TGT CCC GGC CAT GTG GGC CTG TGT GAT GCT ATG
        Met His His Ala Leu Cys Pro Gly His Val Gly Leu Cys Asp Ala Met>
           a   a   a   a  TRANSLATION OF PRATCH3 [A]  a   a   a   a   >

1336        1346        1356        1366
             *    *    *    *    *    *    *    *    *
        AAA CCC ATT GAT GGC AGG AAG CTC CTG GAT TTC CTC ATC AAA TCC TCT
        Lys Pro Ile Asp Gly Arg Lys Leu Leu Asp Phe Leu Ile Lys Ser Ser>
           a   a   a   a  TRANSLATION OF PRATCH3 [A]  a   a   a   a   >

1376        1386        1396        1406        1416
  *    *    *    *    *    *    *    *    *    *
        TTT GTC GGA GTG TCT GGA GAG GAG GTG TGG TTC GAT GAG AAG GGG GAT
        Phe Val Gly Val Ser Gly Glu Glu Val Trp Phe Asp Glu Lys Gly Asp>
           a   a   a   a  TRANSLATION OF PRATCH3 [A]  a   a   a   a   >

1426        1436        1446        1456        1466
       *    *    *    *    *    *    *    *    *
        GCT CCC GGA AGG TAT GAC ATT ATG AAT CTG CAG TAC ACA GAA GCT AAT
        Ala Pro Gly Arg Tyr Asp Ile Met Asn Leu Gln Tyr Thr Glu Ala Asn>
```

Fig. 4D

```
            a    a    a    a  TRANSLATION OF PRATCH3 [A]     a    a    a    a  >

1476          1486          1496          1506          1516
           *         *         *         *         *         *         *         *         *         *
          CGC TAT GAC TAT GTC CAC GTG GGG ACC TGG CAT GAA GGA GTG CTG AAT
          Arg Tyr Asp Tyr Val His Val Gly Thr Trp His Glu Gly Val Leu Asn>
            a    a    a    a  TRANSLATION OF PRATCH3 [A]     a    a    a    a  >

1526          1536          1546          1556          1566
           *         *         *         *         *         *         *         *         *         *
          ATT GAT GAT TAC AAA ATC CAG ATG AAC AAA AGC GGA ATG GTA CGA TCT
          Ile Asp Asp Tyr Lys Ile Gln Met Asn Lys Ser Gly Met Val Arg Ser>
            a    a    a    a  TRANSLATION OF PRATCH3 [A]     a    a    a    a  >

1576          1586          1596          1606
           *         *         *         *         *         *         *         *         *
          GTG TGC AGT GAG CCT TGC TTA AAG GGT CAG ATT AAG GTC ATA CGG AAA
          Val Cys Ser Glu Pro Cys Leu Lys Gly Gln Ile Lys Val Ile Arg Lys>
            a    a    a    a  TRANSLATION OF PRATCH3 [A]     a    a    a    a  >

1616          1626          1636          1646          1656
  *         *         *         *         *         *         *         *         *         *
  GGA GAA GTG AGC TGC TGC TGG ATC TGC ACG GCC TGC AAA GAG AAT GAG
  Gly Glu Val Ser Cys Cys Trp Ile Cys Thr Ala Cys Lys Glu Asn Glu>
            a    a    a    a  TRANSLATION OF PRATCH3 [A]     a    a    a    a  >

1666          1676          1686          1696          1706
           *         *         *         *         *         *         *         *         *
          TTT GTG CAG GAC GAG TTC ACC TGC AGA GCC TGT GAC CTG GGG TGG TGG
          Phe Val Gln Asp Glu Phe Thr Cys Arg Ala Cys Asp Leu Gly Trp Trp>
            a    a    a    a  TRANSLATION OF PRATCH3 [A]     a    a    a    a  >

1716          1726          1736          1746          1756
           *         *         *         *         *         *         *         *         *         *
          CCC AAC GCA GAG CTC ACA GGC TGT GAG CCC ATT CCT GTC CGT TAT CTT
          Pro Asn Ala Glu Leu Thr Gly Cys Glu Pro Ile Pro Val Arg Tyr Leu>
            a    a    a    a  TRANSLATION OF PRATCH3 [A]     a    a    a    a  >

1766          1776          1786          1796          1806
           *         *         *         *         *         *         *         *         *         *
          GAG TGG AGT GAC ATA GAA TCT ATC ATA GCC ATC GCC TTT TCT TGC CTG
          Glu Trp Ser Asp Ile Glu Ser Ile Ile Ala Ile Ala Phe Ser Cys Leu>
            a    a    a    a  TRANSLATION OF PRATCH3 [A]     a    a    a    a  >

1816          1826          1836          1846
           *         *         *         *         *         *         *         *         *
          GGC ATC CTC GTG ACG CTG TTT GTC ACC CTC ATC TTC GTT CTG TAC CGG
          Gly Ile Leu Val Thr Leu Phe Val Thr Leu Ile Phe Val Leu Tyr Arg>
            a    a    a    a  TRANSLATION OF PRATCH3 [A]     a    a    a    a  >

1856          1866          1876          1886          1896
  *         *         *         *         *         *         *         *         *         *
  GAC ACA CCC GTG GTC AAA TCC TCC AGT AGG GAG CTC TGC TAT ATC ATT
  Asp Thr Pro Val Val Lys Ser Ser Ser Arg Glu Leu Cys Tyr Ile Ile>
            a    a    a    a  TRANSLATION OF PRATCH3 [A]     a    a    a    a  >

1906          1916          1926          1936          1946
           *         *         *         *         *         *         *         *         *
          CTG GCT GGT ATT TTC CTC GGC TAT GTG TGC CCT TTC ACC CTC ATC GCC
          Leu Ala Gly Ile Phe Leu Gly Tyr Val Cys Pro Phe Thr Leu Ile Ala>
            a    a    a    a  TRANSLATION OF PRATCH3 [A]     a    a    a    a  >
```

Fig. 4E

```
         1956          1966          1976          1986          1996
  *       *      *      *      *      *      *      *      *      *
AAA CCT ACT ACC ACA TCC TGC TAC CTC CAG CGC CTC CTA GTT GGC CTC
Lys Pro Thr Thr Thr Ser Cys Tyr Leu Gln Arg Leu Leu Val Gly Leu>
 a   a   a   a    TRANSLATION OF PRATCH3 [A]    a   a   a   a   >

2006          2016          2026          2036          2046
  *      *      *      *      *      *      *      *      *      *
TCT TCT GCC ATG TGC TAC TCT GCT TTA GTG ACC AAA ACC AAT CGT ATT
Ser Ser Ala Met Cys Tyr Ser Ala Leu Val Thr Lys Thr Asn Arg Ile>
 a   a   a   a    TRANSLATION OF PRATCH3 [A]    a   a   a   a   >

2056          2066          2076          2086
  *      *      *      *      *      *      *      *      *
GCA CGC ATC CTG GCT GGC AGC AAG AAG AAG ATC TGC ACC CGG AAG CCC
Ala Arg Ile Leu Ala Gly Ser Lys Lys Lys Ile Cys Thr Arg Lys Pro>
 a   a   a   a    TRANSLATION OF PRATCH3 [A]    a   a   a   a   >

2096          2106          2116          2126          2136
  *      *      *      *      *      *      *      *      *      *
AGA TTC ATG AGC GCT TGG GCC CAA GTG ATC ATA GCC TCC ATT CTG ATT
Arg Phe Met Ser Ala Trp Ala Gln Val Ile Ile Ala Ser Ile Leu Ile>
 a   a   a   a    TRANSLATION OF PRATCH3 [A]    a   a   a   a   >

2146          2156          2166          2176          2186
  *      *      *      *      *      *      *      *      *
AGT GTA CAG CTA ACA CTA GTG GTG ACC TTG ATC ATC ATG GAG CCT CCC
Ser Val Gln Leu Thr Leu Val Val Thr Leu Ile Ile Met Glu Pro Pro>
 a   a   a   a    TRANSLATION OF PRATCH3 [A]    a   a   a   a   >

2196          2206          2216          2226          2236
  *      *      *      *      *      *      *      *      *      *
ATG CCC ATT TTG TCC TAC CCG AGT ATC AAG GAA GTC TAC CTT ATC TGC
Met Pro Ile Leu Ser Tyr Pro Ser Ile Lys Glu Val Tyr Leu Ile Cys>
 a   a   a   a    TRANSLATION OF PRATCH3 [A]    a   a   a   a   >

2246          2256          2266          2276          2286
  *      *      *      *      *      *      *      *      *      *
AAT ACC AGC AAC CTG GGT GTG GTG GCC CCT TTG GGC TAC AAT GGA CTC
Asn Thr Ser Asn Leu Gly Val Val Ala Pro Leu Gly Tyr Asn Gly Leu>
 a   a   a   a    TRANSLATION OF PRATCH3 [A]    a   a   a   a   >

2296          2306          2316          2326
  *      *      *      *      *      *      *      *      *
CTC ATC ATG AGC TGT ACC TAC TAT GCC TTC AAG ACC CGC AAC GTG CCC
Leu Ile Met Ser Cys Thr Tyr Tyr Ala Phe Lys Thr Arg Asn Val Pro>
 a   a   a   a    TRANSLATION OF PRATCH3 [A]    a   a   a   a   >

2336          2346          2356          2366          2376
  *      *      *      *      *      *      *      *      *      *
GCC AAC TTC AAC GAG GCC AAA TAT ATC GCG TTC ACC ATG TAC ACC ACC
Ala Asn Phe Asn Glu Ala Lys Tyr Ile Ala Phe Thr Met Tyr Thr Thr>
 a   a   a   a    TRANSLATION OF PRATCH3 [A]    a   a   a   a   >

2386          2396          2406          2416          2426
  *      *      *      *      *      *      *      *      *
TGT ATC ATC TGG CTA GCT TTT GTG CCC ATT TAC TTT GGG AGC AAC TAC
Cys Ile Ile Trp Leu Ala Phe Val Pro Ile Tyr Phe Gly Ser Asn Tyr>
 a   a   a   a    TRANSLATION OF PRATCH3 [A]    a   a   a   a   >

```
          AAG ATC ATC ACA ACT TGC TTT GCA GTG AGT CTC AGT GTA ACA GTG GCT
          Lys Ile Ile Thr Thr Cys Phe Ala Val Ser Leu Ser Val Thr Val Ala>
             a   a   a   a  TRANSLATION OF PRATCH3 [A]  a   a   a   a   >

2486          2496          2506          2516          2526
              *       *     *       *     *       *     *       *     *       *
          CTG GGG TGC ATG TTC ACT CCC AAG ATG TAC ATC ATT ATT GCC AAG CCT
          Leu Gly Cys Met Phe Thr Pro Lys Met Tyr Ile Ile Ile Ala Lys Pro>
             a   a   a   a  TRANSLATION OF PRATCH3 [A]  a   a   a   a   >

2536          2546          2556          2566
                 *       *     *       *     *       *     *       *     *
          GAG AGG AAT ACC ATC GAG GAG GTG CGT TGC AGC ACC GCA GCT CAC GCT
          Glu Arg Asn Thr Ile Glu Glu Val Arg Cys Ser Thr Ala Ala His Ala>
             a   a   a   a  TRANSLATION OF PRATCH3 [A]  a   a   a   a   >

2576          2586          2596          2606          2616
         *       *     *       *     *       *     *       *     *       *
          TTC AAG GTG GCT GCC CGG GCC ACG CTG CGC CGC AGC AAC GTC TCC CGC
          Phe Lys Val Ala Ala Arg Ala Thr Leu Arg Arg Ser Asn Val Ser Arg>
             a   a   a   a  TRANSLATION OF PRATCH3 [A]  a   a   a   a   >

2626          2636          2646          2656          2666
          *       *     *       *     *       *     *       *     *
          AAG CGG TCC AGC AGC CTT GGA GGC TCC ACG GGA TCC ACC CCC TCC TCC
          Lys Arg Ser Ser Ser Leu Gly Gly Ser Thr Gly Ser Thr Pro Ser Ser>
             a   a   a   a  TRANSLATION OF PRATCH3 [A]  a   a   a   a   >

2676          2686          2696          2706          2716
          *       *     *       *     *       *     *       *     *       *
          TCC ATC AGC AGC AAG AGC AAC AGC GAA GAC CCA TTC CCA CAG CCC GAG
          Ser Ile Ser Ser Lys Ser Asn Ser Glu Asp Pro Phe Pro Gln Pro Glu>
             a   a   a   a  TRANSLATION OF PRATCH3 [A]  a   a   a   a   >

2726          2736          2746          2756          2766
           *       *     *       *     *       *     *       *     *       *
          AGG CAG AAG CAG CAG CAG CCG CTG GCC CTA ACC CAG CAA GAG CAG CAG
          Arg Gln Lys Gln Gln Gln Pro Leu Ala Leu Thr Gln Gln Glu Gln Gln>
             a   a   a   a  TRANSLATION OF PRATCH3 [A]  a   a   a   a   >

2776          2786          2796          2806
                 *       *     *       *     *       *     *       *     *
          CAG CAG CCC CTG ACC CTC CCA CAG CAG CAA CGA TCT CAG CAG CAG CCC
          Gln Gln Pro Leu Thr Leu Pro Gln Gln Gln Arg Ser Gln Gln Gln Pro>
             a   a   a   a  TRANSLATION OF PRATCH3 [A]  a   a   a   a   >

2816          2826          2836          2846          2856
         *       *     *       *     *       *     *       *     *       *
          AGA TGC AAG CAG AAG GTC ATC TTT GGC AGC GGC ACG GTC ACC TTC TCA
          Arg Cys Lys Gln Lys Val Ile Phe Gly Ser Gly Thr Val Thr Phe Ser>
             a   a   a   a  TRANSLATION OF PRATCH3 [A]  a   a   a   a   >

2866          2876          2886          2896          2906
          *       *     *       *     *       *     *       *     *
          CTG AGC TTT GAT GAG CCT CAG AAG AAC GCC ATG GCC CAC GGG AAT TCT
          Leu Ser Phe Asp Glu Pro Gln Lys Asn Ala Met Ala His Gly Asn Ser>
             a   a   a   a  TRANSLATION OF PRATCH3 [A]  a   a   a   a   >

2916          2926          2936          2946          2956
          *       *     *       *     *       *     *       *     *       *
          ACG CAC CAG AAC TCC CTG GAG GCC CAG AAA AGC AGC GAT ACG CTG ACC
          Thr His Gln Asn Ser Leu Glu Ala Gln Lys Ser Ser Asp Thr Leu Thr>
```

Fig. 4G

```
          a     a    a    a    TRANSLATION OF PRATCH3 [A]       a    a    a    a    >
                2966          2976          2986          2996          3006
             *     *     *     *     *     *     *     *     *     *
          CGA   CAC   CAG   CCA   TTA   CTC   CCG   CTG   CAG   TGC   GGG   GAA   ACG   GAC   TTA   GAT
          Arg   His   Gln   Pro   Leu   Leu   Pro   Leu   Gln   Cys   Gly   Glu   Thr   Asp   Leu   Asp>
          a     a    a    a    TRANSLATION OF PRATCH3 [A]       a    a    a    a    >
                3016          3026          3036          3046
             *     *     *     *     *     *     *     *     *
          CTG   ACC   GTC   CAG   GAA   ACA   GGT   CTG   CAA   GGA   CCT   GTG   GGT   GGA   GAC   CAG
          Leu   Thr   Val   Gln   Glu   Thr   Gly   Leu   Gln   Gly   Pro   Val   Gly   Gly   Asp   Gln>
          a     a    a    a    TRANSLATION OF PRATCH3 [A]       a    a    a    a    >
   3056         3066          3076          3086          3096
     *     *     *     *     *     *     *     *     *     *
   CGG   CCA   GAG   GTG   GAG   GAC   CCT   GAA   GAG   TTG   TCC   CCA   GCA   CTT   GTA   GTG
   Arg   Pro   Glu   Val   Glu   Asp   Pro   Glu   Glu   Leu   Ser   Pro   Ala   Leu   Val   Val>
          a     a    a    a    TRANSLATION OF PRATCH3 [A]       a    a    a    a    >
                3106          3116          3126          3136          3146
             *     *     *     *     *     *     *     *     *
          TCC   AGT   TCA   CAG   AGC   TTT   GTC   ATC   AGT   GGT   GGA   GGC   AGC   ACT   GTT   ACA
          Ser   Ser   Ser   Gln   Ser   Phe   Val   Ile   Ser   Gly   Gly   Gly   Ser   Thr   Val   Thr>
          a     a    a    a    TRANSLATION OF PRATCH3 [A]       a    a    a    a    >
                3156          3166          3176          3186
             *     *     *     *     *     *     *     *     *
          GAA   AAC   GTA   GTG   AAT   TCA   TAAAATGG   AAGGAGAAGA   CTGGGCTAG
          Glu   Asn   Val   Val   Asn   Ser>
                   TRANSLATION OF P        >
```

Fig. 5A

```
Sequence Range: -24 to 3195

-15         -5          6          16         26
    *     *     *     *     *     *     *     *     *     *
GCGGTGGACC GCGTCTTCGC CACA ATG GTC CGG CTC CTC TTG ATT TTC TTC CCA
                          Met Val Arg Leu Leu Leu Ile Phe Phe Pro>
                           a    TRANSLATION OF PHCH4 [A]        a    >

36          46          56          66          76
    *     *     *     *     *     *     *     *     *     *
ATG ATC TTT TTG GAG ATG TCC ATT TTG CCC AGG ATG CCT GAC AGA AAA
Met Ile Phe Leu Glu Met Ser Ile Leu Pro Arg Met Pro Asp Arg Lys>
 a   a   a   a    TRANSLATION OF PHCH4 [A]    a   a   a   a    >

86          96         106         116         126
    *     *     *     *     *     *     *     *     *     *
GTA TTG CTG GCA GGT GCC TCG TCC CAG CGC TCC GTG GCG AGA ATG GAC
Val Leu Leu Ala Gly Ala Ser Ser Gln Arg Ser Val Ala Arg Met Asp>
 a   a   a   a    TRANSLATION OF PHCH4 [A]    a   a   a   a    >

136         146         156         166
       *     *     *     *     *     *     *     *     *
GGA GAT GTC ATC ATC GGA GCC CTC TTC TCA GTC CAT CAC CAG CCT CCA
Gly Asp Val Ile Ile Gly Ala Leu Phe Ser Val His His Gln Pro Pro>
 a   a   a   a    TRANSLATION OF PHCH4 [A]    a   a   a   a    >

176         186         196         206         216
  *     *     *     *     *     *     *     *     *     *
GCC GAG AAG GTA CCC GAA AGG AAG TGT GGG GAG ATC AGG GAA CAG TAT
Ala Glu Lys Val Pro Glu Arg Lys Cys Gly Glu Ile Arg Glu Gln Tyr>
 a   a   a   a    TRANSLATION OF PHCH4 [A]    a   a   a   a    >

226         236         246         256         266
    *     *     *     *     *     *     *     *     *
GGT ATC CAG AGG GTG GAG GCC ATG TTC CAC ACG TTG GAT AAG ATT AAC
Gly Ile Gln Arg Val Glu Ala Met Phe His Thr Leu Asp Lys Ile Asn>
 a   a   a   a    TRANSLATION OF PHCH4 [A]    a   a   a   a    >

276         286         296         306         316
    *     *     *     *     *     *     *     *     *     *
GCG GAC CCG GTG CTC CTG CCC AAC ATC ACT CTG GGC AGT GAG ATC CGG
Ala Asp Pro Val Leu Leu Pro Asn Ile Thr Leu Gly Ser Glu Ile Arg>
 a   a   a   a    TRANSLATION OF PHCH4 [A]    a   a   a   a    >

326         336         346         356         366
    *     *     *     *     *     *     *     *     *     *
GAC TCC TGC TGG CAC TCT TCA GTG GCT CTC GAA CAG AGC ATC GAA TTC
Asp Ser Cys Trp His Ser Ser Val Ala Leu Glu Gln Ser Ile Glu Phe>
 a   a   a   a    TRANSLATION OF PHCH4 [A]    a   a   a   a    >

376         386         396         406
    *     *     *     *     *     *     *     *     *
ATC AGA GAC TCC CTG ATT TCC ATC CGA GAT GAG AAG GAT GGG CTG AAC
Ile Arg Asp Ser Leu Ile Ser Ile Arg Asp Glu Lys Asp Gly Leu Asn>
 a   a   a   a    TRANSLATION OF PHCH4 [A]    a   a   a   a    >

416         426         436         446         456
  *     *     *     *     *     *     *     *     *     *
CGA TGC CTG CCT GAT GGC CAG ACC CTG CCC CCT GGC AGG ACT AAG AAG
Arg Cys Leu Pro Asp Gly Gln Thr Leu Pro Pro Gly Arg Thr Lys Lys>
 a   a   a   a    TRANSLATION OF PHCH4 [A]    a   a   a   a    >
```

Fig. 5B

```
          466           476           486           496           506
           *             *             *             *             *
CCT ATT GCT GGA GTG ATC GGC CCT GGC TCC AGC TCT GTG GCC ATT CAA
Pro Ile Ala Gly Val Ile Gly Pro Gly Ser Ser Ser Val Ala Ile Gln>
 a   a   a   a       TRANSLATION OF PHCH4 [A]       a   a   a   >

516           526           536           546           556
           *             *             *             *             *
GTC CAG AAT CTT CTC CAG CTG TTC GAC ATC CCA CAG ATC GCC TAT TCT
Val Gln Asn Leu Leu Gln Leu Phe Asp Ile Pro Gln Ile Ala Tyr Ser>
 a   a   a   a       TRANSLATION OF PHCH4 [A]       a   a   a   >

566           576           586           596           606
           *             *             *             *             *
GCC ACA AGC ATA GAC CTG AGT GAC AAA ACT TTG TAC AAA TAC TTC CTG
Ala Thr Ser Ile Asp Leu Ser Asp Lys Thr Leu Tyr Lys Tyr Phe Leu>
 a   a   a   a       TRANSLATION OF PHCH4 [A]       a   a   a   >

616           626           636           646
               *             *             *             *
AGG GTT GTC CCT TCT GAC ACT TTG CAG GCA AGG GCC ATG CTT GAC ATA
Arg Val Val Pro Ser Asp Thr Leu Gln Ala Arg Ala Met Leu Asp Ile>
 a   a   a   a       TRANSLATION OF PHCH4 [A]       a   a   a   >

656           666           676           686           696
 *             *             *             *             *
GTC AAA CGT TAC AAT TGG ACC TAT GTC TCT GCA GTC CAC ACG GAA GGG
Val Lys Arg Tyr Asn Trp Thr Tyr Val Ser Ala Val His Thr Glu Gly>
 a   a   a   a       TRANSLATION OF PHCH4 [A]       a   a   a   >

706           716           726           736           746
     *             *             *             *             *
AAT TAT GGG GAG AGC GGA ATG GAC GCT TTC AAA GAG CTG GCT GCC CAG
Asn Tyr Gly Glu Ser Gly Met Asp Ala Phe Lys Glu Leu Ala Ala Gln>
 a   a   a   a       TRANSLATION OF PHCH4 [A]       a   a   a   >

756           766           776           786           796
           *             *             *             *             *
GAA GGC CTC TGT ATC GCC CAT TCT GAC AAA ATC TAC AGC AAC GCT GGG
Glu Gly Leu Cys Ile Ala His Ser Asp Lys Ile Tyr Ser Asn Ala Gly>
 a   a   a   a       TRANSLATION OF PHCH4 [A]       a   a   a   >

806           816           826           836           846
           *             *             *             *             *
GAG AAG AGC TTT GAC CGA CTC TTG CGC AAA CTC CGA GAG AGG CTT CCC
Glu Lys Ser Phe Asp Arg Leu Leu Arg Lys Leu Arg Glu Arg Leu Pro>
 a   a   a   a       TRANSLATION OF PHCH4 [A]       a   a   a   >

856           866           876           886
               *             *             *             *
AAG GCT AGA GTG GTG GTC TGC TTC TGT GAA GGC ATG ACA GTG CGA GGA
Lys Ala Arg Val Val Val Cys Phe Cys Glu Gly Met Thr Val Arg Gly>
 a   a   a   a       TRANSLATION OF PHCH4 [A]       a   a   a   >

896           906           916           926           936
 *             *             *             *             *
CTC CTG AGC GCC ATG CGG CGC CTT GGC GTC GTG GGC GAG TTC TCA CTC
Leu Leu Ser Ala Met Arg Arg Leu Gly Val Val Gly Glu Phe Ser Leu>
 a   a   a   a       TRANSLATION OF PHCH4 [A]       a   a   a   >

```
           ATT GGA AGT GAT GGA TGG GCA GAC AGA GAT GAA GTC ATT GAA GGT TAT
           Ile Gly Ser Asp Gly Trp Ala Asp Arg Asp Glu Val Ile Glu Gly Tyr>
             a   a   a   a     TRANSLATION OF PHCH4 [A]      a   a   a   a  >

996          1006          1016          1026          1036
               *            *    *         *    *         *    *         *
           GAG GTG GAA GCC AAC GGG GGA ATC ACG ATA AAG CTG CAG TCT CCA GAG
           Glu Val Glu Ala Asn Gly Gly Ile Thr Ile Lys Leu Gln Ser Pro Glu>
             a   a   a   a     TRANSLATION OF PHCH4 [A]      a   a   a   a  >

1046         1056          1066          1076         1086
               *    *        *    *         *    *         *    *    *    *
           GTC AGG TCA TTT GAT GAT TAT TTC CTG AAA CTG AGG CTG GAC ACT AAC
           Val Arg Ser Phe Asp Asp Tyr Phe Leu Lys Leu Arg Leu Asp Thr Asn>
             a   a   a   a     TRANSLATION OF PHCH4 [A]      a   a   a   a  >

1096         1106          1116          1126
               *    *        *    *         *    *         *    *
           ACG AGG AAT CCC TGG TTC CCT GAG TTC TGG CAA CAT CGG TTC CAG TGC
           Thr Arg Asn Pro Trp Phe Pro Glu Phe Trp Gln His Arg Phe Gln Cys>
             a   a   a   a     TRANSLATION OF PHCH4 [A]      a   a   a   a  >

1136          1146          1156          1166          1176
      *    *         *    *         *    *         *    *         *    *
           CGC CTT CCA GGA CAC CTT CTG GAA AAT CCC AAC TTT AAA CGA ATC TGC
           Arg Leu Pro Gly His Leu Leu Glu Asn Pro Asn Phe Lys Arg Ile Cys>
             a   a   a   a     TRANSLATION OF PHCH4 [A]      a   a   a   a  >

1186         1196          1206          1216         1226
               *    *        *    *         *    *         *    *    *
           ACA GGC AAT GAA AGC TTA GAA GAA AAC TAT GTC CAG GAC AGT AAG ATG
           Thr Gly Asn Glu Ser Leu Glu Glu Asn Tyr Val Gln Asp Ser Lys Met>
             a   a   a   a     TRANSLATION OF PHCH4 [A]      a   a   a   a  >

1236         1246          1256          1266         1276
               *    *        *    *         *    *         *    *    *
           GGG TTT GTC ATC AAT GCC ATC TAT GCC ATG GCA CAT GGG CTG CAG AAC
           Gly Phe Val Ile Asn Ala Ile Tyr Ala Met Ala His Gly Leu Gln Asn>
             a   a   a   a     TRANSLATION OF PHCH4 [A]      a   a   a   a  >

1286         1296          1306          1316         1326
               *    *        *    *         *    *         *    *    *    *
           ATG CAC CAT GCC CTC TGC CCT GGC CAC GTG GGC CTC TGC GAT GCC ATG
           Met His His Ala Leu Cys Pro Gly His Val Gly Leu Cys Asp Ala Met>
             a   a   a   a     TRANSLATION OF PHCH4 [A]      a   a   a   a  >

1336         1346          1356          1366
               *    *        *    *         *    *         *    *    *
           AAG CCC ATC GAC GGC AGC AAG CTG CTG GAC TTC CTC ATC AAG TCC TCA
           Lys Pro Ile Asp Gly Ser Lys Leu Leu Asp Phe Leu Ile Lys Ser Ser>
             a   a   a   a     TRANSLATION OF PHCH4 [A]      a   a   a   a  >

1376          1386          1396          1406          1416
      *    *         *    *    *    *         *    *         *    *    *
           TTC ATT GGA GTA TCT GGA GAG GAG GTG TGG TTT GAT GAG AAA GGA GAC
           Phe Ile Gly Val Ser Gly Glu Glu Val Trp Phe Asp Glu Lys Gly Asp>
             a   a   a   a     TRANSLATION OF PHCH4 [A]      a   a   a   a  >

1426          1436          1446          1456          1466
      *    *         *    *         *    *         *    *         *    *
           GCT CCT GGA AGG TAT GAT ATC ATG AAT CTG CAG TAC ACT GAA GCT AAT
           Ala Pro Gly Arg Tyr Asp Ile Met Asn Leu Gln Tyr Thr Glu Ala Asn>
```

Fig. 5D

```
              a   a   a   a     TRANSLATION OF PHCH4 [A]     a   a   a   a    >
        1476            1486            1496            1506            1516
         *       *       *       *       *       *       *       *       *       *
    CGC TAT GAC TAT GTG CAC GTT GGA ACC TGG CAT GAA GGA GTG CTG AAC
    Arg Tyr Asp Tyr Val His Val Gly Thr Trp His Glu Gly Val Leu Asn>
              a   a   a   a     TRANSLATION OF PHCH4 [A]     a   a   a   a    >
        1526            1536            1546            1556            1566
         *       *       *       *       *       *       *       *       *       *
    ATT GAT GAT TAC AAA ATC CAG ATG AAC AAG AGT GGA GTG GTG CGG TCT
    Ile Asp Asp Tyr Lys Ile Gln Met Asn Lys Ser Gly Val Val Arg Ser>
              a   a   a   a     TRANSLATION OF PHCH4 [A]     a   a   a   a    >
        1576            1586            1596            1606
         *       *       *       *       *       *       *       *       *
    GTG TGC AGT GAG CCT TGC TTA AAG GGC CAG ATT AAG GTT ATA CGG AAA
    Val Cys Ser Glu Pro Cys Leu Lys Gly Gln Ile Lys Val Ile Arg Lys>
              a   a   a   a     TRANSLATION OF PHCH4 [A]     a   a   a   a    >
 1616            1626            1636            1646            1656
   *       *       *       *       *       *       *       *       *       *
    GGA GAA GTG AGC TGC TGC TGG ATT TGC ACG GCC TGC AAA GAG AAT GAA
    Gly Glu Val Ser Cys Cys Trp Ile Cys Thr Ala Cys Lys Glu Asn Glu>
              a   a   a   a     TRANSLATION OF PHCH4 [A]     a   a   a   a    >
        1666            1676            1686            1696            1706
         *       *       *       *       *       *       *       *       *
    TAT GTG CAA GAT GAG TTC ACC TGC AAA GCT TGT GAC TTG GGA TGG TGG
    Tyr Val Gln Asp Glu Phe Thr Cys Lys Ala Cys Asp Leu Gly Trp Trp>
              a   a   a   a     TRANSLATION OF PHCH4 [A]     a   a   a   a    >
        1716            1726            1736            1746            1756
         *       *       *       *       *       *       *       *       *       *
    CCC AAT GCA GAT CTA ACA GGC TGT GAG CCC ATT CCT GTG CGC TAT CTT
    Pro Asn Ala Asp Leu Thr Gly Cys Glu Pro Ile Pro Val Arg Tyr Leu>
              a   a   a   a     TRANSLATION OF PHCH4 [A]     a   a   a   a    >
        1766            1776            1786            1796            1806
         *       *       *       *       *       *       *       *       *       *
    GAG TGG AGC AAC ATC GAA CCC ATT ATA GCC ATC GCC TTT TCA TGC CTG
    Glu Trp Ser Asn Ile Glu Pro Ile Ile Ala Ile Ala Phe Ser Cys Leu>
              a   a   a   a     TRANSLATION OF PHCH4 [A]     a   a   a   a    >
              1816            1826            1836            1846
               *       *       *       *       *       *       *       *       *
    GGA ATC CTT GTT ACC TTG TTT GTC ACC CTA ATC TTT GTA CTG TAC CGG
    Gly Ile Leu Val Thr Leu Phe Val Thr Leu Ile Phe Val Leu Tyr Arg>
              a   a   a   a     TRANSLATION OF PHCH4 [A]     a   a   a   a    >
 1856            1866            1876            1886            1896
   *       *       *       *       *       *       *       *       *       *
    GAC ACA CCA GTG GTC AAA TCC TCC AGT CGG GAG CTC TGC TAC ATC ATC
    Asp Thr Pro Val Val Lys Ser Ser Ser Arg Glu Leu Cys Tyr Ile Ile>
              a   a   a   a     TRANSLATION OF PHCH4 [A]     a   a   a   a    >
        1906            1916            1926            1936            1946
         *       *       *       *       *       *       *       *       *
    CTA GCT GGC ATC TTC CTT GGT TAT GTG TGC CCA TTC ACT CTC ATT GCC
    Leu Ala Gly Ile Phe Leu Gly Tyr Val Cys Pro Phe Thr Leu Ile Ala>
              a   a   a   a     TRANSLATION OF PHCH4 [A]     a   a   a   a    >
```

Fig. 5E

```
          1956           1966           1976           1986           1996
   *       *       *       *       *       *       *       *       *       *
AAA CCT ACT ACC ACC TCC TGC TAC CTC CAG CGC CTC TTG GTT GGC CTC
Lys Pro Thr Thr Thr Ser Cys Tyr Leu Gln Arg Leu Leu Val Gly Leu>
  a   a   a   a    TRANSLATION OF PHCH4 [A]    a   a   a   a   >

2006           2016          .2026           2036           2046
   *       *       *       *       *       *       *       *       *       *
TCC TCT GCG ATG TGC TAC TCT GCT TTA GTG ACT AAA ACC AAT CGT ATT
Ser Ser Ala Met Cys Tyr Ser Ala Leu Val Thr Lys Thr Asn Arg Ile>
  a   a   a   a    TRANSLATION OF PHCH4 [A]    a   a   a   a   >

2056           2066           2076           2086
   *       *       *       *       *       *       *       *       *
GCA CGC ATC CTG GCT GGC AGC AAG AAG AAG ATC TGC ACC CGG AAG CCC
Ala Arg Ile Leu Ala Gly Ser Lys Lys Lys Ile Cys Thr Arg Lys Pro>
  a   a   a   a    TRANSLATION OF PHCH4 [A]    a   a   a   a   >

2096           2106           2116           2126           2136
   *       *       *       *       *       *       *       *       *       *
AGG TTC ATG AGT GCC TGG GCT CAG GTG ATC ATT GCC TCA ATT CTG ATT
Arg Phe Met Ser Ala Trp Ala Gln Val Ile Ile Ala Ser Ile Leu Ile>
  a   a   a   a    TRANSLATION OF PHCH4 `[A]   a   a   a   a   >

2146           2156           2166           2176           2186
   *       *       *       *       *       *       *       *       *
AGT GTG CAA CTA ACC CTG GTG GTA ACC CTG ATC ATC ATG GAA CCC CCT
Ser Val Gln Leu Thr Leu Val Val Thr Leu Ile Ile Met Glu Pro Pro>
  a   a   a   a    TRANSLATION OF PHCH4 [A]    a   a   a   a   >

2196           2206           2216           2226           2236
   *       *       *       *       *       *       *       *       *       *
ATG CCC ATT CTG TCC TAC CCA AGT ATC AAG GAA GTC TAC CTT ATC TGC
Met Pro Ile Leu Ser Tyr Pro Ser Ile Lys Glu Val Tyr Leu Ile Cys>
  a   a   a   a    TRANSLATION OF PHCH4 [A]    a   a   a   a   >

2246           2256           2266           2276           2286
   *       *       *       *       *       *       *       *       *       *
AAT ACC AGC AAC CTG GGT GTG GTG GCC CCT TTG GGC TAC AAT GGA CTC
Asn Thr Ser Asn Leu Gly Val Val Ala Pro Leu Gly Tyr Asn Gly Leu>
  a   a   a   a    TRANSLATION OF PHCH4 [A]    a   a   a   a   >

2296           2306           2316           2326
   *       *       *       *       *       *       *       *       *
CTC ATC ATG AGC TGT ACC TAC TAT GCC TTC AAG ACC CGC AAC GTG CCC
Leu Ile Met Ser Cys Thr Tyr Tyr Ala Phe Lys Thr Arg Asn Val Pro>
  a   a   a   a    TRANSLATION OF PHCH4 [A]    a   a   a   a   >

2336           2346           2356           2366           2376
   *       *       *       *       *       *       *       *       *       *
GCC AAC TTC AAC GAG GCC AAA TAT ATC GCG TTC ACC ATG TAC ACC ACC
Ala Asn Phe Asn Glu Ala Lys Tyr Ile Ala Phe Thr Met Tyr Thr Thr>
  a   a   a   a    TRANSLATION OF PHCH4 [A]    a   a   a   a   >

2386           2396           2406           2416           2426
   *       *       *       *       *       *       *       *       *
TGT ATC ATC TGG CTA GCT TTT GTG CCC ATT TAC TTT GGG AGC AAC TAC
Cys Ile Ile Trp Leu Ala Phe Val Pro Ile Tyr Phe Gly Ser Asn Tyr>
  a   a   a   a    TRANSLATION OF PHCH4 [A]    a   a   a   a   >

```
        AAG ATC ATC ACA ACT TGC TTT GCA GTG AGT CTC AGT GTA ACA GTG GCT
        Lys Ile Ile Thr Thr Cys Phe Ala Val Ser Leu Ser Val Thr Val Ala>
          a   a   a   a     TRANSLATION OF PHCH4 [A]    a   a   a   a  >

2486        2496        2506        2516        2526
           *    *    *    *    *    *    *    *    *    *
        CTG GGG TGC ATG TTC ACT CCC AAG ATG TAC ATC ATT ATT GCC AAG CCT
        Leu Gly Cys Met Phe Thr Pro Lys Met Tyr Ile Ile Ile Ala Lys Pro>
          a   a   a   a     TRANSLATION OF PHCH4 [A]    a   a   a   a  >

2536        2546        2556        2566
              *    *    *    *    *    *    *    *    *
        GAG AGG AAT ACC ATC GAG GAG GTG CGT TGC AGC ACC GCA GCT CAC GCT
        Glu Arg Asn Thr Ile Glu Glu Val Arg Cys Ser Thr Ala Ala His Ala>
          a   a   a   a     TRANSLATION OF PHCH4 [A]    a   a   a   a  >

2576        2586        2596        2606        2616
     *    *    *    *    *    *    *    *    *    *
        TTC AAG GTG GCT GCC CGG GCC ACG CTG CGC CGC AGC AAC GTC TCC CGC
        Phe Lys Val Ala Ala Arg Ala Thr Leu Arg Arg Ser Asn Val Ser Arg>
          a   a   a   a     TRANSLATION OF PHCH4 [A]    a   a   a   a  >

2626        2636        2646        2656        2666
           *    *    *    *    *    *    *    *    *
        AAG CGG TCC AGC AGC CTT GGA GGC TCC ACG GGA TCC ACC CCC TCC TCC
        Lys Arg Ser Ser Ser Leu Gly Gly Ser Thr Gly Ser Thr Pro Ser Ser>
          a   a   a   a     TRANSLATION OF PHCH4 [A]    a   a   a   a  >

2676        2686        2696        2706        2716
           *    *    *    *    *    *    *    *    *    *
        TCC ATC AGC AGC AAG AGC AAC AGC GAA GAC CCA TTC CCA CAG CCC GAG
        Ser Ile Ser Ser Lys Ser Asn Ser Glu Asp Pro Phe Pro Gln Pro Glu>
          a   a   a   a     TRANSLATION OF PHCH4 [A]    a   a   a   a  >

2726        2736        2746        2756        2766
           *    *    *    *    *    *    *    *    *    *
        AGG CAG AAG CAG CAG CAG CCG CTG GCC CTA ACC CAG CAA GAG CAG CAG
        Arg Gln Lys Gln Gln Gln Pro Leu Ala Leu Thr Gln Gln Glu Gln Gln>
          a   a   a   a     TRANSLATION OF PHCH4 [A]    a   a   a   a  >

2776        2786        2796        2806
              *    *    *    *    *    *    *    *    *
        CAG CAG CCC CTG ACC CTC CCA CAG CAG CAA CGA TCT CAG CAG CAG CCC
        Gln Gln Pro Leu Thr Leu Pro Gln Gln Gln Arg Ser Gln Gln Gln Pro>
          a   a   a   a     TRANSLATION OF PHCH4 [A]    a   a   a   a  >

2816        2826        2836        2846        2856
     *    *    *    *    *    *    *    *    *    *
        AGA TGC AAG CAG AAG GTC ATC TTT GGC AGC GGC ACG GTC ACC TTC TCA
        Arg Cys Lys Gln Lys Val Ile Phe Gly Ser Gly Thr Val Thr Phe Ser>
          a   a   a   a     TRANSLATION OF PHCH4 [A]    a   a   a   a  >

2866        2876        2886        2896        2906
           *    *    *    *    *    *    *    *    *
        CTG AGC TTT GAT GAG CCT CAG AAG AAC GCC ATG GCC CAC GGG AAT TCT
        Leu Ser Phe Asp Glu Pro Gln Lys Asn Ala Met Ala His Gly Asn Ser>
          a   a   a   a     TRANSLATION OF PHCH4 [A]    a   a   a   a  >

2916        2926        2936        2946        2956
           *    *    *    *    *    *    *    *    *    *
        ACG CAC CAG AAC TCC CTG GAG GCC CAG AAA AGC AGC GAT ACG CTG ACC
        Thr His Gln Asn Ser Leu Glu Ala Gln Lys Ser Ser Asp Thr Leu Thr>
```

Fig. 5G

```
       a    a    a    a       TRANSLATION OF PHCH4 [A]         a    a    a    a    >

2966           2976           2986           2996          3006
         *    *         *    *         *    *         *    *         *    *
       CGA CAC CAG CCA TTA CTC CCG CTG CAG TGC GGG GAA ACG GAC TTA GAT
       Arg His Gln Pro Leu Leu Pro Leu Gln Cys Gly Glu Thr Asp Leu Asp>
         a    a    a    a       TRANSLATION OF PHCH4 [A]       a    a    a    a    >

3016           3026           3036           3046
         *    *         *    *         *    *         *    *         *
       CTG ACC GTC CAG GAA ACA GGT CTG CAA GGA CCT GTG GGT GGA GAC CAG
       Leu Thr Val Gln Glu Thr Gly Leu Gln Gly Pro Val Gly Gly Asp Gln>
         a    a    a    a       TRANSLATION OF PHCH4 [A]       a    a    a    a    >

3056           3066           3076           3086           3096
    *    *    *         *    *         *    *         *    *         *    *
  CGG CCA GAG GTG GAG GAC CCT GAA GAG TTG TCC CCA GCA CTT GTA GTG
  Arg Pro Glu Val Glu Asp Pro Glu Glu Leu Ser Pro Ala Leu Val Val>
         a    a    a    a       TRANSLATION OF PHCH4 [A]       a    a    a    a    >

3106           3116           3126           3136           3146
         *    *         *    *         *    *         *    *         *
       TCC AGT TCA CAG AGC TTT GTC ATC AGT GGT GGA GGC AGC ACT GTT ACA
       Ser Ser Ser Gln Ser Phe Val Ile Ser Gly Gly Gly Ser Thr Val Thr>
         a    a    a    a       TRANSLATION OF PHCH4 [A]       a    a    a    a    >

3156           3166           3176           3186
         *    *         *    *         *    *         *    *         *
       GAA AAC GTA GTG AAT TCA T AAAATGG AAGGAGAAGA CTGGGCTAG
       Glu Asn Val Val Asn Ser Xxx>
          TRANSLATION OF PHC  a >
```

— ■ — Quisqualate (mGluR1)
⋯ ▲ ⋯ L-glutamate (mGluR1)
— ● — Quisqualate (mGluR1/CaR)
— × — L-glutamate (mGluR1/CaR)

— ● — CaR
— ▼ — CaR/R1 a) pmGluR1 b) hCaR c) pCH3

CHIMERIC RECEPTORS AND METHODS FOR IDENTIFYING COMPOUNDS ACTIVE AT METABOTROPIC GLUTAMATE RECEPTORS

RELATED APPLICATIONS

This application claims priority to Provisional Application, Forrest H. Fuller et al., U.S. Ser. No. 60/001,526, filed Jul. 26, 1995, entitled CHIMERIC RECEPTORS AND METHODS FOR IDENTIFYING COMPOUNDS ACTIVE AT METABOTROPIC GLUTAMATE RECEPTORS AND THE USE OF SUCH COMPOUNDS IN THE TREATMENT OF NEUROLOGICAL DISORDERS AND DISEASES, which is incorporated herein by reference in its entirety including drawings.

FIELD OF THE INVENTION

The present invention relates to chimeric receptors containing one or more regions homologous to a metabotropic glutamate receptor and one or more regions homologous to a calcium receptor.

BACKGROUND OF THE INVENTION

The following description provides a summary of information relevant to the present invention. It is not an admission that any of the information provided herein is prior art to the presently claimed invention, nor that any of the publications specifically or implicitly referenced are prior art to that invention.

Glutamate is the major excitatory neurotransmitter in the mammalian brain. Glutamate produces its effects on central neurons by binding to and thereby activating cell surface receptors. These receptors have been subdivided into two major classes, the ionotropic and metabotropic glutamate receptors, based on the structural features of the receptor proteins, the means by which the receptors transduce signals into the cell, and pharmacological profiles.

The ionotropic glutamate receptors (iGluRs) are ligand-gated ion channels that, upon binding glutamate, open to allow the selective influx of certain monovalent and divalent cations, thereby depolarizing the cell membrane. In addition, certain iGluRs with relatively high calcium permeability can activate a variety of calcium-dependent intracellular processes. These receptors are multisubunit protein complexes that may be homomeric or heteromeric in nature. The various iGluR subunits all share common structural motifs, including a relatively large amino-terminal extracellular domain (ECD), followed by a multiple transmembrane domain (TMD) comprising two membrane-spanning regions (TMs), a second smaller intracellular loop, and a third TM, before terminating with an intracellular carboxy-terminal domain (CT). Historically the iGluRs were first subdivided pharmacologically into three classes based on preferential activation by the agonists alpha-amino-3-hydroxy-5-methyl-isoxazole- 4-propionic acid (AMPA), kainate (KA), and N-methyl-D-aspartate (NMDA). Later, molecular cloning studies coupled with additional pharmacological studies revealed a greater diversity of iGluRs, in that multiple subtypes of AMPA, KA and NMDA receptors are expressed in the mammalian CNS (Hollman and Heinemann, *Ann. Rev. Neurosci.* 7:31, 1994).

The metabotropic glutamate receptors (mGluRs) are G protein-coupled receptors capable of activating a variety of intracellular second messenger systems following the binding of glutamate or other potent agonists including quisqualate and 1-aminocyclopentane-1,3-dicarboxylic acid (trans-ACPD) (Schoepp et al., *Trends Pharmacol. Sci.* 11:508, 1990; Schoepp and Conn, *Trends Pharmacol. Sci.* 14:13, 1993).

Activation of different metabotropic glutamate receptor subtypes in situ elicits one or more of the following responses: activation of phospholipase C, increases in phosphoinositide (PI) hydrolysis, intracellular calcium release, activation of phospholipase D, activation or inhibition of adenylyl cyclase, increases and decreases in the formation of cyclic adenosine monophosphate (cAMP), activation of guanylyl cyclase, increases in the formation of cyclic guanosine monophosphate (cGMP), activation of phospholipase $A_2$, increases in arachidonic acid release, and increases or decreases in the activity of voltage- and ligand-gated ion channels (Schoepp and Conn, *Trends Pharmacol. Sci.* 14:13, 1993; Schoepp, *Neurochem. Int.* 24:439, 1994; Pin and Duvoisin, *Neuropharmacology* 34:1, 1995).

Thus far, eight distinct mGluR subtypes have been isolated via molecular cloning, and named mGluR1 to mGluR8 according to the order in which they were discovered (Nakanishi, *Neuron* 13:1031, 1994, Pin and Duvoisin, *Neuropharmacology* 34:1, 1995; Knopfel et al., *J. Med. Chem.* 38:1417, 1995). Further diversity occurs through the expression of alternatively spliced forms of certain mGluR subtypes (Pin et al., *PNAS* 89:10331, 1992; Minakami et al., *BBRC* 199:1136, 1994). All of the mGluRs are structurally similar, in that they are single subunit membrane proteins possessing a large amino-terminal extracellular domain (ECD) followed by seven putative transmembrane domain (7TMD) comprising seven putative membrane spanning helices connected by three intracellular and three extracellular loops, and an intracellular carboxy-terminal domain of variable length (cytoplasmic tail) (CT) (see, Schematic FIG. 1a).

The eight mGluRs have been subdivided into three groups based on amino acid sequence identities, the second messenger systems they utilize, and pharmacological characteristics (Nakanishi, *Neuron* 13:1031, 1994; Pine and Duvoisin, *Neuropharmacology* 34:1, 1995; Knopfel et al., *J. Med. Chem.* 38:1417, 1995). The amino acid identity between mGluRs within a given group is approximately 70% but drops to about 40% between mGluRs in different groups. For mGluRs in the same group, this relatedness is roughly paralleled by similarities in signal transduction mechanisms and pharmacological characteristics.

The Group I mGluRs comprise mGluR1, mGluR5 and their alternatively spliced variants. The binding of agonists to these receptors results in the activation of phospholipase C and the subsequent mobilization of intracellular calcium. For example, Xenopus oocytes expressing recombinant mGluR1 receptors have been utilized to demonstrate this effect indirectly by electrophysiological means (Masu et al., *Nature* 349:760, 1991; Pin et al., *PNAS* 89:10331, 1992). Similar results were achieved with oocytes expressing recombinant mGluR5 receptors (Abe et al., *J. Biol. Chem.* 267:13361, 1992; Minakami et al., *BBRC* 199:1136, 1994). Alternatively, agonist activation of recombinant mGluR1 receptors expressed in Chinese hamster ovary (CHO) cells stimulated PI hydrolysis, cAMP formation, and arachidonic acid release as measured by standard biochemical assays (Aramori and Nakanishi, *Neuron* 8:757, 1992). In comparison, activation of mGluR5 receptors expressed in CHO cells stimulated PI hydrolysis and subsequent intracellular calcium transients but no stimulation of cAMP formation or arachidonic acid release was observed (Abe et al., *J. Biol. Chem.* 267:13361, 1992). The agonist potency profile for Group I mGluRs is quisqualate>glutamate= ibotenate>(2S,1'S,2'S) -2-carboxycyclopropyl)glycine (L-CCG-I)>(1S,3R)-1-aminocyclopentane-1,3-dicarboxylic acid (ACPD). Quisqualate is relatively selective for Group I receptors, as compared to Group II and Group III mGluRs, but it also potently activates ionotropic AMPA receptors (Pin and Duvoisin, Neuropharmacology, 34:1, Knopfel et al., J. Med. Chem. 38:1417, 1995).

The Group II mGluRs include mGluR2 and mGluR3. Activation of these receptors as expressed in CHO cells inhibits adenylyl cyclase activity via the inhibitory G protein, $G_i$, in a pertussis toxin-sensitive fashion (Tanabe et al., Neuron 8:169, 1992; Tanabe et al., Neurosci. 13:1372, 1993). The agonist potency profile for Group II receptors is L-CCG-I>glutamate>ACPD>ibotenate>quisqualate. Preliminary studies suggest that L-CCG-I and (2S,1'R,2'R,3'R)-2-(2,3-dicarboxycyclopropyl)glycine (DCG-IV) are both relatively selective agonists for the Group II receptors (Knopfel et al., J. Med. Chem. 38:1417, 1995).

The Group III mGluRs include mGluR4, mGluR6, mGluR7 and mGluR8. Like the Group II receptors these mGluRs are negatively coupled to adenylate cyclase to inhibit intracellular cAMP accumulation in a pertussis toxin-sensitive fashion when expressed in CHO cells (Tanabe et al., J. Neurosci. 13:1372, 1993; Nakajima et al., J. Biol. Chem. 268:11868, 1993; Okamoto et al., J. Biol. Chem. 269:1231, 1994; Duvoisin et al., J. Neurosci. 15:3075, 1995). As a group, their agonist potency profile is (S)-2-amino-4-phosphonobutyric acid (L-AP4) >glutamate>ACPD>quisqualate, but mGluR8 may differ slightly with glutamate being more potent than L-AP4 (Knopfel et al., J. Med. Chem. 38:1417, 1995; Duvoisin et al., J. Neurosci. 15: 3075, 1995). Both L-AP4 and (S)-serine-O-phosphate (L-SOP) are relatively selective agonists for the Group III receptors.

Finally, the eight mGluR subtypes have unique patterns of expression within the mammalian CNS that in many instances are overlapping (Masu et al., Nature 349:760, 1991; Martin et al., Neuron 9:259, 1992; Ohishi et al., Neurosci. 53:1009, 1993; Tanabe et al., J. Neurosci. 13:1372; Ohishi et al., Neuron 13:55, 1994, Abe et al., J. Biol. Chem. 267:13361, 1992; Nakajima et al., J. Biol. Chem. 268:11868, 1993; Okamoto et al., J. Biol. Chem. 269:1231, 1994; Duvoisin et al., J. Neurosci. 15:3075, 1995). As a result certain neurons may express only one particular mGluR subtype, while other neurons may express multiple subtypes that may be localized to similar and/or different locations on the cell (i.e., postsynaptic dendrites and/or cell bodies versus presynaptic axon terminals). Therefore, the functional consequences of mGluR activation on a given neuron will depend on the particular mGluRs being expressed; the receptors' affinities for glutamate and the concentrations of glutamate the cell is exposed to; the signal transduction pathways activated by the receptors; and the locations of the receptors on the cell. A further level of complexity may be introduced by multiple interactions between mGluR expressing neurons in a given brain region. As a result of these complexities, and the lack of subtype-specific mGluR agonists and antagonists, the roles of particular mGluRs in physiological and pathophysiological processes affecting neuronal function are not well defined. Still, work with the available agonists and antagonists have yielded some general insights about the Group I mGluRs as compared to the Group II and Group III mGluRs.

Attempts at elucidating the physiological roles of Group I mGluRs suggest that activation of these receptors elicits neuronal excitation. Various studies have demonstrated that ACPD can produce postsynaptic excitation upon application to neurons in the hippocampus, cerebral cortex, cerebellum, and thalamus as well as other brain regions. Evidence indicates that this excitation is due to direct activation of postsynaptic mGluRs, but it has also been suggested to be mediated by activation of presynaptic mGluRs resulting in increased neurotransmitter release (Baskys, Trends Pharmacol. Sci. 15:92, 1992; Schoepp, Neurochem. Int. 24:439, 1994; Pin and Duvoisin, Neuropharmacology 34:1). Pharmacological experiments implicate Group I mGluRs as the mediators of this excitation. The effect of ACPD can be reproduced by low concentrations of quisqualate in the presence of iGluR antagonists (Hu and Storm, Brain Res. 568:339, 1991; Greene et al. Eur. J. Pharmacol. 226:279, 1992), and two phenylglycine compounds known to activate mGluR1, (S)-3-hydroxyphenylglycine ((S)-3HPG) and (S)-3,5-dihydroxyphenylglycine ((S)-DHPG), also produce the excitation (Watkins and Collingridge, Trends Pharmacol. Sci. 15:333, 1994). In addition, the excitation can be blocked by (S)-4-carboxyphenylglycine ((S)-4CPG), (S)-4-carboxy-3-hydroxyphenylglycine ((S)-4C3HPG) and (+)-alphamethyl- 4-carboxyphenylglycine ((+)-MCPG), compounds known to be mGluR1 antagonists (Eaton et al., Eur. J. Pharmacol. 244:195, 1993; Watkins and Collingridge, Trends Pharmacol. Sci. 15:333, 1994).

Other studies examining the physiological roles of mGluRs indicate that activation of presynaptic mGluRs can block both excitatory and inhibitory synaptic transmission by inhibiting neurotransmitter release (Pin and Duvoisin, Neuropharmacology 34:1). Presynaptic blockade of excitatory synaptic transmission by ACPD has been observed on neurons in the visual cortex, cerebellum, hippocampus, striatum and amygdala (Pin et al., Curr. Drugs: Neurodegenerative Disorders 1:111, 1993), while similar blockade of inhibitory synaptic transmission has been demonstrated in the striatum and olfactory bulb (Calabresi et al., Neurosci. Lett. 139:41, 1992; Hayashi et al., Nature 366:687, 1993). Multiple pieces of evidence suggest that Group II mGluRs mediate this presynaptic inhibition. Group II mGluRs are strongly coupled to inhibition of adenylyl cyclase, like alpha$_2$-adrenergic and SHT$_{1A}$-serotonergic receptors which are known to mediate presynaptic inhibition of neurotransmitter release in other neurons. The inhibitory effects of ACPD can also be mimicked by L-CCG-I and DCG-IV, which are selective agonists at Group II mGluRs (Hayashi et al., Nature 366:687, 1993; Jane et al., Br. J. Pharmacol. 112:809, 1994). Moreover, it has been demonstrated that activation of mGluR2 can strongly inhibit presynaptic, N-type calcium channel activity when the receptor is expressed in sympathetic neurons (Ikeda et al., Neuron 14:1029, 1995), and inactivation of these channels is known to inhibit neurotransmitter release. Finally, it has been observed that L-CCG-I, at concentrations selective for Group II mGluRs, inhibits the depolarization-evoked release of $^3$H-aspartate from rat striatal slices (Lombardi et al., Br. J. Pharmacol. 110:1407, 1993). Evidence for physiological effects of Group II mGluR activation at the postsynaptic level is limited. However, one study suggests that postsynaptic actions of L-CCG-I can inhibit NMDA receptor activation in cultured mesencephalic neurons (Ambrosini et al., Mol. Pharmacol. 47:1057, 1995).

Physiological studies have demonstrated that L-AP4 can also inhibit excitatory synaptic transmission on a variety of CNS neurons. Included are neurons in the cortex, hippocampus, amygdala, olfactory bulb and spinal cord (Koerner and Johnson, Excitatory Amino Acid Receptors; Design of Agonists and Antagonists p. 308, 1992; Pin et al., Curr. Drugs: Neurodegenerative Disorders 1:111, 1993). The accumulated evidence indicates that the inhibition is mediated by activation of presynaptic mGluRs. Since the effects of L-AP4 can be mimicked by L-SOP, and these two agonists are selective for Group III mGluRs, members of this mGluR group are implicated as the mediators of the presynaptic inhibition (Schoepp, Neurochem. Int. 24:439, 1994; Pin and Duvoisin, Neuropharmacology 34:1). In olfactory bulb neurons it has been demonstrated that L-AP4 activation of mGluRs inhibits presynaptic calcium currents (Trombley and Westbrook, J. Neurosci. 12:2043, 1992). It is therefore likely that the mechanism of presynaptic inhibition produced by activation of Group III mGluRs is similar to that for Group II mGluRs, i.e., blockade of N-type calcium channels and inhibition of neurotransmitter release. L-AP4 is also known to act postsynaptically to hyperpolarize ON bipolar cells in the retina. It has been suggested that this action may be due to activation of a mGluR, which is coupled to the cGMP phosphodiesterase in these cells (Schoepp, Neurochem. Int. 24:439, 1994; Pin and Duvoisin, Neuropharmacology 34:1).

Metabotropic glutamate receptor activation studies using agonists, antagonists and recombinant vertebrate cell lines expressing mGluRs have been used to evaluate the cellular effects of the stimulation and the inhibition of different metabotropic glutamate receptors. For example, agonist stimulation of mGluR1 expressed in Xenopus oocytes demonstrated coupling of receptor activation to mobilization of intracellular calcium as assessed indirectly using electrophysiology techniques (Masu et al., Nature 349:760–765, 1991). Agonist stimulation of mGluR1 expressed in CHO cells stimulated PI hydrolysis, cAMP formation and arachidonic acid release (Aramori and Nakanishi, Neuron 8:757–765, 1992). Agonist stimulation of mGluR5 expressed in CHO cells also stimulated PI hydrolysis which was shown to be associated with a transient increase in cytosolic calcium as assessed by loading cells with the fluorescent calcium chelator fura-2 (Abe et al., J. Biol. Chem. 267:13361–13368, 1992). Agonist-induced activation of mGluR1 and mGluR5 induced PI hydrolysis in CHO cells was not antagonized by AP3 and AP4, which are both antagonists of glutamate-stimulated PI hydrolysis in situ (Nicoletti et al., Proc. Natl. Acad. Sci. USA 833:1931–1935, 1986; Schoepp and Johnson, J. Neurochem. 53:273–278, 1989). Agonist stimulation of CHO cells expressing mGluR2 (Tanabe et al., Neuron 8:169–179, 1992) or mGluR7 (Okamoto et al., J. Biol. Chem. 269:1231–1236, 1994) resulted in receptor-mediated inhibition of cAMP formation and also confirmed the ligand specificity previously observed in situ. Studies using agonists were also carried out in conjunction with site-directed mutagenesis to reveal specific amino acids playing important roles in glutamate binding (O'Hara et al., Neuron 11:41–52, 1993).

Metabotropic glutamate receptors (mGluRs) have been implicated in a variety of neurological pathologies including stroke, head trauma, spinal cord injury, epilepsy, ischemia, hypoglycemia, anoxia, and neurodegenerative diseases such as Alzheimer's disease (Schoepp and Conn, Trends Pharmacol. Sci. 14:13, 1993; Cunningham et al., Life Sci. 54: 135, 1994; Pin et al., Neuropharmacology 34:1, 1995; Knopfel et al., J. Med. Chem. 38:1417, 1995;). A role for metabotropic glutamate receptors in nociception and analgesia has also been demonstrated (Meller et al., Neuroreport 4:879, 1993). Metabotropic glutamate receptors have also been shown to be required for the induction of hippocampal long-term potentiation and cerebellar long-term depression (Bashir et al., Nature 363:347, 1993; Bortolotto et al., Nature 368:740, 1994; Aiba et. al. Cell 79: 365 and Cell 79: 377, 1994).

Metabotropic glutamate receptor agonists have been reported to have effects on various physiological activities. For example, trans-ACPD was reported to possess both proconvulsant and anticonvulsant effects (Zheng and Gallagher, Neurosci. Lett. 125:147, 1991; Sacaan and Schoepp, Neurosci. Lett. 139:77, 1992; Taschenberger et al., Neuroreport 3:629, 1992; Sheardown, Neuroreport 3:916, 1992), and neuroprotective effects in vitro and in vivo (Pizzi et al., J. Neurochem. 61:683, 1993; Koh et al., Proc. Natl. Acad. Sci. USA 88:9431, 1991; Birrell et al., Neuropharmacol. 32:1351, 1993; Siliprandi et al., Eur. J. Pharmacol. 219:173, 1992; Chiamulera et al., Eur. J. Pharmacol. 216:335, 1992). The metabotropic glutamate receptor antagonist L-AP3 was shown to protect against hypoxic injury in vitro (Opitz and Reymann, Neuroreport 2:455, 1991). A subsequent study reported that trans-ACPD produced neuroprotection which was antagonized by L-AP3 (Opitz and Reymann, Neuropharmacol. 32:103, 1993). (5)-4C3HPG was shown to protect against audiogenic seizures in DBA/2 mice (Thomasen et al., J. Neurochem. 62:2492, 1994). Other modulatory effects expected of metabotropic glutamate receptor modulators include synaptic transmission, neuronal death, neuronal development, synaptic plasticity, spatial learning, olfactory memory, central control of cardiac activity, waking, control of movements, and control of vestibule ocular reflex (for reviews, see Nakanishi, Neuron 13:1031–37, 1994; Pin et al., Neuropharmacology 34:1, 1995; Knopfel et al., J. Med. Chem. 38:1417, 1995).

The structures of mGluR-active molecules currently known in the art are limited to amino acids which appear to act by binding at the glutamate binding site (Pin, et al, Neuropharmacology 34:1, 1995; Knopfel et al., J. Med. Chem. 38:1418). This limits the range of pharmacological properties and potential therapeutic utilities of such compounds. Furthermore, the range of pharmacological specificities associated with these mGluR-active molecules does not allow for complete discrimination between different subtypes of metabotropic glutamate receptors (Pin et al., Neuropharmacology 34:1, 1995 and Knopfel et al., J. Med. Chem. 38:1418). Rapid progress in the field of mGluR-active molecules cannot be made until more potent and more selective mGluR agonists, antagonists and modulators are discovered (Pin et al., Neuropharmacology 34:1, 1995; Knopfel et al., J. Med. Chem. 38:1418). Indeed, no mGluR-active molecules are presently under clinical development. High throughput functional screening of compounds and compound libraries using cell lines expressing individual mGluRs represents an important approach to identifying such novel compounds (Knopfel et al., J. Med. Chem. 38:1418).

Several laboratories have constructed cell lines expressing metabotropic glutamate receptors which appear to function appropriately (Abe et al., J. Biol. Chem. 267:13361, 1992; Tanabe et al., Neuron 8:169, 1992; Aramori and Nakanishi, Neuron 8:757, 1992, Nakanishi, Science 258:597, 1992; Thomsen et al., Brain Res. 619:22, 1992; Thomsen et al., Eur. J. Pharmacol. 227:361, 1992; O'Hara et al., Neuron 11:41, 1993; Nakjima et al., J. Biol. Chem. 268:11868, 1993; Tanabe et al., J. Neurosci. 13:1372, 1993; Saugstad et al., Mol. Pharmacol. 45:367, 1994; Okamoto et al., J. Biol. Chem. 269:1231, 1994; Gabellini et al., Neurochem. Int. 24:533, 1994; Lin et al., Soc. Neurosci. Abstr. 20:468, 1994; Flor et al., Soc. Neurosci. Abstr. 20:468, 1994; Flor et al., Neuropharmacology 34:149, 1994). Other reports have noted that expression of functional mGluR expressing cell lines is not predictable. For example, Tanabe et al., (Neuron 8:169, 1992) were unable to demonstrate functional expression of mGluR3 and mGluR4, and noted difficulty obtaining expression of native mGluR1 in CHO cells. Gabellini et al., (Neurochem. Int. 24:533, 1994) also noted difficulties with mGluR1 expression in HEK 293 cells and it is possible that some of these difficulties may be due to desensitization characteristics of these receptors. Furthermore, screening methodologies useful for identification of compounds active at Class I mGluRs are not readily amenable to identification of compounds active at class II and III mGluRs and vice versa due to the differences in second messenger coupling. Finally, mGluRs have been noted to rapidly desensitize upon agonist stimulation which may adversely affect the viability of cell lines expressing these receptors and makes the use of native mGluRs for screening difficult.

Different G-protein coupled receptors exhibit differential ligand affinities and coupling to second messengers. G-protein coupled receptors all have a similar structure: an N-terminal extracellular domain (ECD), a seven-transmembrane domain (7TMD) comprising seven membrane spanning helices and therefore defining three intracellular and three extracellular loops, and a cytoplasmic tail (CT), but differ in the exact sequences comprising each region. These sequence differences are thought to provide the specificity of receptor interactions with ligands of different chemical compositions and receptor interaction with different G-proteins. Construction of chimeric receptors in which small peptide segments from related receptors are exchanged using recombinant DNA techniques has proven a useful technique to assess the participation of different sequence regions in determining this specificity. For example, exchanging the third intracellular loops between various adrenergic, muscarinic acetylcholine and angiotensin receptors results in conversion of G-protein coupling specificity. Thus, receptors whose activation normally results in inhibition or activation of adenylate cyclase can be converted to receptors with the same or similar ligand binding properties but whose activation leads to stimulation of phospholipase-C and vice versa (Kobilka et al., Science 240:1310, 1988; Wess et al., FEBS Lett. 258:133, 1989; Cotecchia et al., Proc. Nat'l. Acad. Sci. U.S.A. 87:2896, 1990; Lechleiter et al., EMBO J. 9:4381, 1990; Wess et al., Mol. Pharmacol. 38:517, 1990; Wong et al., J. Biol. Chem. 265:6219, 1990; Cotecchia et al., J. Biol. Chem. 267:1633, 1992; Wang et al., J. Biol. Chem. 270:16677, 1995). In these receptors which share the third intracellular loop plays an important role in determining the specificity of G-protein coupling. While such experiments indicate that the third intracellular loop plays an important role in determining the specificity of G protein coupling in these related receptors, they have failed to identify any specific amino acid sequence motif which is responsible. In addition, the third intracellular loop has been shown to be at least partly responsible for desensitization of such receptors (Okamoto et al., Cell 67:723, 1991; Liggett et al., J. Biol. Chem. 267:4740, 1992).

Metabotropic glutamate receptors are related to other G-protein coupled receptors in overall topology, but not in specific amino acid sequence. An unusual feature of mGluRs is their very large ECDs (ca. 600 amino acids). In many other G-protein coupled receptors, ligand binding takes place within the 7TMD. However, the large ECD of each mGluR is thought to provide the ligand binding determinants (Nakanishi, Science 258:597, 1992; O'Hara et al., Neuron 11:41, 1993; Shigemoto et al., Neuron 12:1245, 1994). Chimeric mGluRs in which the ECDs of mGluRs with different ligand affinities and different G-protein coupling are exchanged have been used to demonstrate that the ECD of mGluRs defines ligand specificity but not G-protein specificity (Takahashi et al., J. Bio. Chem. 268:19341, 1993). Also unlike other G-protein coupled receptors in which the third intracellular loop is variable in size and sequence, the third intracellular loops of mGluRs are small and extremely well conserved (Brown E. M. et al., Nature 366:575, 1993). Chimeric mGluRs have been prepared in which the second intracellular loops and/or cytoplasmic tails were exchanged (Pin et al., EMBO J. 13:342). These experiments lead the investigators to conclude that unlike most other G-protein coupled receptors, "both the C-terminal end of the second intracellular loop and the segment located downstream of the seventh transmembrane domain are necessary for the specific activation of phospholipase-C by mGluR1c" and to suggest that the second intracellular loop of mGluRs plays the role of the third intracellular loop of other G-protein coupled receptors.

Naturally occurring mRNA splice variants have been noted to produce prostaglandin E3 (EP3) receptors with essentially identical ligand binding properties but which preferentially activate different second messenger pathways (differential G-protein coupling) and which exhibit different desensitization properties (Namba et al., Nature 365:166, 1993; Sgimoto et al., J. Biol. Chem. 268:2712, 1993; Negishi et al., J. Biol. Chem. 268:9517, 1993). These variant receptor isoforms differ only in their cytoplasmic tails. The isoforms with the longer tails couple efficiently to phospholipase-C while those with the shorter tails do not. However, analyses of naturally occurring mRNA splice variants of mGluR1 and mGluR5 have indicated that their long cytoplasmic tails may not be directly involved in G protein coupling (Pin et al., Proc. Nat'l. Acad. Sci. U.S.A. 89:10331, 1992; Joly et al., J. Neuroscience 15:3970, 1995). In fact, Pin et al., (supra) have stated that "The very long C-terminal domain found only in PLC-coupled mGluRs (mGluR1 and 5) is, however, probably not involved in the specific interaction with PLC-activating G proteins."

Recently, calcium receptor has been described (Brown E. M. et al., Nature 366:575, 1993; Riccardi D., et al., Proc. Nat'l. Acad. Sci. USA 92:131–135, 1995; Garrett J. E., et al., J. Biol. Chem. 31:12919–12925, 1995). This CaR is the only known receptor which exhibits significant sequence homology with mGluRs except for other mGluRs. The CaR exhibits about ~25% sequence homology (amino acid identities) to any one mGluR while mGluRs are >40% homologous (amino acid identities) to one another. The CaR is structurally related to mGluRs having a large ECD which has been implicated in receptor function and probable ligand binding (Brown E. M. et al., Nature 366:575, 1993; Pollak, M. R., et al., Cell 75:1297–1303, 1993). This similarity of structure does not confer close similarity in ligand binding specificity since the native ligand for the CaR is the inorganic ion, $Ca^{2+}$, and glutamate does not modulate CaR activity. The CaR also has a large cytoplasmic tail and is coupled to the stimulation of phospholipase-C. Thus, the CaR is structurally and functionally more related to mGluR1 and 5 than to other mGluRs. Pin et al., (EMBO J. 13:342, 1994) have noted that certain amino acids are conserved within the intracellular loops of mGluRs which couple to phospholipase-C and different amino acids are conserved in these same positions within the intracellular loops of mGluRs which couple to the inhibition of adenylate cyclase. Intracellular loops 1 and 3 are the most highly conserved sequences between mGluRs and the CaR (Brown E. M. et al., Nature 366:575, 1993), but only about half of these particular amino acids are found in the corresponding position of the CaR and only one of these is actually the amino acid predicted for a receptor which couples to phospholipase-C. Thus, sequence conservation between CaRs and mGluRs appears to be consistent mostly with conservation of structural domains involved in ligand binding and G-protein coupling and does not provide evidence for specific sequence motifs within intracellular regions predictive of G-protein coupling specificity. Cell lines expressing CaRs have been obtained and their use to identify compounds which modulate the activity of CaRs disclosed (pending U.S. patent application Ser. No. 08/353,784, filed Dec. 9, 1994, hereby incorporated by reference herein).

An ideal screening procedure for identifying molecules specifically affecting the activity of different mGluRs would provide cell lines expressing each functional mGluR in such a manner that each was coupled to the same second messenger system and amenable to high throughput screening.

None of the references mentioned herein are admitted to be prior art to the claims.

SUMMARY OF THE INVENTION

The present invention concerns (1) chimeric receptor proteins having sequences from metabotropic glutamate receptors and calcium receptors, and fragments of metabotropic glutamate receptors, calcium receptors, and chimeric receptors; (2) nucleic acids encoding such chimeric receptor proteins and fragments; (3) uses of such receptor proteins, fragments and nucleic acids; (4) cell lines expressing such nucleic acids; (5) methods of screening for compounds that bind to or modulate the activity of metabotropic glutamate receptors or calcium receptors using such chimeric receptor proteins and fragments; (6) compounds for modulating metabotropic glutamate receptors or calcium receptors identified by such methods of screening; (7) methods for modulating metabotropic glutamate receptors or calcium receptors utilizing such compounds; and (8) methods of treating neurological disorders using such compounds.

A preferred use of the compounds and methods of the present invention is to screen for compounds which modulate metabotropic glutamate receptor activity and to use such compounds to aid in the treatment of neurological diseases or disorders.

As described in the Background of the Invention above, metabotropic glutamate receptors and calcium receptors have similar structures. Both types of receptors have an extracellular domain (ECD), a seven transmembrane domain (7TMD) and an intracellular cytoplasmic tail (CT). Thus, in the chimeric receptors of the present invention, a portion of the sequence of the receptor is the same as or homologous to a portion of the sequence of an mGluR and a portion of the sequence is the same as or homologous to a portion of the sequence of a CaR. For example, the chimeric receptor can consist of the ECD of an mGluR and the 7TMD and CT of a CaR. Likewise, a chimeric receptor may include the ECD and 7TMD of an mGluR and the CT of a CaR. Other combinations of mGluR and CaR domains or portions of domains may also be constructed and utilized.

These chimeric receptors are of interest, in part, because they allow the coupling of certain functional aspects of an mGluR with certain functional aspects of a CaR. Thus, experiments have shown that ligands known in the art which are agonists or antagonists on a native mGluR also exhibit such activities on chimeric receptors in which the extracellular domain is from the mGluR. Similarly, experiments have shown that ligands known in the art which modulate mGluRs act on chimeric receptors in which the extracellular domain and the 7TMD are from an mGluR. In both of these cases, it is expected that other ligands which modulate mGluR activity will also act on these types of chimeric receptors.

The use of mGluRs for screening for mGluR active compounds has been complicated by a number of factors including a rapid desensitization of the receptor upon ligand binding/activation and difficulties in stably expressing the receptors in recombinant vertebrate cells (see, for example, FIG. 8B and also published PCT Patent Application). Certain of the chimeric receptors of the present invention can be utilized to overcome these technical difficulties and provide much improved screening methods by utilizing the more robust aspects of calcium receptors. For example, by coupling the 7TMD and the CT of the CaR with the extracellular domain of an mGluR, or the CT of the CaR to the ECD and 7TMD of the mGluR, the mGluR extracellular domain has the benefit of the Gq coupling property of a CaR as well as the improved property of a lack of rapid densensitization (see, for example, FIG. 8C). Thus, such a chimeric receptor has the ligand binding and activation properties similar to those of a native mGluR but having the improved second messenger coupling similar to a CaR. Therefore, the chimeric receptor simplifies and enables efficient, practical, and reproducible functional screens to identify mGluR active molecules.

For these novel chimeric receptors, not only is the combination of mGluR and CaR sequences in a chimeric receptor novel, but also the successful coupling of the activities is unexpected. Previously, such coupling had only been accomplished using portions of receptors with closely related sequences. In this case the sequence identity between metabotropic glutamate receptors and calcium receptors is only about 19–25%, and the two types of receptors share only a 25–30% sequence similarity (Brown et al., Nature 366:575, 1993).

It is recognized that the three domains described above are made up of sub-domains, for example, ligand binding sites and G protein coupling sites. Therefore, for some applications it is not necessary to include in a chimeric receptor a complete domain from a particular receptor in order to have the desired activity. For example, only the ligand binding site from an mGluR can be incorporated in a chimeric receptor in which most or all of the remainder of the sequence is homologous to a CaR. Likewise, in a chimeric receptor, one of the cytoplasmic loops of the 7TMD can be homologous to a loop sequence of an mGluR and substantially the remainder of the sequence of the receptor can be homologous to a CaR, or conversely, one of the cytoplasmic loops can be homologous to a loop sequence of a CaR and substantially the remainder of the sequence of the receptor can be homologous to an mGluR.

Thus, in a first aspect the invention features a composition including a chimeric receptor which has an extracellular domain, a seven transmembrane domain, and an intracellular cytoplasmic tail domain. The chimeric receptor has a sequence of at least 6 contiguous amino which is homologous to a sequence of a metabotropic glutamate receptor and a sequence of at least 6 contiguous amino acids which is homologous to a sequence of a calcium receptor.

In preferred embodiments, at least one domain is homologous to a domain of a metabotropic glutamate receptor, or at least one domain is homologous to a domain of a calcium receptor. In particular, this includes chimeric receptors having a domain homologous to a metabotropic glutamate receptor and a domain homologous to a calcium receptor.

Also in preferred embodiments, the chimeric receptor has two domains from a metabotropic glutamate receptor and one domain from a calcium receptor, or two domains from a calcium receptor and one domain from a metabotropic glutamate receptor. This includes each of the possible combinations of the three domains. For example, in a more preferred embodiment, the chimeric receptor has one domain homologous to the extracellular domain of a metabotropic glutamate receptor, one domain homologous to the seven transmembrane domain of a metabotropic glutamate receptor, and one domain homologous to the intracellular cytoplasmic tail domain of a calcium receptor.

In other preferred embodiments, the chimeric receptor has at least one cytoplasmic loop of the seven transmembrane domain which is homologous to a cytoplasmic loop of a metabotropic glutamate receptor. Similarly, in other preferred embodiments, the chimeric receptor has at least one cytoplasmic loop homologous to a cytoplasmic loop of a calcium receptor.

Also in other preferred embodiments, the chimeric receptor has a sequence of at least 6 contiguous amino acids which is homologous to an amino acid sequence of a calcium receptor, and the rest of the sequence of the chimeric receptor is homologous to an amino acid sequence of a metabotropic glutamate receptor. In other embodiments, the sequence homologous to an amino acid sequence of a calcium receptor may beneficially be longer, for example at least 12, 18, 24, 30, 36, or more amino acids in length.

Similarly, in other preferred embodiments, the chimeric receptor has a sequence of at least 6 contiguous amino acids which is homologous to an amino acid sequence of a metabotropic glutamate receptor, and the rest of the sequence of the chimeric receptor is homologous to an amino acid sequence of a calcium receptor. In other embodiments, the sequence homologous to an amino acid sequence of a metabotropic glutamate receptor may beneficially be longer, for example at least 12, 18, 24, 30, 36, or more amino acids in length.

In a related aspect, the invention provides a composition which includes an isolated, enriched, or purified nucleic acid molecule which codes for a chimeric receptor as described for the aspect above. In particular, this includes nucleic acid coding for a chimeric receptor having a sequence of at least 6 contiguous amino acids which is homologous to an amino acid sequence of a calcium receptor and a sequence of at least 6 contiguous amino acids which is homologous to an amino acid sequence of a metabotropic glutamate receptor. Similarly to the above aspect, in particular embodiments the chimeric receptor sequence homologous to an amino acid sequence from a calcium receptor and/or a metabotropic glutamate receptor may beneficially be longer, for example, at least 12, 18, 24, 30, 36, or more amino acids in length.

In preferred embodiments, the chimeric receptor has a domain homologous to a domain of a metabotropic glutamate receptor, and/or a domain homologous to a calcium receptor. In more preferred embodiments, the chimeric receptor has two domains homologous to domains of a metabotropic glutamate receptor and a domain homologous to a domain of a calcium receptor, or two domains homologous to domains of a calcium receptor and a domain homologous to a domain of a metabotropic glutamate receptor.

In another related aspect, the nucleic acid encoding a chimeric receptor, as described above, is present in a replicable expression vector. Thus, the vector can include nucleic acid sequences coding for any of the chimeric receptors described.

Also in a related aspect, the invention provides a recombinant host cell transformed with a replicable expression vector as described above.

The invention also features a process for the production of a chimeric receptor; the process involves growing, under suitable nutrient conditions, procaryotic or eucaryotic host cells transformed or transfected with a replicable expression vector containing a nucleic acid sequence coding for a chimeric receptor as described above, in a manner allowing expression of the chimeric receptor.

By "isolated" in reference to a nucleic acid is meant the nucleic acid is present in a form (i.e., its association with other molecules) other than found in nature. For example, isolated receptor nucleic acid is separated from one or more nucleic acids which are present on the same chromosome. Preferably, the isolated nucleic acid is separated from at least 90% of the other nucleic acids present on the same chromosome. Preferably, the nucleic acid is provided as a substantially purified preparation representing at least 75%, more preferably 85%, most preferably 95% of the total nucleic acids present in the preparation.

Another example of an isolated nucleic acid is recombinant nucleic acid. Preferably, recombinant nucleic acid contains nucleic acid encoding a chimeric metabotropic glutamate receptor or metabotropic glutamate receptor fragment cloned in an expression vector. An expression vector contains the necessary elements for expressing a cloned nucleic acid sequence to produce a polypeptide. An expression vector contains a promoter region (which directs the initiation of RNA transcription) as well as the DNA sequences which, when transcribed into RNA, will signal synthesis initiation. "Expression vector" includes vectors which are capable of expressing DNA sequences contained therein, i.e., the coding sequences are operably linked to other sequences capable of effecting their expression. It is implied, although not always explicitly stated, that these expression vectors must be replicable in the host organisms either as episomes or as an integral part of the chromosomal DNA. A useful, but not a necessary, element of an effective expression vector is a marker encoding sequence—i.e., a sequence encoding a protein which results in a phenotypic property (e.g. tetracycline resistance) of the cells containing the protein which permits those cells to be readily identified. In sum, "expression vector" is given a functional definition, and any DNA sequence which is capable of effecting expression of a specified contained DNA code is included in this term, as it is applied to the specified sequence. As at present, such vectors are frequently in the form of plasmids, thus "plasmid" and "expression vector" are often used interchangeably. However, the invention is intended to include such other forms of expression vectors, including viral vectors, which serve equivalent functions and which may, from time to time become known in the art. Recombinant nucleic acids may contain nucleic acids encoding for a chimeric metabotropic glutamate receptor, receptor fragment, or chimeric metabotropic glutamate receptor derivative, under the control of its genomic regulatory elements, or under the control of exogenous regulatory elements including an exogenous promoter. By "exogenous" is meant a promoter that is not normally coupled in vivo transcriptionally to the coding sequence for the metabotropic glutamate receptor or calcium receptor.

The invention also provides methods of screening for compounds which bind to and/or modulate the activity of a metabotropic glutamate receptor and/or a calcium receptor. These methods utilize chimeric receptors as described above or nucleic acid sequence encoding such chimeric receptors.

Such chimeric receptors provide useful combinations of characteristics from the two types of receptors, such as combining the binding characteristics from a metabotropic glutamate receptor with the cellular signaling characteristics from a calcium receptor.

Thus, in another aspect the invention provides a method of screening for a compound that binds to or modulates the activity of a metabotropic glutamate receptor. The method involves preparing a chimeric receptor having an extracellular domain, a seven transmembrane domain, and an intracellular cytoplasmic tail domain, in which at least one domain is homologous to a domain of a metabotropic glutamate receptor and at least one domain is homologous to a domain of a calcium receptor. The chimeric receptor and a test compound are introduced into an acceptable medium. The binding of a test compound to the chimeric receptor, or the modulation of the chimeric receptor by the compound, is monitored by physically detectable means to identify those compounds which bind to or modulate the activity of a metabotropic glutamate receptor.

In a preferred embodiment the extracellular domain of the chimeric receptor is homologous to the extracellular domain of a metabotropic glutamate receptor. Also in preferred embodiments, the chimeric receptor has two domains homologous to domains of a metabotropic glutamate receptor and a domain homologous to a domain of a calcium receptor, or two domains homologous to domains of a calcium receptor and a domain homologous to a domain of a metabotropic glutamate receptor.

In another aspect the invention provides a method of screening for a compound which binds to or modulates the activity of a metabotropic glutamate receptor, utilizing a nucleic acid coding for a chimeric receptor. This method involves preparing a nucleic acid sequence encoding a chimeric receptor which has an extracellular domain, a seven transmembrane domain and an intracellular cytoplasmic tail domain, in which the chimeric receptor has a sequence of at least six contiguous amino acids which is homologous to a sequence of amino acids of a calcium receptor and a sequence of at least six contiguous amino acids which is homologous to a sequence of amino acids of a metabotropic glutamate receptor. The nucleic acid sequence is inserted into a replicable expression vector capable of expressing the chimeric receptor in a host cell. A suitable host cell is transformed with this vector and the transformed host cell and a test compound are introduced into an acceptable medium. Identification of binding or modulation by the test compound is performed by monitoring the effect of the compound on the cell.

In a preferred embodiment the chimeric receptor has at least one domain homologous to a domain of metabotropic glutamate receptor and/or at least one domain homologous to a domain of a calcium receptor. In particular this includes preferred embodiments in which the chimeric receptor has an extracellular domain homologous to an extracellular domain of a metabotropic glutamate receptor and/or a seven transmembrane domain of a metabotropic glutamate receptor. In particular embodiments, the chimeric receptor has two domains homologous to domains of a metabotropic glutamate receptor and a domain homologous to a domain of a calcium receptor, or two domains homologous to domains of a calcium receptor and a domain homologous to a domain of a metabotropic glutamate receptor.

Also in a preferred embodiment the chimeric receptor has at least one cytoplasmic loop of the seven transmembrane domain which is homologous to a cytoplasmic loop of a calcium receptor; in particular embodiments the sequence of the remainder of the chimeric receptor is homologous to the sequence of a metabotropic glutamate receptor.

In another preferred embodiment the chimeric receptor has a sequence of at least six contiguous amino acids which is homologous to a sequence of amino acids of a calcium receptor and the remainder of the amino acids sequence of a chimeric receptor is homologous to an amino acid sequence of a metabotropic glutamate receptor. In yet another preferred embodiment the chimeric receptor has at least one cytoplasmic loop of the seven transmembrane domain which is homologous to a cytoplasmic loop of a metabotropic glutamate receptor.

In still another preferred embodiment the host cell is a eucaryotic cell.

In the context of the methods of this invention, "monitoring the effect" of a compound on a host cell refers to determining the effects of the compound on one or more cellular processes or on the level of activity of one or more cellular components, or by detection of an interaction between the compound and a cellular component.

The invention also provides methods of screening for compounds that bind to or modulate a metabotropic glutamate receptor or calcium receptor using fragments of such receptors. Such fragments can, for example, be chosen to include a sequence which has been shown to be important in activation of the receptor's signal pathway.

Thus, in another aspect the invention features a method of screening for a compound that binds to a metabotropic glutamate receptor or a calcium receptor, by preparing a nucleic acid encoding a fragment of such a receptor, inserting the sequence into a replicable expression vector which can express that fragment in a host cell, transforming a suitable host cell with a vector, recovering the fragment from the host cell, introducing the fragment in a test compound into an acceptable medium and monitoring the binding of the compound to the fragment by physically detectable means.

In a preferred embodiment the fragment is a fragment of a metabotropic glutamate receptor; in a more preferred embodiment the fragment includes the extracellular domain of that receptor.

In another preferred embodiment the fragment includes the seven transmembrane domain of a metabotropic glutamate receptor. In a more preferred embodiment the fragment includes both the seven transmembrane domain and the cytoplasmic tail domain of a metabotropic glutamate receptor.

Similarly in another preferred embodiment the fragment is a fragment of a calcium receptor, preferably including the extracellular domain over the seven transmembrane domain of that receptor. In a more preferred embodiment the fragment includes the seven transmembrane domain and cytoplasmic tail domain of the calcium receptor.

Certain receptor fragments are able to activate one or more cellular responses in a manner similar to the receptor from which the fragment was derived. Therefore, in a related aspect, the invention provides a method of screening for a compound that binds to or modulates a metabotropic glutamate receptor or a calcium receptor by preparing a nucleic acid sequence encoding a fragment of such a receptor, inserting that sequence into a replicable expression vector, transforming a host cell with that vector, introducing the host cell and a test compound into an acceptable medium, and monitoring the effect of the compound on the host cell.

For certain receptors it is possible to utilize fragments of two different receptors to screen for compounds which bind to or modulate a receptor. The method involves preparing a nucleic acid encoding a fragment of a first receptor, inserting the sequence into a replicable expression vector capable of expressing that fragment in a host cell, transforming a suitable host cell with a vector, and recovering the first fragment from the host cell. A fragment of a second receptor is prepared in a similar manner. The two fragments and a test compound are introduced into an acceptable medium and the binding and/or modulation by the compound is monitored by physically detectable means.

In preferred embodiments a fragment is from a metabotropic glutamate receptor and a fragment is from a calcium receptor. In particular preferred embodiments the first fragment includes the extracellular domain of a metabotropic glutamate receptor and the second fragment includes the seven transmembrane domain and cytoplasmic tail domain of a calcium receptor, or the first fragment includes the extracellular domain and the seven transmembrane domain of a metabotropic glutamate receptor and the second fragment includes the cytoplasmic tail domain of a calcium receptor.

In another particular embodiment the first fragment includes the extracellular domain of a calcium receptor and the second fragment includes the seven transmembrane domain and the cytoplasmic tail domain of a metabotropic glutamate receptor. In still another particular preferred embodiment, the first fragment includes the extracellular domain of a calcium receptor and the second fragment includes the seven transmembrane domain of a metabotropic glutamate receptor and the cytoplasmic tail domain of a calcium receptor.

Certain compounds can be identified which modulate the activity of both a metabotropic glutamate receptor and of a calcium receptor. Thus, this invention also provides a method for screening for such compounds by preparing a nucleic acid sequence encoding a chimeric receptor which includes a domain homologous to a domain of a metabotropic glutamate receptor and a domain homologous to a domain of a calcium receptor. The sequence is inserted in a replicable expression vector capable of expressing the receptor in a host cell; a suitable host cell is transformed with the vector and the transformed host cell and a test compound are introduced into an acceptable medium. The binding or modulation by the compound is observed by monitoring the effect of a compound on the host cell.

The invention also provides methods for determining the site of action of a compound active on a metabotropic glutamate receptor or on a calcium receptor. The methods involve preparing a nucleic acid sequence which encodes a chimeric receptor. In two related aspects, a chimeric receptor has at least a six amino acid sequence which is homologous to a sequence of amino acids of a calcium receptor and the remainder of the amino acid sequence is homologous to an amino acid sequence of a metabotropic glutamate receptor, or the chimeric receptor has at least a six amino acid sequence which is homologous to a sequence of amino acids of a metabotropic glutamate receptor and the remainder of amino acid sequence is homologous to a sequence of a calcium receptor. In these aspects, the nucleic acid sequence is inserted into a replicable expression vector which is capable of expressing the receptor in a host cell. The vector is transformed into a suitable host cell and the transformed host cell in the compound are introduced into an acceptable medium. The effect of the compound on the host cell is monitored; thus if a compound is active on a receptor through an interaction at the sequence of at least six amino acids from the corresponding receptor, the chimeric receptor will be activated and the cellular effects can be observed. On the other hand if the compound does not interact with the at least six amino acid sequence, thereby activating the receptor, the corresponding cellular effects will not be observed.

Thus, "site of action" refers to the location(s) on the receptor which are involved in interaction with a natural ligand for that receptor, or with another compound of interest. For example, for a compound which modulates the activity of a metabotropic glutamate receptor by binding to the receptor, the site of action can include amino acid sequences associated with binding of the compound to the receptor, but may also include other sequences. Such other sequences can, for example, include sequences whose secondary or tertiary structure is altered in response to the binding of the compound.

Other features and advantages of the invention will be apparent from the following description of the preferred embodiments, and from the claims.

BRIEF DESCRIPTION OF THE DRAWINGS

FIGS. 2 (A–H) is a representation of the nucleotide sequence (SEQ I.D. NO. 1) and corresponding amino acid sequence (SEQ ID NO:5) of pmGluR1/CaR, [SEQ I.D. NO. 1] described in Example 2.

FIGS. 3 (A–H) is a representation of the nucleotide sequence (SEQ ID NO:2) and corresponding amino acid sequence (SEQ ID NO:6) of pCaR/R$_1$, [SEQ I.D. NO.2] described in Example 3.

FIGS. 4 (A–G) is a representation of the nucleotide sequence (SEQ ID NO:3) and corresponding amino acid sequence (SEQ ID NO:7) of pratCH3, [SEQ I.D. NO.3] described in Example 4.

FIGS. 5 (A–G) is a representation of the nucleotide sequence (SEQ ID NO:4) and corresponding amino acid sequence (SEQ ID NO:8) of phCH4, [SEQ I.D. NO.4] described in example 4.

DETAILED DESCRIPTION

Figure 1A:
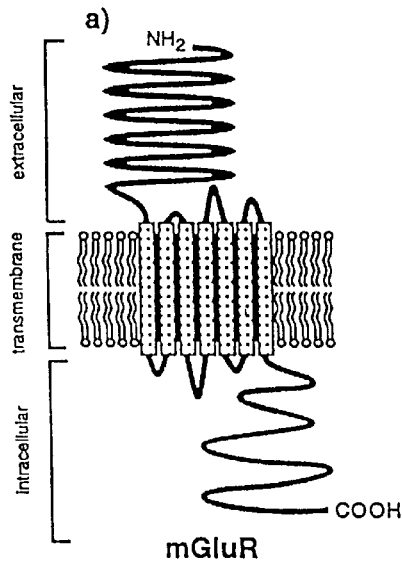
FIGS. 1A–F is a schematic illustration of the various chimeras described herein, illustrating the extracellular domains, 7-transmembrane domains, and intracellular cytoplasmic tail domains of the chimeras.
Figure 1B:
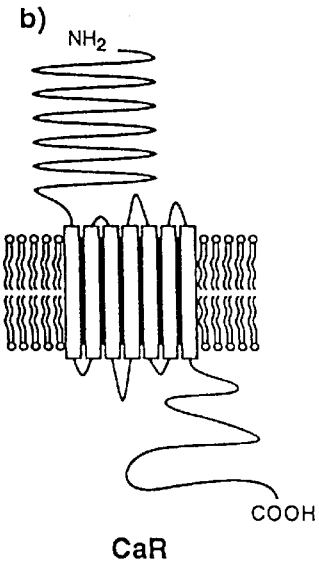
Figure 1C:
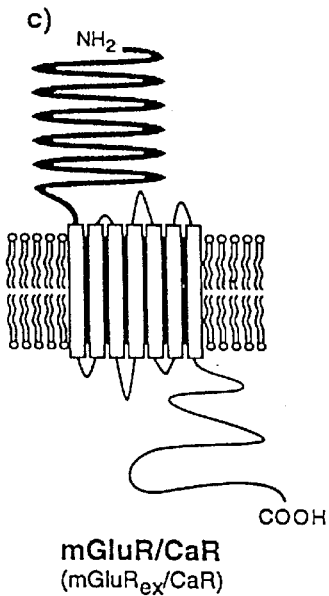
Figure 1D:
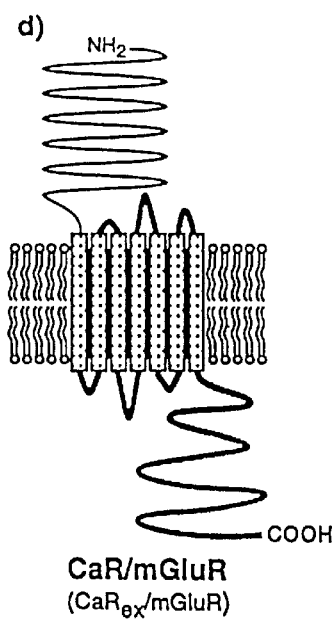
Figure 1E:
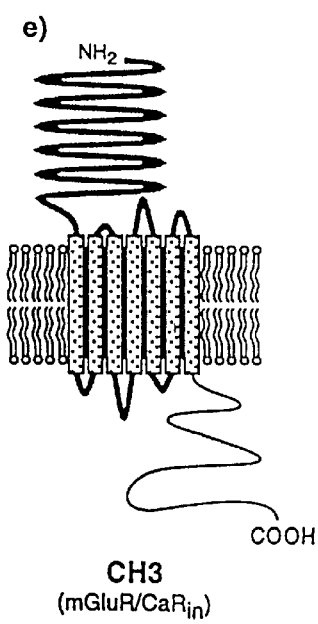
Figure 1F:
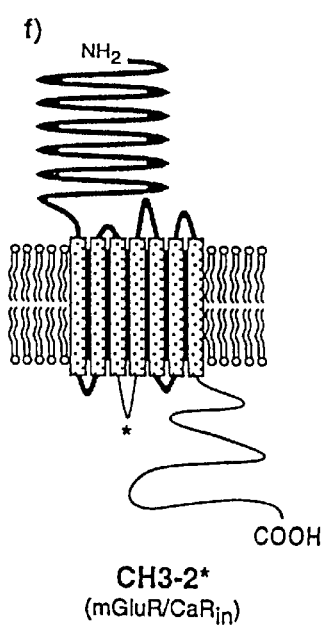

It will be readily apparent to one skilled in the art that various substitutions and modifications may be made to the invention disclosed herein without departing from the scope and spirit of the invention.

I. Definitions

The following is a list of some of the definitions used in the present disclosure. These definitions are to be understood in light of the entire disclosure provided herein.

By "adjunct in general anesthesia" is meant a compound used in conjunction with an anesthetic agent which decreases the ability to perceive pain associated with the loss of consciousness produced by the anesthetic agent.

By "allodynia" is meant pain due to a stimulus that does not normally provoke pain.

By "analgesic" is meant a compound capable of relieving pain by altering perception of nociceptive stimuli without producing anesthesia resulting in the loss of consciousness.

By "analgesic activity" is meant the ability to reduce pain in response to a stimulus that would normally be painful.

By "anticonvulsant activity" is meant efficacy in reducing convulsions such as those produced by simple partial seizures, complex partial seizures, status epilepticus, and trauma-induced seizures such as occur following head injury, including head surgery.

By "binds to or modulates" is meant that the agent may both bind and modulate the activity of a receptor, or the agent may either bind to or modulate the activity of a receptor.

By "causalgia" is meant a painful disorder associated with injury of peripheral nerves.

By "central pain" is meant pain associated with a lesion of the central nervous system.

By "cognition-enhancement activity" is meant the ability to improve the acquisition of memory or the performance of a learned task. Also by "cognition-enhancement activity" is meant the ability to improve normal rational thought processes and reasoning.

By "cognition enhancer" is meant a compound capable of improving learning and memory.

By "efficacy" is meant that a statistically significant level of the desired activity is detectable with a chosen compound; by "significant" is meant a statistical significance at the $p<0.05$ level.

By "homologous" is meant a functional equivalent to the domain, the amino acid sequence, or the nucleic acid sequence, having similar nucleic acid and/or amino acid sequence and retaining, to some extent, one or more activities of the related receptor. Homologous domains or sequences of receptors have at least 50% sequence similarity, preferably 70%, more preferably 90%, even more preferably 95% sequence similarity to the related receptor. "Sequence similarity" refers to "homology" observed between amino acid sequences in two different polypeptides, irrespective of polypeptide origin. Thus, homologous includes situations in which the nucleic acid and/or amino acid sequences are the same. In related phrases, reference to a sequence, sub-domain, or domain being "from a metabotropic glutamate receptor" or "of a metabotropic glutamate receptor" means that the portion is the same as or homologous to a portion of a metabotropic glutamate receptor; like references to portions being "from a calcium receptor" or "of a calcium receptor" also indicate the portions are the same as or homologous to portions of a calcium receptor. These phrases can be used in reference to amino acid sequences and/or nucleic sequences.

The ability of the homologous domain or sequence to retain some activity can be measured using techniques described herein. Such homologous domains may also be derivatives. Derivatives include modification occurring during or after translation, for example, by phosphorylation, glycosylation, crosslinking, acylation, proteolytic cleavage, linkage to an antibody molecule, membrane molecule or other ligand (see Ferguson et al., 1988, *Ann. Rev. Biochem.* 57:285–320).

Specific types of derivatives also include amino acid alterations such as deletions, substitutions, additions, and amino acid modifications. A "deletion" refers to the absence of one or more amino acid residue(s) in the related polypeptide. An "addition" refers to the presence of one or more amino acid residue(s) in the related polypeptide. Additions and deletions to a polypeptide may be at the amino terminus, the carboxy terminus, and/or internal. Amino acid "modification" refers to the alteration of a naturally occurring amino acid to produce a non-naturally occurring amino acid. A "substitution" refers to the replacement of one or more amino acid residue(s) by another amino acid residue(s) in the polypeptide. Derivatives can contain different combinations of alterations including more than one alteration and different types of alterations.

While the effect of an amino acid change varies depending upon factors such as phosphorylation, glycosylation, intrachain linkages, tertiary structure, and the role of the amino acid in the active site or a possible allosteric site, it is generally preferred that the substituted amino acid is from the same group as the amino acid being replaced. To some extent the following groups contain amino acids which are interchangeable: the basic amino acids lysine, arginine, and histidine; the acidic amino acids aspartic and glutamic acids; the neutral polar amino acids serine, threonine, cysteine, glutamate, asparagine and, to a lesser extent, methionine; the nonpolar aliphatic amino acids glycine, alanine, valine, isoleucine, and leucine (however, because of size, glycine and alanine are more closely related and valine, isoleucine and leucine are more closely related); and the aromatic amino acids phenylalanine, tryptophan, and tyrosine. In addition, although classified in different categories, alanine, glycine, and serine seem to be interchangeable to some extent, and cysteine additionally fits into this group, or may be classified with the polar neutral amino acids.

While proline is a nonpolar neutral amino acid, its replacement represents difficulties because of its effects on conformation. Thus, substitutions by or for proline are not preferred, except when the same or similar conformational results can be obtained. The conformation conferring properties of proline residues may be obtained if one or more of these is substituted by hydroxyproline (Hyp).

Examples of modified amino acids include the following: altered neutral nonpolar amino acids such as ω-amino acids of the formula $H_2N(CH_2)_n COOH$ where n is 2–6, sarcosine (Sar), t-butylalanine (t-BuAla), t-butylglycine (t-BuGly), N-methyl isoleucine (N-MeIle), and norleucine (Nleu); altered neutral aromatic amino acids such as phenylglycine; altered polar, but neutral amino acids such as citrulline (Cit) and methionine sulfoxide (MSO); altered neutral and nonpolar amino acids such as cyclohexyl alanine (Cha); altered acidic amino acids such as cysteic acid (Cya); and altered basic amino acids such as ornithine (Orn).

Preferred derivatives have one or more amino acid alteration(s) which do not significantly affect the receptor activity of the related receptor protein. In regions of the receptor protein not necessary for receptor activity amino acids may be deleted, added or substituted with less risk of affecting activity. In regions required for receptor activity, amino acid alterations are less preferred as there is a greater risk of affecting receptor activity. Such alterations should be conservative alterations. For example, one or more amino acid residues within the sequence can be substituted by another amino acid of a similar polarity which acts as a functional equivalent.

Conserved regions tend to be more important for protein activity than non-conserved regions. Standard procedures can be used to determine the conserved and non-conserved regions important of receptor activity using in vitro mutagenesis techniques or deletion analyses and measuring receptor activity as described by the present disclosure.

Derivatives can be produced using standard chemical techniques and recombinant nucleic acid techniques. Modifications to a specific polypeptide may be deliberate, as through site-directed mutagenesis and amino acid substitution during solid-phase synthesis, or may be accidental such as through mutations in hosts which produce the polypeptide. Polypeptides including derivatives can be obtained using standard techniques such as those described in Section I.G.2. supra, and by Sambrook et al., *Molecular Cloning*, Cold Spring Harbor Laboratory Press (1989). For example, Chapter 15 of Sambrook describes procedures for site-directed mutagenesis of cloned DNA.

By "hyperalgesia" is meant an increased response to a stimulus that is normally painful.

By "minimal" is meant that any side effect of the drug is tolerated by an average individual, and thus that the drug can be used for therapy of the target disease or disorders. Such side effects are well known in the art. Preferably, minimal side effects are those which would be regarded by the FDA as tolerable for drug approval for a target disease or disorder.

By "modulate" is meant to cause an increase or decrease in an activity of a cellular receptor.

By "modulator" is meant a compound which modulates a receptor, including agonists, antagonists, allosteric modulators, and the like. Preferably, the modulator binds to the receptor.

By "muscle relaxant" is meant a compound that reduces muscular tension.

By "neuralgia" is meant pain in the distribution of a nerve or nerves.

By "neurodegenerative disease" is meant a neurological disease affecting cells of the central nervous system resulting in the progressive decrease in the ability of cells of the nervous system to function properly. Examples of neurodegenerative diseases include Alzheimer's disease, Huntington's disease, and Parkinson's disease.

By "neurological disorder or disease" is meant a disorder or disease of the nervous system. Examples of neurological disorders and diseases include global and focal ischemic and hemorrhagic stroke, head trauma, spinal cord injury, hypoxia-induced nerve cell damage as in cardiac arrest or neonatal distress, and epilepsy.

By "neuroprotectant activity" is meant efficacy in treatment of the neurological disorders or diseases.

By "physically detectable means" is meant any means known to those of ordinary skill in the art to detect binding to or modulation of mGluR or CaR receptors, including the binding and screening methods described herein. Thus, for example, such means can include spectroscopic methods, chromatographic methods, competitive binding assays, and assays of a particular cellular function, as well as other techniques.

By "potent" is meant that the compound has an $EC_{50}$ value (concentration which produces a half-maximal activation), or $IC_{50}$ (concentration which produces half-maximal inhibition), or $K_d$ (concentration which produces half-maximal binding) at a metabotropic glutamate receptor, with regard to one or more receptor activities, of less than 100 $\mu M$, more preferably less than 10 $\mu M$, and even more preferably less than 1 $\mu M$.

By "selective" is meant that the compound activates, inhibits activation and/or binds to a metabotropic glutamate receptor at a lower concentration than that at which the compound activates, inhibits activation and/or binds to an ionotropic glutamate receptor. Preferably, the concentration difference is a 10-fold, more preferably 50-fold, and even more preferably 100-fold.

By "therapeutically effective amount" is meant an amount of a compound which produces the desired therapeutic effect in a patient. For example, in reference to a disease or disorder, it is the amount which reduces to some extent one or more symptoms of the disease or disorder, and returns to normal, either partially or completely, physiological or biochemical parameters associated or causative of the disease or disorder. When used to therapeutically treat a patient it is an amount expected to be between 0.1 mg/kg to 100 mg/kg, preferably less than 50 mg/kg, more preferably less than 10 mg/kg, more preferably less than 1 mg/kg. Preferably, the amount provides an effective concentration at a metabotropic glutamate receptor of about 1 nM to 10 $\mu M$ of the compound. The amount of compound depend on its $EC_{50}$ ($IC_{50}$ in the case of an antagonist) and on the age, size, and disease associated with the patient.

II. Techniques

A. Chimeric Receptors and General Approach to Uses

As indicated in the Summary above, this invention concerns chimeric receptors, which include portions of both metabotropic glutamate receptor and calcium receptor proteins. It also is concerned with fragments of metabotropic glutamate receptors and calcium receptors. Related aspects include nucleic acids encoding such chimeric receptors and fragments, uses of such receptors, fragments and nucleic acids, and cell lines expressing such nucleic acids. The uses disclosed include methods of screening for compounds that bind to or modulate the activity of metabotropic glutamate receptors or calcium receptors using such chimeric receptors and fragments. The invention also includes compounds for modulating metabotropic glutamate receptors or calcium receptors identified by such methods of screening, and methods for treating certain disorders or for modulating metabotropic glutamate receptors or calcium receptors utilizing such compounds.

Experiments carried out on several distinct G-protein coupled receptors have suggested the general principle that G-protein coupling specificity and receptor desensitization are determined primarily by amino acid sequences which are intracellular (i.e., sequences within one or more of the three cytoplasmic loops and/or the intracellular cytoplasmic tail). Recent experiments in which chimeric receptors were formed by combining distinct protein segments from different metabotropic glutamate receptors (mGlurs), suggest that, in these receptors, ligand binding specificity is determined by the extracellular domain.

Thus, preferred embodiments of the present invention include chimeric receptors consisting of the extracellular domain (ECD) of an mGluR and the seven-transmembrane domain (7TMD) and the intracellular cytoplasmic tail (CT) of a calcium receptor (CaR) that responds to mGluR-active molecules by signal transduction analogous to that observed when CaR-active molecules act on a CaR.

Similarly, in other preferred embodiments, the invention includes chimeric receptors in which the intracellular cytoplasmic C-terminal tail domain of a chosen mGluR is replaced by the C-terminal tail of a calcium receptor. The C-terminal tail encompasses the cytoplasmic region which follows the seventh transmembrane region.

Preferred embodiments of the invention also include chimeric receptors in which the peptide sequences encompassing all or some of the cytoplasmic loop domains (between the first and second, the third and fourth, and the fifth and sixth transmembrane regions) of an mGluR have been replaced similarly with corresponding peptide sequences from one or more CaRs. In particular such embodiments include chimeric receptors having the ECD of an mGluR, the 7TMD of an mGluR, and the C-terminal tail of a calcium receptor, except that one or more sub-domains of the 7-TMD are substituted with sequences from a CaR. This specifically includes receptors in which one or more of the cytoplasmic loops of the 7TMD are replaced with sequences from a CaR. Such substitution of cytoplasmic loops may be done singly or in any combination. In general, using techniques known to those skilled in the art, such target "domains" and "sub-domains" may be "swapped" individually or in combination.

These chimeric receptors are unknown in the art and their function is unexpected because functional chimeric receptors had previously been successfully constructed only by combining portions of much more closely related receptors. Indeed, the sequence identity between metabotropic glutamate receptors and calcium receptors is only about 19–25%, and the two types of receptors share only about 25–30% sequence similarity (Brown E. M. et al., *Nature* 366:575, 1993).

Experiments have shown that ligands known in the art which are agonists or antagonists on the native mGluRs also exhibit such activities on the chimeric receptors in which the extracellular domain is from an mGluR. Other ligands which bind to the ECD and modulate the activity of mGluRs, for example, agonists, antagonists, allosteric modulators and the like, are also predicted to act on such chimeric receptors. Experiments have also shown that ligands known in the art which modulate mGluRs act on the chimeric receptors in which the ECD and 7TMD are from an mGluR. Other ligands which modulate mGluR activity are also predicted to act on this type of chimeric receptors regardless of whether they bind the ECD or 7TMD of mGluRs.

The chimeric receptors are linked to intracellular or second messenger functions in a similar fashion to the linkage known for non-modified calcium receptors. For example, as is the case for CaRs, the chimeric receptors are also coupled through a G-protein(s) to the activation of phospholipase C, to the generation of inositol phosphates and/or to the release of calcium ions from intracellular stores. Although the mGluRs rapidly desensitize upon ligand binding/activation, the CaRs do not, allowing for more efficient high-throughput screening of compounds active at the CaR and stable receptor expression in recombinant cell lines. Importantly, the chimeric mGluR/CaR receptors do not rapidly desensitize upon ligand binding/activation and can be therefore efficiently used for high throughput screening. In addition, the chimeric receptors can be functionally expressed in stable cell lines.

Cells expressing such chimeric receptors can be prepared and used in functional assays to identify compounds which modulate activities of selected mGluRs. For example, increases in intracellular calcium levels resulting from receptor activation can be monitored by use of fluorescent calcium chelating dyes. Functional assays have been described for identifying molecules active at calcium receptors (see for example, published PCT patent application "Calcium Receptor-Active Molecules," PCT No. US93/01642 (WO94/18959), published September 1994 hereby incorporated by reference herein in its entirety).

An increasingly common practice in modern drug discovery is the use of various target-site-specific assays to identify specific molecules with activities of interest. These assays select drug lead molecules from large collections or libraries of molecules (e.g., combinatorial libraries, proprietary compound libraries held by large drug companies, etc.). Drug lead molecules are "selected" when they bind to pharmacological targets of interest and thus potentially modify the activities of these targets. The assays can be of many types including direct binding displacement assays or indirect functional assays. In order to successfully develop and use an assay to isolate lead therapeutic compounds, the target molecule (e.g., receptor) must first be identified and isolated. Many functional assays have been described in the literature for identifying molecules active at various receptors and these provide unique advantages over binding assays. It is not necessary to know, a priori, which ligands modulate the activity of the receptor in vivo, nor is it necessary to know the exact physiological function of the receptor. Compounds identified in functional assays and in subsequent medicinal chemistry efforts can be used as experimental test compounds to obtain such knowledge.

While eight distinct mGluRs are currently known, their discrete functions remain largely undetailed. Nevertheless, molecules active at mGluRs are sought by pharmaceutical companies because these receptors are found in the central nervous system and are known to be involved in the regulation of processes related to memory, motor functions, pain sensation, neurodegeneration and the like. Thus, compounds which modulate mGluRs may be useful in the treatment of disorders or diseases affecting memory, cognition, and motor function (e.g., in seizures) as well as in the treatment of pain and neurodegenerative disorders (e.g., stroke, Alzheimers disease and the like).

Screens to identify molecules active at mGluRs can be constructed using cloned mGluRs themselves. However, functional screens using native mGluRs are problematic. First, most mGluRs are coupled through $G_i$ proteins and this limits their use in functional assays because $G_i$ proteins are linked to inhibition of adenylate cyclase and changes in adenylate cyclase are not easily measured in high throughput functional screens designed to select drug lead molecules from large compound libraries.

Receptors which couple through other G-proteins to activation of phospholipase C (e.g., $G_q$-coupled receptors) do not suffer this drawback, so it was initially thought that mGluR1 and mGluR5 could find utility in functional assays because these two mGluRs are coupled through Gq-protein (s) to measurable intracellular functions (e.g., activation of phospholipase C, generation of inositol phosphates and the release of calcium ions from intracellular stores).

Figure 8A:
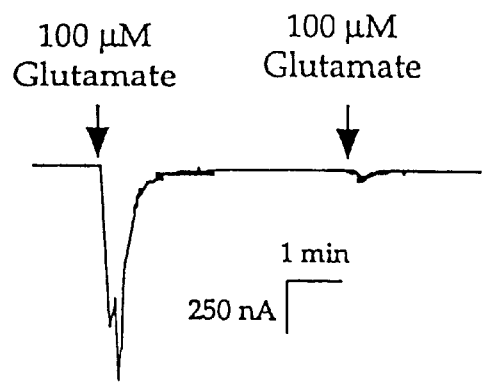
FIGS. 8A–C is a graphical representation showing that extracellular glutamate elicits oscillatory increases in Cl− current in Xenopus oocytes injected with a) ratmGluR1 RNA, B) human CaR RNA and C) rat CH3 RNA. However, when oocytes are repeatedly supplied with agonist, the rat mGluR1 receptor desensitizes and does not activate the release of intracellular Ca2+. RatCH3, which encodes the cytoplasmic tail of the CaR does not desensitize like the native rat mGluR1 and is thus amenable to repeated challenges with compounds.

A second limitation is presented here, however, because these particular mGluRs rapidly desensitize upon agonist binding. That is, the functional response disappears rapidly and cannot quickly be recovered (see for example FIG. 8a). Furthermore, it has not always been possible to obtain fully functional stable cell lines expressing mGluRs regardless of the G-protein to which they couple (Tanabe et al., 1992, *Neuron* 8:169–179; Gabellini et al., 1994, *Neurochem Int.* 24:533–539). Thus, nontrivial technical difficulties must be overcome in order to use native mGluRs in an optimal manner in high throughput functional screening assays.

Figure 8B:
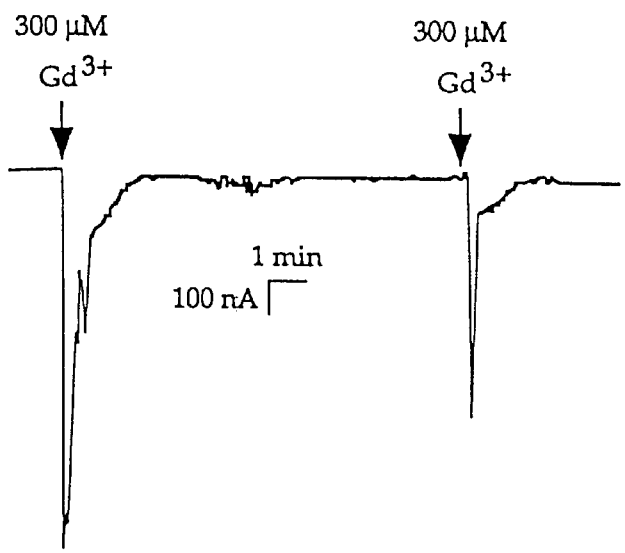
Figure 8C:
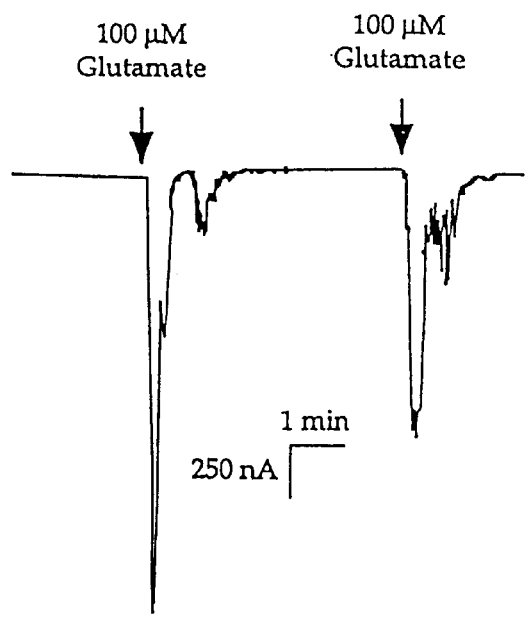

The invention described herein overcomes these technical difficulties and provides a much improved screening method by utilizing the more robust aspects of the calcium receptors which do not rapidly desensitize upon ligand binding/activation and can be expressed stably in recombinant vertebrate cells (see for example, FIG. 8b and see also published PCT patent application "Calcium Receptor-Active Molecules," PCT No. US93/01642 (WO94/18959), published September 1994, hereby incorporated by reference herein). Thus, for example, by coupling the 7TMD and the CT of the CaR to the extracellular domain of mGluR, or the CT of the CaR to the ECD and 7TMD of the mGluR, the mGluR extracellular domain has the benefit of the Gq coupling property of a CaR, as well as the improved property of a lack of rapid desensitization (see, for example, FIG. 8c). Thus, the present invention provides chimeric receptors with ligand binding and activation properties similar to those of the native mGluRs, but with improved second messenger coupling similar to CaRs.

Thus, since the chimeric receptors simplify and enable, efficient, practical and reproducible functional screens to identify mGluR-active molecules, compositions and methods of the present invention are useful for the identification of molecules which modulate mGluR activity or calcium receptor activity. These can, for example, include agonists, antagonists, allosteric modulators, and the like. For example, chimeric receptors constructed to screen compounds active at metabotropic glutamate receptors may employ the signaling properties of certain domains of a calcium receptor. Such a chimeric receptor would take advantage of certain unique properties associated with the agonist-induced coupling of the calcium receptor to G-proteins which activate phospholipase C and mobilize intracellular calcium. These properties include, for example, the lack of ligand induced down-regulation/desensitization which is associated with ligand activation of metabotropic glutamate receptors. Thus the superior signaling properties of the calcium receptor can be transferred to metabotropic glutamate receptors which normally do not couple to G-proteins that activate phospholipase C and mobilize intracellular calcium such as those which couple to $G_i$.

In certain embodiments, recombinant cells expressing such chimeric receptors are used in screening methods. The cells will obtain properties, such as those indicated above, which facilitate their use in high-throughput functional assays, and thus provide a more efficient method of screening for compounds which bind to or modulate metabotropic glutamate receptor activity.

Generally, useful chimeric receptors include portions of mGluRs and CaRs, such that the portions confer a desired binding, signal coupling, or other functional characteristic to the chimeric receptor. The length of a sequence from a particular receptor can be of different sizes in different applications. In addition, the sequence of a portion from a particular receptor may be identical to the corresponding sequence in the mGluR or CaR, or it may be a homologous sequence, which retains the relevant function of the mGluR or CaR sequence. Therefore, chimeric receptors of this invention have an extracellular domain, a seven transmembrane domain, and an intracellular cytoplasmic tail domain. These chimeric receptors have a contiguous sequence of at least 6 amino acids which is homologous to a sequence from an mGluR, and a contiguous sequence of at least 6 amino acids which is homologous to a sequence from a CaR. However, in many cases, the sequences from the mGluR and/or the CaR may be longer than 6 amino acids. Thus, either or both of such sequences may be at least 12, 18, 24, 30, 36, or more amino acids in length.

The portions from the mGluR and the CaR will usually not be the same length. Thus, for example, the sequence from one of those types of receptor may be of a length as indicated above (e.g., et at least 6, 12, 18, 24, 30, 36, or more amino acids), while the rest of the sequence of the chimeric receptor is the same as or homologous to a sequence from the other type of receptor.

In certain embodiments, the portion from at least one receptor type is a subdomain. In this context, "subdomain" refers to a sequence of amino acids which is less than the entire sequence of amino acids for a domain. Examples of subdomains include, but are not limited to, ligand binding domains. Other examples include one of the cytoplasmic loops or regions of the seven transmembrane domain. Therefore, in certain cases, a chimeric receptor has an extracellular domain, a seven transmembrane domain, and an intracellular cytoplasmic tail domain, which include subdomains. In one example of such chimeric receptors, at least one subdomain is homologous to a subdomain of a calcium receptor and the remaining subdomains and domains are homologous to subdomains and domains of a metabotropic glutamate receptor. In another example, at least one subdomain is homologous to a subdomain of a metabotropic glutamate receptor and the remaining subdomains and domains are homologous to subdomains and domains of a calcium receptor.

In a more specific example, the seven transmembrane domain of a chimeric receptor includes three cytoplasmic loops; at least one cytoplasmic loop is homologous to a cytoplasmic loop of a metabotropic glutamate receptor; or at least one cytoplasmic loop is homologous to a cytoplasmic loop of a calcium receptor. In another specific example, the extracellular domain is homologous to the extracellular domain of a metabotropic glutamate receptor, the seven transmembrane domain is homologous to the seven transmembrane domain of a metabotropic glutamate receptor except that one or more of the cytoplasmic loops of the seven transmembrane domain is homologous to a cytoplasmic loop(s) of a calcium receptor, and the cytoplasmic tail is homologous to the cytoplasmic tail of a calcium receptor. Thus, any of cytoplasmic loops 1, 2, and 3 may be replaced, either singly or in any combination, with a cytoplasmic loop(s) of a calcium receptor.

In other cases, the chimeric receptor has a domain which has a sequence which is the same as or homologous to the sequence of a domain of an mGluR, or a CaR, or preferably, at least one domain from each of an mGluR and a CaR. More preferably, the chimeric receptor has two domains from one receptor type and one domain from the other receptor type. The compositions of certain preferred embodiments of such chimeric receptors are described below:

A composition comprising a chimeric receptor having:

1. one domain homologous to the extracellular domain of a calcium receptor, one domain homologous to the seven transmembrane domain of a metabotropic glutamate receptor, and one domain homologous to the intracellular cytoplasmic tail domain of a metabotropic glutamate receptor; or 2. one domain homologous to an extracellular domain of a metabotropic glutamate receptor, one domain homologous to the seven transmembrane domain of a calcium receptor, and one domain homologous to the intracellular cytoplasmic tail domain of a calcium receptor; or 3. one domain homologous to an extracellular domain of a metabotropic glutamate receptor, one domain homologous to the seven transmembrane domain of a calcium receptor, and one domain homologous to the intracellular cytoplasmic tail domain of a metabotropic glutamate receptor; or 4. one domain homologous to the extracellular domain of a calcium receptor, one domain homologous to the seven transmembrane domain of a metabotropic glutamate receptor, and one domain homologous to the intracellular cytoplasmic tail domain of a calcium receptor; or 5. one domain homologous to the extracellular domain of a calcium receptor, one domain homologous to the seven transmembrane domain of a calcium receptor, and one domain homologous to the intracellular cytoplasmic tail domain of a metabotropic glutamate receptor; or 6. one domain homologous to the extracellular domain of a metabotropic glutamate receptor, one domain homologous to the seven transmembrane domain of a metabotropic glutamate receptor, and one domain homologous to the intracellular cytoplasmic tail domain of a calcium receptor; or 7. one domain homologous to the extracellular domain of a metabotropic glutamate receptor, one domain homologous to the seven transmembrane domain of a metabotropic glutamate receptor except that one or more cytoplasmic loops are replaced with a cytoplasmic loop(s) homologous to a cytoplasmic loop(s) of a calcium receptor, and one domain homologous to the intracellular cytoplasmic tail domain of a calcium receptor.

B. Nucleic Acids Encoding Chimeric Receptors

Compositions which include isolated nucleic acid molecules which code for chimeric receptors as described above are also useful in this invention. Such nucleic acid molecules can be isolated, purified, or enriched. Preferably, the nucleic acid is provided as a substantially purified preparation representing at least 75%, more preferably 85%, most preferably 95% of the total nucleic acids present in the preparation.

Such nucleic acid molecules may also be present in a replicable expression vector. The replicable expression vector can be transformed into a suitable host cell to provide a recombinant host cell. Using such transformed host cells, the invention also provides a process for the production of a chimeric receptor, which includes growing, under suitable nutrient conditions, procaryotic or eucaryotic host cells transformed or transfected with a replicable expression vector comprising the nucleic acid molecule in a manner allowing expression of said chimeric receptor.

Uses of nucleic acids encoding chimeric receptors or receptor fragments include one or more of the following: producing receptor proteins which can be used, for example, for structure determination, to assay a molecule's activity on a receptor, to screen for molecules useful as therapeutics and to obtain antibodies binding to the receptor. The chimeras of the present invention are useful for identifying compounds active at either calcium receptors or metabotropic glutamate receptors, or both. Also, the fragments of the present invention are useful for identifying compounds which bind to or modulate either calcium receptors or metabotropic glutamate receptors, or both.

Thus, the invention also provides, for example, an isolated nucleic acid encoding an extracellular domain of a metabotropic glutamate receptor that is substantially free of the seven transmembrane domain and intracellular cytoplasmic tail domain of that metabotropic glutamate receptor. Similarly, the isolated nucleic acid can encode a metabotropic glutamate receptor that is substantially free of at least one membrane spanning domain portion. In another example, an isolated nucleic acid can encode a metabotropic glutamate receptor that is substantially free of the extracellular domain of that metabotropic glutamate receptor.

C. Metabotropic Glutamate Receptor Fragments and Calcium Receptor Fragments

Receptor fragments are portions of metabotropic glutamate receptors or of calcium receptors. Receptor fragments preferably bind to one or more binding agents which bind to a full-length receptor. Binding agents include ligands, such as glutamate, quisqualate, agonists and antagonists, and antibodies which bind to the receptor. Fragments have different uses such as to select other molecules able to bind to a receptor.

Fragments can be generated using standard techniques such as expression of cloned partial sequences of receptor DNA and proteolytic cleavage of a receptor protein. Proteins are specifically cleaved by proteolytic enzymes, such as trypsin, chymotrypsin or pepsin. Each of these enzymes is specific for the type of peptide bond it attacks. Trypsin catalyzes the hydrolysis of peptide bonds whose carbonyl group is from a basic amino acid, usually arginine or lysine. Pepsin and chymotrypsin catalyze the hydrolysis of peptide bonds from aromatic amino acids, particularly tryptophan, tyrosine and phenylalanine.

Alternate sets of cleaved protein fragments are generated by preventing cleavage at a site which is susceptible to a proteolytic enzyme. For example, reaction of the $\epsilon$-amino group of lysine with ethyltrifluorothioacetate in mildly basic solution yields a blocked amino acid residue whose adjacent peptide bond is no longer susceptible to hydrolysis by trypsin. Goldberger et al., *Biochemistry* 1:401, 1962). Treatment of such a polypeptide with trypsin thus cleaves only at the arginyl residues.

Polypeptides also can be modified to create peptide linkages that are susceptible to proteolytic enzyme-catalyzed hydrolysis. For example, alkylation of cysteine residues with $\beta$-haloethylamines yields peptide linkages that are hydrolyzed by trypsin. (Lindley, *Nature* 178:647, 1956).

In addition, chemical reagents that cleave polypeptide chains at specific residues can be used. (Witcop, *Adv. Protein Chem.* 16:221, 1961). For example, cyanogen bromide cleaves polypeptides at methionine residues. (Gross & Witkip, *J. Am. Chem. Soc.* 83: 1510, 1961).

Thus, by treating a metabotropic glutamate receptor, or fragments thereof, with various combinations of modifiers, proteolytic enzymes and/or chemical reagents, numerous discrete overlapping peptides of varying sizes are generated. These peptide fragments can be isolated and purified from such digests by chromatographic methods. Alternatively, fragments can be synthesized using an appropriate solid-state synthetic procedure.

Fragments may be selected to have desirable biological activities. For example, a fragment may include just a ligand binding site. Such fragments are readily identified by those of ordinary skill in the art using routine methods to detect specific binding to the fragment. For example, in the case of a metabotropic glutamate receptor, nucleic acid encoding a receptor fragment can be expressed to produce the polypeptide fragment which is then contacted with a receptor ligand under appropriate association conditions to determine whether the ligand binds to the fragment. Such fragments are useful in screening assays for agonists and antagonists of glutamate, and for therapeutic effects where it is useful to remove glutamate from serum, or other bodily tissues.

Other useful fragments include those having only the external portion, membrane-spanning portion, or intracellular portion of the receptor. These portions are readily identified by comparison of the amino acid sequence of the receptor with those of known receptors, or by other standard methodology. These fragments are useful for forming chimeric receptors with fragments of other receptors to create a receptor with an intracellular portion which performs a desired function within that cell, and an extracellular portion which causes that cell to respond to the presence of glutamate, or those agonists or antagonists described herein. Chimeric receptor genes when appropriately formulated are useful in genetic therapies for a variety of diseases involving dysfunction of receptors or where modulation of receptor function provides a desirable effect in the patient.

Additionally, chimeric receptors can be constructed such that the intracellular domain is coupled to a desired enzymatic process which can be readily detected by calorimetric, radiometric, luminometric, spectrophotometric or fluorimetric assays and is activated by interaction of the extracellular portion with its native ligand (e.g., glutamate) or agonist and/or antagonists of the invention. Cells expressing such chimeric receptors can be used to facilitate screening of metabotropic glutamate receptor agonists and antagonists, and in some cases inorganic ion receptor agonists and antagonists.

Thus, this invention also provides fragments, or purified polypeptides of calcium receptors, metabotropic glutamate receptors, or chimeric receptors including calcium receptor sequences and metabotropic glutamate receptor sequences. The fragments may be used to screen for compounds that are active at either metabotropic glutamate or calcium receptors. For example, a fragment including the extracellular domain of a calcium receptor or a metabotropic glutamate receptor may be used in a soluble receptor binding assay to identify which molecules in a combinatorial library can bind the receptor within the region assayed. Such "binding" molecules may be predicted to affect the function of the receptor. Preferred receptor fragments include those having functional receptor activity, a binding site, epitope for antibody recognition (typically at least six amino acids), and/or a site which binds a metabotropic glutamate receptor agonist, antagonist or modulator. Other preferred receptor fragments include those having only an extracellular portion, a transmembrane portion, an intracellular portion, and/or a multiple transmembrane portion (e.g., seven transmembrane portion). Such receptor fragments have various uses such as being used to obtain antibodies to a particular region and being used to form chimeric receptors and fragments of other receptors to create a new receptor having unique properties.

The purified polypeptides or fragments preferably have at least six contiguous amino acids of a metabotropic glutamate receptor or calcium receptor or chimeric receptor. By "purified" in reference to a polypeptide is meant that the polypeptide is in a form (i.e., its association with other molecules) distinct from naturally occurring polypeptide. Preferably, the polypeptide is provided as a substantially purified preparation representing at least 75%, more preferably 85%, most preferably 95%, of the total protein in the preparation.

In many applications, it is preferable that the purified polypeptide or fragment have more than 6 contiguous amino acids from the metabotropic glutamate receptor or calcium receptor or chimeric receptor. For example, the purified polypeptide can have at least 12, 18, 14, 30, or 36 contiguous amino acids of the "parent" receptor.

Other fragments may be prepared which include only the seven transmembrane domain and the cytoplasmic tail domain of calcium receptors, metabotropic glutamate receptors, or chimeric receptors. Such fragments may be useful, for example, in functional assays to screen for compounds whose site of action is at the seven transmembrane domain.

As indicated above, the invention provides methods of screening for a compound that binds to a receptor, which utilizes receptor fragments. In one example, the method includes the steps of: preparing a nucleic acid sequence encoding a fragment of a receptor; inserting the sequence into a replicable expression vector capable of expressing said fragment in a host cell; transforming a host cell with the vector; recovering the fragment from the host cell; introducing fragment and a test compound into an acceptable medium; and monitoring the binding of the compound to the fragment by physically detectable means. In cases in which the receptor is a metabotropic glutamate receptor, the fragment preferably includes an extracellular domain of the metabotropic glutamate receptor, or a seven transmembrane domain of the metabotropic glutamate receptor, or a seven transmembrane domain and a cytoplasmic tail domain of a metabotropic glutamate receptor. In cases in which the receptor is a calcium receptor, the fragment preferably includes an extracellular domain of the calcium receptor, a seven transmembrane domain of the calcium receptor, or a seven transmembrane domain and a cytoplasmic tail domain of a calcium receptor.

Certain fragments of metabotropic glutamate receptors and calcium receptors retain the functions of activating one or more of the cellular responses normally activated by the "parent" receptor when contacted with a compound which interacts. Thus, for example, a cellular expressed fragment which includes the 7TMD and CT of an mGluR or a CaR, but do not include the ECD, may activate a cellular response (s) when contacted with a compound which interacts with the 7TMD. Thus, incorporation of such fragments in a cell-based method of screening for compounds which bind to or modulate a metabotropic glutamate receptor or calcium receptor, such as that described herein for chimeric receptors, is useful to identify active compounds which interact with the fragment rather that the deleted sequence.

Isolated fragments of calcium receptors, metabotropic glutamate receptors, or chimeric receptors comprising calcium receptor sequences and metabotropic glutamate receptor sequences may be combined in an in vitro functional assay to screen for compounds active at either receptor. Such an in vitro assay, for example, may include a fragment having the extracellular domain of one receptor and a fragment having the seven transmembrane domain and the cytoplasmic tail domain of the other receptor, where the extracellular domain will complement the seven transmembrane/cytoplasmic tail domain fragment in vitro. In this way functional chimeric receptors which are useful in a screening assay may be prepared without the need for recombination of the nucleic acids encoding them. Instead, these functional chimeric receptors may be achieved by combining, in vitro, portions of different receptors.

Such combinations of fragments provide methods of screening for compounds which bind to or modulate a receptor. An example of such a method includes the steps of: preparing a nucleic acid sequence encoding a first fragment which is a fragment of a first receptor; inserting the sequence into a replicable expression vector capable of expressing that fragment in a host cell; transforming a host cell with the vector; recovering the fragment from the host cell; preparing a nucleic acid sequence encoding a second fragment which is a fragment of a second receptor; inserting the sequence into a replicable expression vector capable of expressing the second fragment in a host cell; transforming a host cell with the vector; recovering the second fragment from the host cell, introducing both the first fragment and the second fragment into an acceptable medium, and monitoring the binding and modulation of the compound by physically detectable means.

In particular preferred examples, the first fragment includes the extracellular domain of a metabotropic glutamate receptor and the second fragment includes the seven transmembrane domain and the cytoplasmic tail domain of a calcium receptor; the first fragment includes the extracellular domain of a calcium receptor and the second fragment includes the seven transmembrane domain and the cytoplasmic tail domain of a metabotropic glutamate receptor; or the first fragment includes the extracellular domain of a calcium receptor and the second fragment includes the seven transmembrane domain of a metabotropic glutamate receptor and the cytoplasmic tail domain of a calcium receptor.

D. Screening Procedures to Identify Compounds which Modulate Metabotropic Glutamate Receptor Activities Using Chimeric Receptors The mGluR agonist and antagonist compounds described in the scientific literature are related to the endogenous agonist, glutamate (for reviews see: Cockcroft et al., *Neurochem. Int.* 23:583–594, 1993; Schoepp and Conn, *TIPS* 14:13–20, 1993; Hollmann and Heinemann, *Annu. Rev. Neurosci.* 17:31–108, 1994). Such agonist and antagonist compounds have an acidic moiety, usually a carboxylic acid, but sometimes a phosphatidic acid. Presumably then, such compounds bind mGluRs at the same site as the amino acid, glutamate. This has been confirmed for methylcarboxyphenylglycine, which was shown to be a competitive antagonist of glutamate (Eaton et al., *Eur. J. Pharm.—Mol. Pharm. Sect.* 244:195–197, 1993). It can be assumed that compounds active at mGluRs, lacking negative charges, and not resembling the amino acid glutamate, may not act at the glutamate binding site.

Compounds targeted to the metabotropic glutamate receptor have several uses including diagnostic uses and therapeutic use. The syntheses of many of the compounds is described by Nemeth et al., entitled "Calcium Receptor Active Molecule" International Publication Number WO 93/04373, hereby incorporated by reference herein. Those compounds binding to a metabotropic glutamate receptor and those compounds efficacious in modulating metabotropic receptor glutamate activity can be identified using the procedures described herein. Those compounds which can selectively bind to the metabotropic glutamate receptor can be used diagnostically to determine the presence of the metabotropic glutamate receptor versus other glutamate receptors.

The following is a description of procedures which can be used to obtain compounds modulating metabotropic glutamate receptor activity. Various screening procedures can be carried out to assess the ability of a compound to modulate activity of chimeric receptors of the invention by measuring its ability to have one or more activities of a metabotropic glutamate receptor modulating agent or a calcium receptor modulating agent. In cells expressing chimeric receptors of the invention, such activities include the effects on intracellular calcium, inositol phosphates and cyclic AMP.

Measuring $[Ca^{2+}]_i$ with fura-2 provides a very rapid means of screening new organic molecules for activity. In a single afternoon, 10–15 compounds (or molecule types) can be examined and their ability to mobilize or inhibit mobilization of intracellular $Ca^{2+}$ can be assessed by a single experiment. The sensitivity of observed increases in $[Ca^{2+}]_i$ to depression by PMA can also be assessed.

For example, recombinant cells expressing chimeric receptors of the invention loaded with fura-2 are initially suspended in buffer containing 0.5 mM $CaCl_2$. A test substance is added to the cuvette in a small volume (5–15 $\mu$l) and changes in the fluorescence signal are measured. Cumulative increases in the concentration of the test substance are made in the cuvette until some predetermined concentration is achieved or no further changes in fluorescence are noted. If no changes in fluorescence are noted, the molecule is considered inactive and no further testing is performed.

In the initial studies, molecules may be tested at concentrations as high as 5 or 10 mM. As more potent molecules became known, the ceiling concentration was lowered. For example, newer molecules are tested at concentrations no greater than 500 $\mu$M. If no changes in fluorescence are noted at this concentration, the molecule can be considered inactive.

Molecules causing increases in $[Ca^{2+}]_i$ are subjected to additional testing. Two characteristics of a molecule which can be considered in screening for a positive modulating agent of a chimeric receptor of the invention are the mobilization of intracellular $Ca^{2+}$ and sensitivity to PKC activators.

A single preparation of cells can provide data on $[Ca^{2+}]_i$, cyclic AMP levels, $IP_3$ and other intracellular messengers. A typical procedure is to load cells with fura-2 and then divide the cell suspension in two; most of the cells are used for measurement of $[Ca^{2+}]_i$ and the remainder are incubated with molecules to assess their effects on cyclic AMP.

Measurements of inositol phosphates are a time-consuming aspect of the screening. However, ion-exchange columns eluted with chloride (rather than formate) provide a very rapid means of screening for $IP_3$ formation, since rotary evaporation (which takes around 30 hours) is not required. This method allows processing of nearly 100 samples in a single afternoon by a single experimenter. Those molecules that prove interesting, as assessed by measurements of $[Ca^{2+}]_i$, cyclic AMP, and $IP_3$ can be subjected to a more rigorous analysis by examining formation of various inositol phosphates and assessing their isomeric form by HPLC.

The following is illustrative of methods useful in these screening procedures.

1. Measurement of cyclic AMP

This section describes measuring cyclic AMP levels. Cells were incubated as above and at the end of the incubation, a 0.15-ml sample was taken and transferred to 0.85 ml of hot (70° C.) water and heated at this temperature for 5–10 minutes. The tubes were subsequently frozen and thawed several times and the cellular debris sedimented by centrifugation. Portions of the supernatant were acetylated and cyclic AMP concentrations determined by radioimmunoassay.

2. Measurement of Inositol Phosphate Formation

This section describes procedures measuring inositol phosphate formation. Membrane phospholipids were labeled by incubating parathyroid cells with 4 μCi/ml $^3$H-myo-inositol for 20–24 hours. Cells were then washed and resuspended in PCB containing 0.5 mM $CaCl_2$ and 0.1% BSA. Incubations were performed in microfuge tubes in the absence or presence of various concentrations of organic polycation for different times. Reactions were terminated by the addition of 1 ml chloroform-methanol-12 N HCl (200:100:1; v/v/v). Aqueous phytic acid hydrolysate (200 μl; 25 μg phosphate/tube). The tubes were centrifuged and 600 μl of the aqueous phase was diluted into 10 ml water.

Inositol phosphates were separated by ion-exchange chromatography using AG1-X8 in either the chloride- or formate-form. When only $IP_3$ levels were to be determined, the chloride-form was used, whereas the formate form was used to resolve the major inositol phosphates ($IP_3$, $IP_2$, and $IP_1$). For determination of just $IP_3$, the diluted sample was applied to the chloride-form column and the column was washed with 10 ml 30 mM HCl followed by 6 ml 90 mM HCl and the $IP_3$ was eluted with 3 ml 500 mM HCl. The last eluate was diluted and counted. For determination of all major inositol phosphates, the diluted sample was applied to the formate-form column and $IP_1$, $IP_2$, and $IP_3$ eluted sequentially by increasing concentrations of formate buffer. The eluted samples from the formate columns were rotary evaporated, the residues brought up in cocktail, and counted.

The isomeric forms of IP3 were evaluated by HPLC. The reactions were terminated by the addition of 1 ml 0.45 M perchloric acid and stored on ice for 10 minutes. Following centrifugation, the supernatant was adjusted to pH 7–8 with $NaHCO_3$. The extract was then applied to a Partisil SAX anion-exchange column and eluted with a linear gradient of ammonium formate. The various fractions were then desalted with Dowex followed by rotary evaporation prior to liquid scintillation counting in a Packard Tri-carb 1500 LSC.

For all inositol phosphate separation methods, appropriate controls using authentic standards were used to determine if organic polycations interfered with the separation. If so, the samples were treated with cation-exchange resin to remove the offending molecule prior to separation of inositol phosphates.

3. Use of Lead Molecules

By systematically measuring the ability of a lead molecule to mimic or antagonize the effect of a natural ligand, the importance of different functional groups for agonists and antagonists can be identified. Of the molecules tested, some are suitable as drug candidates while others are not necessarily suitable as drug candidates. The suitability of a molecule as a drug candidate depends on factors such as efficacy and toxicity. Such factors can be evaluated using standard techniques. Thus, lead molecules can be used to demonstrate that the hypothesis underlying receptor-based therapies is correct and to determine the structural features that enable the receptor-modulating agents to act on the receptor and, thereby, to obtain other molecules useful in this invention.

The examples described herein demonstrate the general design of molecules useful as modulators of the activity of mGluRs and CaRs. The examples also describe screening procedures to obtain additional molecules, such as the screening of natural product libraries. Using these procedures, those of ordinary skill in the art can identify other useful modulators of mGluRs and CaRs.

Cell lines expressing calcium receptors have been obtained and methods applicable to their use in high throughput screening to identify compounds which modulate the activity of calcium receptors disclosed (See U.S. Ser. No. 08/353,784, filed Dec. 9, 1994, hereby incorporated by reference herein). Cell lines expressing metabotropic glutamate receptors have been obtained and methods applicable to their potential use to identify compounds which modulate activity of metabotropic glutamate receptors disclosed (European Patent Publication No. 0 568 384 A1; European Patent Publication No. 0 569 240 A1; PCT Publication No. WO 94/29449; and PCT Publication No. WO 92/10583). Thus, recombinant cell-based assays which use biochemical, spectrophotometric or other physical measurements to detect the modulation of activity of an expressed receptor, especially by measuring changes in affected intracellular messengers, are known to those in the art and can be constructed such that they are suitable for high throughput functional screening of compounds and compound libraries. It will be appreciated by those in the art that each functional assay has advantages and disadvantages for high throughput screening which will vary depending on the receptor of interest, the cell lines employed, the nature of the biochemical and physical measurements used to detect modulation of receptor function, the nature of the compound library being screened and various other parameters. An exceptionally useful and practical method is the use of fluorescent indicators of intracellular $Ca^{2+}$ to detect modulation of the activity of receptors coupled to phospholipase-C.

The use of [$^3$H]glutamate, or any other compound found to modulate the mGluR discovered by the methods described herein, as a lead compound is expected to result in the discovery of other compounds having similar or more potent activity which in turn can be used as lead compounds. Lead compounds such as [$^3$H]glutamate can be used for molecular modeling using standard procedures and to screen compound libraries. Radioligand binding techniques [a radio labeled binding assay] can be used to identify compounds binding at the glutamate binding site. While such binding assays are useful for finding new compounds binding to the glutamate binding site on mGluR's, the current invention provides for the discovery of novel compounds with unique and useful activities at mGluR's which can be radio labeled and used similarly in Radioligand assays to find additional compounds binding to the new lead defined site. This screening test allows vast numbers of potentially useful compounds to be screened for their ability to bind to the glutamate binding site. Other rapid assays for detection of binding to the glutamate binding site on metabotropic glutamate receptors can be devised using standard detection techniques. Other compounds can be identified which act at the glutamate binding using the procedures described in this section. A high-throughput assay is first used to screen product libraries (e.g., natural product libraries and compound files) to identify compounds with activity at the glutamate (or lead compound) binding site. These compounds are then utilized as chemical lead structures for a drug development program targeting the glutamate or lead compound binding site on metabotropic glutamate receptors. Routine experiments, including animal studies can be performed to identify those compounds having the desired activities.

The following assay can be utilized as a high-throughput assay. Rat brain membranes are prepared according to the method of Williams et al. (*Molec. Pharmacol.* 36:575, 1989), with the following alterations: Male Sprague-Dawley rats (Harlan Laboratories) weighing 100–200 g are sacrificed by decapitation. The cortex or cerebellum from 20 rats are cleaned and dissected. The resulting brain tissue is homogenized at 4° C. with a polytron homogenizer at the lowest setting in 300 ml 0.32 M sucrose containing 5 mM K-EDTA (pH 7.0). The homogenate is centrifuged for 10 min at 1,000×g and the supernatant removed and centrifuged at 30,000×g for 30 minutes. The resulting pellet is resuspended in 250 ml 5 mM K-EDTA (pH 7.0) stirred on ice for 15 minutes, and then centrifuged at 30,000×g for 30 minutes. The pellet is resuspended in 300 ml 5 mM K-EDTA (pH 7.0) and incubated at 32° C. for 30 minutes. The suspension is then centrifuged at 100,000×g for 30 minutes. Membranes are washed by resuspension in 500 ml 5 mM K-EDTA (pH 7.0), incubated at 32° C. for 30 minutes, and centrifuged at 100,000×g for 30 minutes. The wash procedure, including the 30-minute incubation, is repeated. The final pellet is resuspended in 60 ml 5 mM K-EDTA (pH 7.0) and stored in aliquots at −80° C.

To perform a binding assay with [$^3$H]glutamate (as an example of a lead compound), aliquots of SPMs (synaptic plasma membranes) are thawed, resuspended in 30 ml of 30 mM EPPS/1 mM K-EDTA, pH 7.0, and centrifuged at 100,000×g for 30 minutes. SPMs are resuspended in buffer A (30 mM EPPS/1 mM K-EDTA, pH 7.0). The [$^3$H]-glutamate is added to this reaction mixture. Binding assays are carried out in polypropylene test tubes. The final incubation volume is 500 μl. Nonspecific binding is determined in the presence of 100 μM nonradioactive glutamate. Duplicate samples are incubated at 0° C. for 1 hour. Assays are terminated by adding 3 ml of ice-cold buffer A, followed by filtration over glass-fiber filters (Schleicher & Schuell No. 30) that are presoaked in 0.33% polyethyleneimine (PEI). The filters are washed with another 3×3 ml of buffer A, and radioactivity is determined by scintillation counting at an efficiency of 35–40% for $^3$H.

In order to validate the above assay, the following experiments can also be performed:

(a) The amount of nonspecific binding of the [$^3$H] glutamate to the filters is determined by passing 500 μl of buffer A containing various concentrations of [$^3$H] glutamate through the presoaked glass-fiber filters. The filters are washed with another 4×3 ml of buffer A, and radioactivity bound to the filters is determined by scintillation counting at an efficiency of 35–40% for $^3$H.

(b) A saturation curve is constructed by resuspending SPMs in buffer A. The assay buffer (500 μl) contains 60 μg of protein. Concentrations of [$^3$H]glutamate are used, ranging from 1.0 nM to 400 μM in half-log units. A saturation curve is constructed from the data, and an apparent $K_D$ value and $B_{max}$ value determined by Scatchard analysis (Scatchard, Ann. N.Y. Acad. Sci. 51: 660, 1949). The cooperativity of binding of the [$^3$H] glutamate is determined by the construction of a Hill plot (Hill, J. Physiol. 40:190, 1910).

(c) The dependence of binding on protein (receptor) concentration is determined by resuspending SPMs in buffer A. The assay buffer (500 μl) contains a concentration of [$^3$H]glutamate equal to its $K_D$ value and increasing concentrations of protein. The specific binding of [$^3$H]glutamate should be linearly related to the amount of protein (receptor) present.

(d) The time-course of ligand-receptor binding is determined by resuspending SPMs in buffer A. The assay buffer (500 μl) contains a concentration of [$^3$H] glutamate equal to its $K_D$ value and 100 μg of protein. Duplicate samples are incubated at 0° C. for varying lengths of time; the time at which equilibrium is reached is determined, and this time point is routinely used in all subsequent assays.

(e) The pharmacology of the binding site can be analyzed by competition experiments. In such experiments, the concentration of [$^3$H]glutamate and the amount of protein are kept constant, while the concentration of test (competing) drug is varied. This assay allows for the determination of an $IC_{50}$ and an apparent $K_D$ for the competing drug (Cheng and Prusoff, J. Biochem. Pharmacol. 22:3099, 1973). The cooperativity of binding of the competing drug is determined by Hill plot analysis.

Specific binding of the [$^3$H]glutamate represents binding to the glutamate binding site on metabotropic glutamate receptors. As such, analogs of glutamate should compete with the binding of [$^3$H]glutamate in a competitive fashion, and their potencies in this assay should correlate with their potencies in a functional assay of metabotropic glutamate receptor activity (e.g., electrophysiological assessment of the activity of cloned metabotropic glutamate receptors expressed in Xenopus oocytes). Conversely, compounds which have activity at the sites other that the glutamate binding site should not displace [$^3$H]glutamate binding in a competitive manner. Rather, complex allosteric modulation of [$^3$H]glutamate binding, indicative of noncompetitive interactions, might occur.

(f) Studies estimating the dissociation kinetics are performed by measuring the binding of [$^3$H]glutamate after it is allowed to come to equilibrium (see (d) above), and a large excess of nonradioactive competing drug is added to the reaction mixture. Binding of the [$^3$H]glutamate is then assayed at various time intervals. With this assay, the association and dissociation rates of binding of the [$^3$H]glutamate are determined (Titeler, Multiple Dopamine Receptors: Receptor Binding Studies in Dopamine Pharmacology. Marcel Dekker, Inc., New York, 1983). Additional experiments involve varying the reaction temperature (0° C. to 37° C.) in order to understand the temperature dependence of this parameter.

The following is one example of a rapid screening assay to obtain compounds modulating metabotropic glutamate receptor activity. The screening assay first measures the ability of compounds to bind to recombinant receptors, or receptor fragments containing the glutamate binding site. Compounds binding to the metabotropic glutamate receptor are then tested for their ability to modulate one or more activities at a metabotropic glutamate receptor.

In one procedure, a cDNA or gene clone encoding the chimeric receptor or fragment of a metabotropic glutamate receptor from a suitable organism such as a human is obtained using standard procedures. Distinct fragments of the clone are expressed in an appropriate expression vector to produce the smallest receptor polypeptide(s) obtainable able to bind glutamate. In this way, the polypeptide(s) containing the glutamate binding site is identified. Such experiments can be facilitated by utilizing a stably transfected mammalian cell line (e.g., HEK 293 cells) expressing metabotropic glutamate receptors.

Alternatively, the metabotropic glutamate receptor can be chemically reacted with glutamate chemically modified SO that amino acid residues of the metabotropic glutamate receptor which contact (or are adjacent to) the selected compound are modified and thereby identifiable. The fragment(s) of the metabotropic glutamate receptor containing those amino acids which are determined to interact with glutamate and are sufficient for binding to glutamate, can then be recombinantly expressed using standard techniques.

The recombinant polypeptide(s) having the desired binding properties can be bound to a solid-phase support using standard chemical procedures. This solid-phase, or affinity matrix, may then be contacted with glutamate to demonstrate that this compound can bind to the column, and to identify conditions by which the compound may be removed from the solid-phase. This procedure may then be repeated using a large library of compounds to determine those compounds which are able to bind to the affinity matrix. Bound compounds can then can be released in a manner similar to glutamate. Alternative binding and release conditions may be utilized to obtain compounds capable of binding under conditions distinct from those used for glutamate binding (e.g., conditions which better mimic physiological conditions encountered especially in pathological states). Compounds binding to the glutamate binding site can thus be selected from a very large collection of compounds present in a liquid medium or extract.

In an alternate method, chimeric receptors are bound to a column or other solid phase support. Those compounds which are not competed off by reagents binding to the glutamate binding site on the receptor can then be identified. Such compounds define alternative binding sites on the receptor. Such compounds may be structurally distinct from known compounds and may define chemical classes of agonists or antagonists which may be useful as therapeutics agents.

Modulating metabotropic glutamate receptor activity causes an increase or decrease in a cellular response which occurs upon metabotropic glutamate receptor activation. Cellular responses to metabotropic glutamate receptor activation vary depending upon the type of metabotropic glutamate receptor activated. Generally, metabotropic glutamate receptor activation causes one or more of the following activities: (1) increase in PI hydrolysis; (2) activation of phospholipase C; (3) increases and decreases in the formation of cyclic adenosine monophosphate (cAMP); (4) decrease in the formation of cAMP; (5) changes in ion channel function; (6) activation of phospholipase D; (7) activation or inhibition of adenylyl cyclase; (8) activation of guanylyl cyclase; (9) increases in the formation of cyclic guanosine monophosphate (cGMP); (10) activation of phospholipase $A_2$; (11) increases in arachidonic acid release; (12) increases or decreases in the activity of voltage- and ligand-gated ion channels; (13) and increase in intracellular calcium. Inhibition of metabotropic glutamate receptor activation prevents one or more of these activities from occurring.

Activation of a particular metabotropic glutamate receptor refers to an event which subsequently causes the production of one or more activities associated with the type of receptor activated. Activation of mGluR1 can result in one or more of the following activities: increase in PI hydrolysis, increase in cAMP formation, increase in intracellular calcium ($Ca^{2+}$) and increase in arachidonic acid formation. Compounds can modulate one or more metabotropic glutamate receptor activities by acting as an agonist or antagonist of glutamate binding site activation.

The chimeric receptors of the present invention provide a method of screening for compounds active at mGluRs by the detection of signals produced by CaRs. The chimeric receptors may be used in the screening procedures described in PCT/US93/01642 (WO94/18959), which are hereby incorporated by reference herein, including methods of screening using fura-2, and measurement of cytosolic $Ca^{2+}$ using cell lines expressing calcium receptors and methods of screening using oocyte expression.

Active compounds identified by the screening methods described herein, may be useful as therapeutic molecules to modulate metabotropic glutamate receptor activity or as a diagnostic agents to diagnose those patients suffering from a disease characterized by an abnormal metabotropic glutamate receptor activity. Preferably the screening methods are used to identify metabotropic glutamate receptor modulators by screening potentially useful molecules for an ability to mimic or block an activity of extracellular glutamate or other metabotropic glutamate receptor agonists on a cell having a metabotropic glutamate receptor and determining whether the molecule has an $EC_{50}$ $IC_{50}$ of less than or equal to 100 µM. More preferably, the molecules tested for its ability to mimic or block an increase in $[Ca^{2+}]_i$ elicited by extracellular glutamate or other mGluR agonists.

Identification of metabotropic glutamate receptor-modulating agents is facilitated by using a high-throughput screening system. High-throughput screening allows a large number of molecules to be tested. For example, a large number of molecules can be tested individually using rapid automated techniques or in combination using a combinatorial library. Individual compounds able to modulate metabotropic glutamate receptor activity present in a combinatorial library can be obtained by purifying and retesting fractions of the combinatorial library. Thus, thousands to millions of molecules can be screened in a single day. Active molecules can be used as models to design additional molecules having equivalent or increased activity. Preferably the identification method uses a recombinant chimeric metabotropic glutamate receptor. Chimeric receptors can be introduced into different cells using a vector encoding a receptor. Preferably, the activity of molecules in different cells is tested to identify a metabotropic glutamate receptor agonist or metabotropic glutamate receptor antagonist molecule which mimics or blocks one or more activities of glutamate at a first type of metabotropic glutamate receptor but not at a second type of metabotropic glutamate receptor.

As indicated above, the present invention provides a novel method of screening for compounds which modulate metabotropic glutamate receptor activity, by using a chimeric receptor having portions of a metabotropic glutamate receptor and portions of a calcium receptor. In particular receptors of this type, the signaling process of the calcium receptor portion is used to detect modulation of mGluR activity, as various compounds are tested for binding to the mGluR portion. The method of screening can be conducted in a variety of ways, such as utilizing chimeric receptors having different portions from the metabotropic glutamate receptor and calcium receptor. Certain preferred examples are described below.

In one example, the method of screening for a compound that binds to or modulates the activity of a metabotropic glutamate receptor involves preparing a chimeric receptor having an extracellular domain, a seven transmembrane domain, and an intracellular cytoplasmic tail domain. A sequence of at least 6 contiguous amino acids is the same as or homologous to a sequence from a metabotropic glutamate receptor and a sequence of at least 6 contiguous amino acids is the same as or homologous to a sequence from a calcium receptor. The chimeric receptor and a test compound are introduced into a acceptable medium, and the binding of the test compound to the receptor or the modulation of the receptor by the test compound is monitored by physically detectable means in order to identify such binding or modulating compounds. Generally, acceptable media will include those in which a natural ligand of an mGluR and/or a CaR will interact with an mGluR or a CaR.

Often it will be beneficial to use chimeric receptors which have longer sequences from one or both of the mGluR and the CaR. For example, the chimeric receptor can have a sequence of at least 12, 18, 24, 30, 36, or more amino acids the same as or homologous a sequence from one or both of the mGluR or CaR. In one useful chimeric receptor, one domain is homologous to a domain of a metabotropic glutamate receptor and at least one domain is homologous to a domain of a calcium receptor In a second example, the method of screening for a compound which binds to or modulates the activity of a metabotropic glutamate receptor utilizes a nucleic acid sequence which encodes a chimeric receptor. The nucleic acid is expressed in a cell, and binding or modulation by a test compound is observed by monitoring the effects of the test compound on the cell. Thus, generally the method includes preparing a nucleic acid sequence encoding a chimeric receptor. The encoded chimeric receptor has an extracellular domain, a seven transmembrane domain, and an intracellular cytoplasmic tail domain. As in the example above, the chimeric receptor has sequences of at least 6 contiguous amino acids which are the same as or homologous to sequences from each of an mGluR and a CaR. Also as indicated above, the sequences from one or both of the mGluR and the CaR may beneficially be longer in particular applications, e.g., at least 12, 18, 24, 30, 36, or more amino acids in length. The nucleic acid sequence is inserted into a replicable expression vector capable of expressing the chimeric receptor in a host cell, and a host cell is transformed with the vector. The transformed host cell and a test compound are introduced into an acceptable medium and the effect of the compound on the host cell is monitored (such as be techniques or assays described above). Preferably, though not necessarily, the host cell is a eukaryotic cell.

The amino acid sequences of the chimeric receptor can be selected in a variety of combinations in particular cases. Thus, a chimeric receptor can include at least one domain which is homologous to a domain of a metabotropic glutamate receptor and at least one domain which is homologous to a domain of a calcium receptor. A domain(s) of the chimeric receptor can, for example, be homologous the extracellular domain and/or the seven transmembrane domain of a metabotropic glutamate receptor.

Likewise, a chimeric receptor which has three cytoplasmic loops can have at least one loop homologous to a cytoplasmic loop of an mGluR, or at least one loop homologous to a cytoplasmic loop of a CaR, or at least one loop homologous to a cytoplasmic loop of each of the those receptors.

Similarly, in other chimeric receptors, there is a portion of the receptor which is homologous to a sequence of one type of receptor (CaR or mGluR), while the remainder of the chimeric receptor is homologous to the other type of receptor (CaR or mGluR). Thus, the chimeric receptor can have a sequence of at least 6, 12, 18, 24, 30, 36, or more contiguous amino acids which is homologous to a sequence of one of the receptor types with the remainder of the sequence of the chimeric receptor homologous to a sequence from the other receptor type. This further includes cases in which at least one cytoplasmic loop is from one of the receptor types, or at least one domain is from one of the receptor types.

Other combinations of sequences will also be useful in particular applications.

The chimeric metabotropic glutamate/calcium receptors can also be used to screen for compounds active at both metabotropic glutamate receptors and calcium receptors. This is particularly useful for screening for compounds which interact at different domains or subdomains in an mGluR than in a CaR. Thus, such chimeras are useful for screening for compounds which, for example, act within the extracellular domain of a metabotropic glutamate receptor and also act within the seven transmembrane domain or the cytoplasmic tail domain of a calcium receptor. Such a chimera would include the extracellular domain of a metabotropic glutamate receptor linked to the seven transmembrane domain and cytoplasmic tail of a calcium receptor.

To screen for such compounds, active at both metabotropic glutamate receptors and calcium receptors, compounds would be screened according to the various methods of the present invention, against the chimeric receptor, the calcium receptor, and the metabotropic glutamate receptor. Compounds active at the seven transmembrane domain of the calcium receptor portion of the chimeric receptor should also be active when tested against the calcium receptor itself. A preferred method of screening for such compounds is to first screen them according to the methods of the present invention against a chimeric molecule having the extracellular domain of the metabotropic glutamate receptor, and the seven transmembrane and cytoplasmic tail domains of the calcium receptor and to then screen the positive compounds against both chimeric molecule having the extracellular and seven transmembrane domains of the metabotropic glutamate receptor and the cytoplasmic tail domain of the calcium receptor, and the calcium receptor itself. Compounds active at both molecules will be positive when tested against all three chimeric receptors.

Conversely, a chimera including the extracellular domain of a calcium receptor linked to the seven transmembrane domain and cytoplasmic tail of a metabotropic glutamate receptor would be useful in screening for compounds that act within the extracellular domain of a calcium receptor and also act within the seven transmembrane domain or the cytoplasmic tail of a metabotropic glutamate receptor. Preferably, the chimeric receptor, which includes the extracellular domain of a calcium receptor and the seven transmembrane domain and the cytoplasmic tail of a metabotropic glutamate receptor, is further modified to include portions of the cytoplasmic tail of a calcium receptor. This more preferred embodiment would thereby obtain the superior signaling properties of the calcium receptor while still being useful for screening for compounds that act at both the calcium receptor and the metabotropic glutamate receptor.

Thus in one aspect the invention features a method of screening for compounds active at both a metabotropic glutamate receptor and a calcium receptor, by preparing a nucleic acid sequence encoding a chimeric receptor. The chimeric receptor has an extracellular domain, a seven transmembrane domain, and an intracellular cytoplasmic tail domain, and at least one domain is homologous to a domain of the metabotropic glutamate receptor and at least one domain is homologous to a domain of a calcium receptor. The nucleic acid sequence is inserted into a replicable expression vector capable of expressing said chimeric receptor in a host cell, and a host cell is transformed with the vector. The transformed host cell and a test compound are introduced into an acceptable medium, and the effect of the test compound on the cell are monitored.

In general, for each of the above screening methods using chimeric receptors, the portion of the chimeric receptor homologous to an mGluR and the portion homologous to a CaR are selected to provide the binding, modulation, and/or signal coupling characteristics appropriate for a particular application.

E. Site of Action

The chimeric receptor molecules are also useful in methods for determining the site-of-action of compounds already identified as metabotropic glutamate receptor or calcium receptor active compounds. For example, chimeras including the extracellular domain of a metabotropic glutamate receptor linked to the seven transmembrane domain and cytoplasmic tail of a calcium receptor, as well as chimeras including the extracellular domain of a calcium receptor linked to the seven transmembrane domain and cytoplasmic tail of a metabotropic glutamate receptor would be useful in determining the site-of-action of either metabotropic glutamate receptor or calcium receptor active compounds. Those of ordinary skill in the art will recognize that these are two examples of large sequence exchanges and that much smaller sequence exchanges may also be employed to further refine the determination of the site-of-action.

Thus, the invention provides a method of determining the site-of-action of a metabotropic glutamate receptor active compound by: preparing a nucleic acid sequence encoding a chimeric receptor wherein the chimeric receptor comprises at least a 6 amino acid sequence which is homologous to a sequence of amino acids of a calcium receptor and the remainder of the amino acid sequence is homologous to a sequence of amino acids of a metabotropic glutamate receptor; inserting the sequence into a replicable expression vector capable of expressing the chimeric receptor in a host cell; transforming a host cell with the vector; introducing the transformed host cell and the compound into an acceptable medium; and monitoring the effect of the compound on the cell.

As indicated above for methods of screening, in particular applications it is advantageous to use sequence exchanges of different sizes. Thus, in other applications, the sequence homologous to a sequence from a calcium receptor, may for example, be at least 12, 18, 24, 30, 36, or more amino acids in length.

Conversely, a method of determining the site-of-action of a calcium receptor active compound can be performed in the same manner as described above, but using a nucleic acid encoding a chimeric receptor which includes at least a 6 amino acid sequence which is homologous to a sequence of amino acids of a metabotropic glutamate receptor and the remainder of the amino acid sequence is homologous to a sequence of amino acids of a calcium receptor. Also similar to the method above, the sequence homologous to a sequence from a metabotropic glutamate receptor can be of different lengths in various applications, for example, at least 12, 18, 24, 30, 36, or more amino acids in length.

F. Modulation of Metabotropic Glutamate Receptor Activity

Modulation of metabotropic glutamate receptor activity can be used to produce different effects such as anticonvulsant effects, neuroprotectant effects, analgesic effects, cognition-enhancement effects, and muscle-relaxation effects. Each of these effects has therapeutic applications. Compounds used therapeutically should have minimal side effects at therapeutically effective doses.

The ability of a compound to modulate metabotropic glutamate activity can be determined using electrophysiological and biochemical assays measuring one or more metabotropic glutamate activities. In general, such assays can be carried out using cells expressing the metabotropic glutamate receptor(s) of interest, but the assays can also be carried out using cells expressing a chimeric receptors of this invention which modulates the cellular activity which is to be monitored. Examples of such assays include the electrophysiological assessment of metabotropic glutamate receptor function in Xenopus oocytes expressing cloned metabotropic glutamate receptors, the electrophysiological assessment of metabotropic glutamate receptor function in transfected cell lines (e.g., CHO cells, HEK 293 cells, etc.) expressing cloned metabotropic glutamate receptors, the biochemical assessment of PI hydrolysis and cAMP accumulation in transfected cell lines expressing cloned metabotropic glutamate receptors, the biochemical assessment of PI hydrolysis and cAMP accumulation in rat brain (e.g., hippocampal, cortical, striatal, etc.) slices, fluorimetric measurements of cytosolic $Ca^{2+}$ in cultured rat cerebellar granule cells, and fluorimetric measurements of cytosolic $Ca^{2+}$ in transfected cell lines expressing cloned metabotropic glutamate receptors.

Prior to therapeutic use in a human, the compounds are preferably tested in vivo using animal models. Animal studies to evaluate a compound's effectiveness to treat different diseases or disorders, or exert an effect such as an analgesic effect, a cognition-enhancement effect, or a muscle-relaxation effect, can be carried out using standard techniques.

G. Novel Agents and Pharmaceutical Compositions

The chimeric receptors and screening methods described herein provide metabotropic glutamate receptor-binding agents (e.g., compounds and pharmaceutical compositions) discovered due to their ability to bind to a chimeric metabotropic glutamate receptor. Such binding agents are preferably modulators of a metabotropic glutamate receptor. Certain of these agent will be novel compounds identified by the screening methods described herein. In addition, other such compounds are derived by standard methodology from such identified compounds when such identified compounds are used as lead compounds in screening assays based on analogs of identified active compounds, or in medicinal chemistry developments using identified compounds as lead compounds.

Further, by providing novel and efficient screening methods using chimeric receptors, this invention provides a method for preparing a pharmaceutical agent active on a metabotropic glutamate receptor. Without such this efficient method, such agents would not be identified. The method involves identifying a active agent by screening using a chimeric receptor of the type described herein in a screening method as described above. The identified agent or an analog of that agent is synthesized in an amount sufficient to administer to a patient in a therapeutically effective amount.

H. Treatment of Diseases and Disorders

A preferred use of the compounds and methods of the present invention is in the treatment of neurological diseases and disorders. Patients suffering from a neurological disease or disorder can be diagnosed by standard clinical methodology.

Neurological diseases or disorders include neuronal degenerative diseases, glutamate excitotoxicity, global and focal ischemic and hemorrhagic stroke, head trauma, spinal cord injury, hypoxia-induced nerve cell damage, and epilepsy. These different diseases or disorders can be further medically characterized. For example, neuronal degenerative diseases include Alzheimer's disease and Parkinson's disease.

Another preferred use of the present invention is in the production of other therapeutic effects, such as analgesic effects, cognition-enhancement effects, or muscle-relaxation effects. The present invention is preferably used to produce one or more of these effects in a patient in need of such treatment.

Patients in need of such treatment can be identified by standard medical techniques. For example, the production of analgesic activity can be used to treat patients suffering from clinical conditions of acute and chronic pain including the following: preemptive preoperative analgesia; peripheral neuropathies such as occur with diabetes mellitus and multiple sclerosis; phantom limb pain; causalgia; neuralgias such as occur with herpes zoster; central pain such as that seen with spinal cord lesions; hyperalgesia; and allodynia.

In a method of treating a patient, a therapeutically effective amount of a compound which in vitro modulates the activity of a chimeric receptor having at least the extracellular domain of a metabotropic glutamate receptor is administered to the patient. Typically, the compound modulates metabotropic glutamate receptor activity by acting as an agonist or antagonist of glutamate binding site activation. Preferably, the patient has a neurological disease or a disorder, preferably the compound has an effect on a physiological activity. Such physiological activity can be convulsions, neuroprotection, neuronal death, neuronal development, central control of cardiac activity, waking, control of movements and control of vestibo ocular reflex.

Diseases or disorders which can be treated by modulating metabotropic glutamate receptor activity include one or more of the following types: (1) those characterized by abnormal glutamate homeostasis; (2) those characterized by an abnormal amount of an extracellular or intracellular messenger whose production can be affected by metabotropic glutamate receptor activity; (3) those characterized by an abnormal effect (e.g., a different effect in kind or magnitude) of an intracellular or extracellular messenger which can itself be ameliorated by metabotropic glutamate receptor activity; and (4) other diseases or disorders in which modulation of metabotropic glutamate receptor activity will exert a beneficial effect, for example, in diseases or disorders where the production of an intracellular or extracellular messenger stimulated by receptor activity compensates for an abnormal amount of a different messenger.

The compounds and methods can also be used to produce other effects such as an analgesic effect, cognition-enhancement effect, and a muscle-relaxant effect. A "patient" refers to a mammal in which modulation of an metabotropic glutamate receptor will have a beneficial effect. Patients in need of treatment involving modulation of metabotropic glutamate receptors can be identified using standard techniques known to those in the medical profession. Preferably, a patient is a human having a disease or disorder characterized by one more of the following: (1) abnormal glutamate receptor activity (2) an abnormal level of a messenger whose production or secretion is affected by metabotropic glutamate receptor activity; and (3) an abnormal level or activity of a messenger whose function is affected by metabotropic glutamate receptor activity.

By "therapeutically effective amount" is meant an amount of an agent which relieves to some extent one or more symptoms of the disease or disorder in the patient; or returns to normal either partially or completely one or more physiological or biochemical parameters associated with or causative of the disease.

More generally, this invention provides a method for modulating metabotropic glutamate receptor activity by providing to a cell having a metabotropic glutamate receptor an amount of a metabotropic glutamate receptor-modulating molecule sufficient to either mimic one or more effects of glutamate at the metabotropic glutamate receptor, or block one or more effects of glutamate at the metabotropic glutamate receptor. The method can carried out in vitro or in vivo.

I. Formulation and Administration

Active compounds as identified by the methods of this invention can be utilized as pharmaceutical agents or compositions to treat different diseases and disorders as described above. In this context, a pharmacological agent or composition refers to an agent or composition in a form suitable for administration to a mammal, preferably a human.

The optimal formulation and mode of administration of compounds of the present invention to a patient depend on factors known in the art such as the particular disease or disorder, the desired effect, and the type of patient. While the compounds will typically be used to treat human patients, they may also be used to treat similar or identical diseases in other vertebrates such as other primates, farm animals such as swine, cattle and poultry, and sports animals and pets such as horses, dogs and cats.

Preferably, the therapeutically effective amount is provided as a pharmaceutical composition. A pharmacological agent or composition refers to an agent or composition in a form suitable for administration into a multicellular organism such as a human. Suitable forms, in part, depend upon the use or the route of entry, for example oral, transdermal, or by injection. Such forms should allow the agent or composition to reach a target cell whether the target cell is present in a multicellular host or in culture. For example, pharmacological agents or compositions injected into the blood stream should be soluble. Other factors are known in the art, and include considerations such as toxicity and forms which prevent the agent or composition from exerting its effect.

The claimed compositions can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. (See e.g., supra. PCT/US92/03736.) Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of a compound is dissolved in a suitable solvent, such as an aqueous or aqueous-alcohol solution, containing the appropriate acid and then isolated by evaporating the solution. In another example, a salt is prepared by reacting the free base and acid in an organic solvent.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, or transmucosally.

The compounds of the invention can be formulated for a variety of modes of administration, including systemic and topical or localized administration. Techniques and formulations generally may be found in *Remington's Pharmaceutical Sciences,* 18th Edition, Mack Publishing Co., Easton, PA, 1990.

For systemic administration, oral administration is preferred. For oral administration, the compounds are formulated into conventional oral dosage forms such as capsules, tablets and tonics.

Alternatively, injection may be used, e.g., intramuscular, intravenous, intraperitoneal, subcutaneous, intrathecal, or intracerebroventricular. For injection, the compounds of the invention are formulated in liquid solutions, preferably in physiologically compatible buffers such as Hank's solution or Ringer's solution. Alternatively, the compounds of the invention are formulated in one or more excipients (e.g., propylene glycol) that are generally accepted as safe as defined by USP standards. In addition, the compounds may be formulated in solid form and redissolved or suspended immediately prior to use. Lyophilized forms are also included.

Systemic administration can also be by transmucosal or transdermal means, or the molecules can be administered orally. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration may be, for example, through nasal sprays or using suppositories. For oral administration, the molecules are formulated into conventional oral administration dosage forms such as capsules, tablets, and liquid preparations.

For topical administration, the compounds of the invention are formulated into ointments, salves, gels, or creams, as is generally known in the art.

The amounts of various compounds to be administered can be determined by standard procedures. Generally, a therapeutically effective amount is between about 1 nmole and 3 $\mu$mole of the molecule, preferably 0.1 nmole and 1 $\mu$mole depending on its $EC_{50}$ or $IC_{50}$ and on the age and size of the patient, and the disease or disorder associated with the patient. Generally, it is an amount between about 0.1 and 50 mg/kg, preferably 0.01 and 20 mg/kg of the animal to be treated.

J. Transgenic Animals

The invention also provides transgenic, nonhuman mammals containing a transgene encoding a chimeric receptor, particularly a chimeric metabotropic glutamate receptor. Transgenic nonhuman mammals are particularly useful as an in vivo test system for studying the effects of introducing a chimeric receptor. Experimental model systems may be used to study the effects in cell or tissue cultures, in whole animals, or in particular cells or tissues within whole animals or tissue culture systems. The effects can be studied over specified time intervals (including during embryogenesis).

The present invention provides for experimental model systems for studying the physiological effects of the receptors. Model systems can be created having varying degrees of receptor expression. For example, the nucleic acid encoding a receptor may be inserted into cells which naturally express the parent receptors, such that the chimeric gene is expressed at much higher levels. Also, a recombinant gene may be used to inactivate the endogenous gene by homologous recombination, and thereby create a receptor deficient cell, tissue, or animal.

Inactivation of a gene can be caused, for example, by using a recombinant gene engineered to contain an insertional mutation (e.g., the neo gene). The recombinant gene is inserted into the genome of a recipient cell, tissue or animal, and inactivates transcription of the receptor. Such a construct may be introduced into a cell, such as an embryonic stem cell, by techniques such as transfection, transduction, and injection. Stem cells lacking an intact receptor sequence may generate transgenic animals deficient in the receptor.

Preferred test models are transgenic animals. A transgenic animal has cells containing DNA which has been artificially inserted into a cell and inserted into the genome of the animal which develops from that cell. Preferred transgenic animals are primates, mice, rats, cows, pigs, horses, goats, sheep, dogs and cats.

A variety of methods are available for producing transgenic animals. For example, DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., *Proc. Nat. Acad. Sci. USA* 82: 4438–4442, 1985)). By way of another example, embryos can be infected with viruses, especially retroviruses, modified to carry chimeric receptor nucleotide sequences of the present invention.

Pluripotent stem cells derived from the inner cell mass of the embryo and stabilized in culture can be manipulated in culture to incorporate nucleotide sequences of the invention. A transgenic animal can be produced from such stem cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), and Harlan Sprague Dawley (Indianapolis, Ind.).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, *Teratocarcinomas and Embryonic Stem Cells, A Practical Approach*, E. J. Robertson, ed., IRL Press (1987).

Procedures for embryo manipulations are well known in the art. The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout (Experientia 47:897–905, 1991) . Other procedures for introduction of DNA into tissues of animals are described in U.S. Pat. No. 4,945,050 (Sandford et al., Jul. 30, 1990).

Transfection and isolation of desired clones can be carried out using standard techniques (e.g., E. J. Robertson, supra). For example, random gene integration can be carried out by co-transfecting the nucleic acid with a gene encoding antibiotic resistance. Alternatively, for example, the gene encoding antibiotic resistance is physically linked to a nucleic acid sequence encoding a chimeric receptor of the present invention.

DNA molecules introduced into ES cells can also be integrated into the chromosome through the process of homologous recombination. (Capecchi, *Science* 244: 1288–1292, 1989). Methods for positive selection of the recombination event (e.g., neomycin resistance) and dual positive-negative selection (e.g., neomycin resistance and gancyclovir resistance) and the subsequent identification of the desired clones by PCR have been described by Capecchi, supra and Joyner et al., *Nature* 338:153–156, 1989), the teachings of which are incorporated herein.

The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene.

An example describing the preparation of a transgenic mouse is as follows. Female mice are induced to superovulate and placed with males. The mated females are sacrificed by $CO_2$ asphyxiation or cervical dislocation and embryos are recovered from excised oviducts. Surrounding cumulus cells are removed. Pronuclear embryos are then washed and stored until the time of injection.

Randomly cycling adult female mice paired with vasectomized males serve as recipients for implanted embryos. Recipient females are mated at the same time as donor females and embryos are transferred surgically to recipient females.

The procedure for generating transgenic rats is similar to that of mice. See Hammer et al., *Cell* 63:1099–1112, 1990). Procedures for the production of transgenic non-rodent mammals and other animals are known in art. See, for example, Houdebine and Chourrout, supra; Pursel et al., *Science* 244:1281–1288, 1989); and Simms et al., *Bio/Technology* 6:179–183, 1988).

K. Transfected Cell Lines

Nucleic acid expressing a functional chimeric receptor can be used to create transfected cell lines which functionally express a specific chimeric receptor. Such cell lines have a variety of uses such as being used for high-throughput screening for molecules able to modulate metabotropic glutamate receptor activity; and being used to assay binding to a metabotropic glutamate receptor.

A variety of cell lines are capable of coupling exogenously expressed receptors to endogenous functional responses. A number of these cell lines (e.g., NIH-3T3, HeLa, NG115, CHO, HEK 293 and COS7) can be tested to confirm that they lack an endogenous metabotropic glutamate. Those lines lacking a response to external glutamate can be used to establish stably transfected cell lines expressing the cloned chimeric receptors of the invention.

Production of these stable transfectants is accomplished by transfection of an appropriate cell line with a eukaryotic expression vector, such as pMSG, in which the coding sequence for the chimeric metabotropic glutamate receptor cDNA has been cloned into the multiple cloning site. These expression vectors contain a promoter region, such as the mouse mammary tumor virus promoter (MMTV), that drive high-level transcription of cDNAS in a variety of mammalian cells. In addition, these vectors contain genes for the selection of cells that stably express the cDNA of interest. The selectable marker in the PMSG vector encodes an enzyme, xanthine-guanine phosphoribosyl transferase (XGPRT), that confers resistance to a metabolic inhibitor that is added to the culture to kill the nontransfected cells. A variety of expression vectors and selection schemes are usually assessed to determine the optimal conditions for the production of metabotropic glutamate receptor-expressing cell lines for use in high-throughput screening assays.

The most effective method for transfection of eukaryotic cell lines with plasmid DNA varies with the given cell type. The chimeric receptor expression construct will be introduced into cultured cells by the appropriate technique, either $Ca^{2+}$ phosphate precipitation, DEAE-dextran transfection, lipofection or electroporation.

Cells that have stably incorporated or are episomally maintaining the transfected DNA will be identified by their resistance to selection media, as described above, and clonal cell lines will be produced by expansion of resistant colonies. The expression of the chimeric metabotropic glutamate receptor cDNA by these cell lines will be assessed by solution hybridization and Northern blot analysis. Functional expression of the receptor protein will be determined by measuring the mobilization of intracellular $Ca^{2+}$ in response to externally applied calcium receptor agonists.

The following examples illustrate the invention, but do not limit its scope.

III. EXAMPLES

Examples are provided below to illustrate different aspects and embodiments of the present invention. These examples are not intended in any way to limit the disclosed invention. Rather, they illustrate methodologies by which the novel chimeric receptors of the present invention may be constructed. They also illustrate methodologies by which compounds may be screened to determine which compounds bind to or modulate a desired mGluR.

Example 1 phPCaR4.0 and pmGluR1s

Plasmid phPCaR4.0 (Garrett et al., *J. Biol. Chem.*, 270:12919, 1995, hereby incorporated by reference herein) was isolated from *E. coli* bacterial cells containing the plasmid grown up in nutrient broth containing 100 ug/ml ampicillin (Boerhringer Mannheim). This plasmid DNA was used as the source for the DNA encoding the human calcium receptor which was cloned into the EcoRI site of vector pBluescript SK (Stratagene) in the T7 orientation. All restriction enzymes and modification enzymes were purchased from New England Biolabs unless otherwise noted.

Plasmid p7-3/6A was assembled in pBluescript SK from two overlapping subclones of rat mGluR1 obtained from an oligonucleotide screen of a commercially available rat olfactory bulb cDNA library (Stratagene). This plasmid DNA was used as the source of the metabotropic glutamate receptor, mGluR1. It was also used to screen a commercially available human cerebellar cDNA library for the human analogue. The human cerebellar library was screened with a radioactively labeled rat mGluR1 by a method described in Sambrook et al., *Molecular Cloning: A Laboratory Manual*, Chapter 1, 1989. Positive plaques were rescued using the manufacturer's protocol and restriction mapped to compare them against the published human mGluR1 sequence (Eur. Patent publications 0 569 240 A1 and 0 568 384 A1). Two subclones were assembled to create a complete human mGluR1.

Alternatively, the sequence of human mGluR1 may be obtained from European Publication Nos. 0 569 240 A1 and 0 568 384 A1. Probes prepared using this sequence may be used to probe human cDNA libraries to obtain the full length human clone. In addition, the relevant sequences may be synthesized using the sequence described therein.

Example 2 pmGluR1/CaR

Chimeric receptors were constructed using recombinant PCR and a multi-step cloning strategy. An overview of recombinant PCR is presented by R. Higuchi in *PCR Protocols: A Guide to Methods and Applications*, (1990) Academic Press, Inc. In the first construct recombinant PCR was used to combine the sequences of mGluR1 and the CaR across the junction of the extracellular and transmembrane domains. The first chimera, pR1/CaR. contained the extracellular domain of mGluR1 and the transmembrane and intracellular region of the calcium receptor. The chimeric junction was created using three separate PCR reactions. The first reaction used two primers specific for rat mGluR1, A4, a 22 mer encoding nucleotides 1146 to 1167, and an antisense primer, oligoB, a 43 mer containing 22 bases of mGluR1 (nucleotides −1755 to −1776) and 21 bases from the CaR (nucleotides −1837 to −1857). These primers were used to amplify a 650 bp fragment of rat mGluR1. In a separate PCR reaction, a 500 bp fragment of the CaR was amplified using hybrid primer C, a 43 mer which was the complement of oligo B, and D4, an antisense primer corresponding to nucleotides −2256 to −2279 of the CaR. These two PCR products were purified from an agarose gel and annealed together in equal molar ratio in the presence of the external primers A4 and D4 and the proof-reading DNA polymerase, Pfu (Stratagene). The 1,100 bp chimeric PCR product was digested with Nsi I and subcloned into phCar4.0 digested with EcoRV and Nsi I. The resultant subclone was subsequently digested with Xho I and Sfi I to remove the extracellular domain of the CaR which was then replaced with the Xho I–Sfi I fragment of rat mGluR1. The resultant chimera, pR1/Car was validated by restriction mapping and double-stranded DNA sequencing with Sequenase Version 2.0 (US Biochemical). The DNA sequence for pR1/Car (SEQ ID NO: 1) and the corresponding amino acid sequence (SEQ ID NO: 5) is depicted in FIG. 2.

Example 3 pCaR/R1

A second construct, pCaR/R1, was a reciprocal of the chimera described in example 2 in that it encoded the extracellular domain of CaR and the transmembrane and intracellular region of mGluR1. The chimeric junction was created as described above using recombinant PCR. The first reaction used two primers specific for CaR, CRSf1, a 22 mer corresponding to nucleotides 862 to 883, and an antisense primer, CR1794, a 36 mer with 18 bases corresponding to CaR (nucleotides −1777 to −1794) and 18 bases from mGluR1 (nucleotides −2110 to −2127). These primers were used to amplify a 935 bp fragment of CaR. In a separate PCR reaction, a 360 bp fragment of mGluR1 was amplified using hybrid primer R12110, a 36 mer containing 18 bases of CaR (nucleotides 1777 to 1794) covalently attached to 18 bases of mGluR1 ( nucleotides 2110 to 2127) and R1Bgl, an antisense primer corresponding to nucleotides −2451 to −2470 of mGluR1. These two PCR products were purified from an agarose gel and annealed together in equal molar ratio in the presence of the external primers CRSf1 and R1Bgl and the proof-reading DNA polymerase, Pfu (Stratagene). The 1,250 bp chimeric PCR product was digested with Sfi I and Bgl II and subcloned into p7/3A digested with the same enzymes. A subclone was subsequently digested with Sal I and SfiI to remove the extracellular domain of mGluR1 which was then replaced with the Sal I–Sfi I fragment of CaR. The resultant chimera, pCaR/R1 was validated by restriction mapping and double-stranded DNA sequencing using Sequenase Version 2.0 (US Biochemical). The DNA sequence is for pCaR/R1 (SEQ ID NO: 2) and the corresponding amino acid sequence (SEQ ID NO: 6) is depicted in FIG. 3.

Example 4 pratCH3 and phCH4

These chimeras are a result of swapping the CaR cytoplasmic tail onto the extracellular and transmembrane domains of either rat or human mGluR1. Recombinant PCR was used to attach the C-terminal tail of the CaR onto human mGluR1 (which encodes the rat mGluR1 signal sequence) after nucleotide 2535. The first PCR reaction used two primers specific for human mGluR1, M-1rev a 24 mer corresponding to nucleotides 2242 to 2265, and an antisense primer, CH3R1, a 36 mer composed of 18 bases of hmGluR1 (nucleotides −2518 to −2535) and 18 bases of CaR (nucleotides −2602 to −2619). These primers were used to amplify a 300 bp fragment of hmGluR1. In a separate PCR reaction, a 750 bp fragment of the CaR was amplified using hybrid primer CH3CaR, a 36 mer which is the complement of oligo CH3R1, and a commercially available T3 primer (Stratagene) which primes in the Bluescript vector in a region downstream from the 3' end of the CaR. The two PCR products were purified from an agarose gel and annealed together in equal molar ratio in the presence of the external primers M-1 rev and T3 and the proof-reading DNA polymerase, Pfu (Stratagene). The 1 kb chimeric PCR product was digested with Nhe I and Not I and subcloned into phmGluR1 digested with the same enzymes. The resultant chimera, phCH4 was validated by restriction mapping and double-stranded DNA sequencing. To detect functional activity in the oocyte assay with this clone it was necessary to exchange the 5' untranslated region and the signal sequence from rat mGluR1 with the same region of this human clone. This was done utilizing a Bsu36I restriction site. Additionally, an Acc I fragment of rat mGluR1 was subcloned into phCH4 to create a rat version of this same chimera. This chimera is referred to as ratCH3. The DNA sequence for pratCh3 (SEQ ID NO:3) and the corresponding amino acid sequence (SEQ ID NO:7) are depicted in FIG. 4. The DNA sequence for phCH44 (SEQ ID NO: 4) and the corresponding amino acid sequence (SEQ ID NO:8) are depicted in FIG. 5.

Using the techniques described in the above-mentioned examples, we therefore envision the construction, evaluation and screening utility of other mGluR/CaR chimeras. In this example we have taken a Group I metabotropic glutamate receptor which, similar to the calcium receptor, is coupled to the activation of phospholipase C and mobilization of intracellular calcium, and by swapping the C-terminal tail, maintained the integrity of the second messenger system. Additionally, when the CaR tail was added to mGluR1, the desensitization properties were lost. This demonstrates the feasibility of changing specific G-protein coupling of metabotropic glutamate receptors to those of the CaR by swapping intracellular domains. By example, Group II mGluRs, such as mGluR2 or mGluR3 which are $G_i$ coupled, could be changed to Gq coupled receptors. This can be done by exchanging onto these receptors the C-terminal cytosolic tail of the CaR using the protocol described in examples 2, 3 and 4. Effective Gq coupling could be evaluated in the oocyte as described in examples 5 and 6. Activation of a Group II by L-CCG-I (their most potent agonist), should induce mobilization of intracellular Ca2+ which will cause the detectable inward rectifying Cl− current measured in the voltage-clamped oocyte.

To increase the effectiveness of G-protein binding it may be useful to swap one or more additional intracellular (cytoplasmic) loops of the CaR onto the mGluR1. By example, such substitution can involve any of: intracellular loop 1, intracellular loop 2 and intracellular loop 3 from a calcium receptor, substituted alone or in any combination of loops. Such subdomain swapping may be necessary for the most effective transference of G-protein binding specificity.

Example 5

In vitro transcription of RNA

RNA transcripts encoding the receptors described in examples 1 through 4 were produced by enzymatic transcription from plasmid templates using T7 polymerase supplied with the mMessage mMachine ™(Ambion). Each plasmid was treated with a restriction enzyme to make a single cut distal to the 3' end of the cDNA insert to linearize the template. This DNA was incubated with T7 RNA polymerase in the presence of GpppG cap nucleotide, rATP, rCTP, rUTP and rGTP. The synthetic RNA transcript is purified by DNase treatment of the reaction mix and subsequent alcohol precipitations. RNA was quantitated by absorbance spectroscopy ($OD_{260}$) and visualized on an ethidium stained 1.2% formaldehyde gel.

Example 6

Functional Expression in Oocytes

Oocytes suitable for injection were obtained from adult female *Xenopus laevis* toads using procedures described in C. J. Marcus-Sekura and M. J. M. Hitchcock, *Methods in Enzymology*, Vol. 152 (1987). Pieces of ovarian lobe were incubated for 30 minutes in $Ca^{2+}$-free Modified Barths Saline (MBS) containing 1.5 mg/ml collagenase type IA (Worthington). Subsequently, 5 ng of RNA transcript prepared as described in Example 5, were injected into each oocyte. Following injection, oocytes were incubated at 16° C. in MBS containing 0.5 mM $CaCl_2$ for 2–7 days prior to electrophysiological examination.

The ability of each chimeric receptor to function was determined by voltage-recording of current-passing electrodes across the oocyte membrane in response to glutamate and calcium receptor agonists. Oocytes were voltage clamped at a holding potential of −60 mV with an Axoclamp 2A amplifier (Axon Instruments, Foster City, Calif.) using standard two electrode voltage-clamp techniques. Currents were recorded on a chart recorder. The standard control saline was MBS containing 0.3 mM $CaCl_2$ and 0.8 $MgCl_2$. Test substances were applied by superfusion at a flow rate of about 5 ml/min. All experiments were done at room temperature. The holding current was stable in a given oocyte and varied between +10 to −200 nA for different oocytes. Activation of $I_{cl}$ in response to activation of receptors and subsequent increases in intracellular Ca2+ ($[Ca]_{in}$) was quantified by measuring the peak inward current stimulated by agonist or drug, relative to the holding current at −60 mV.

Figure 6:
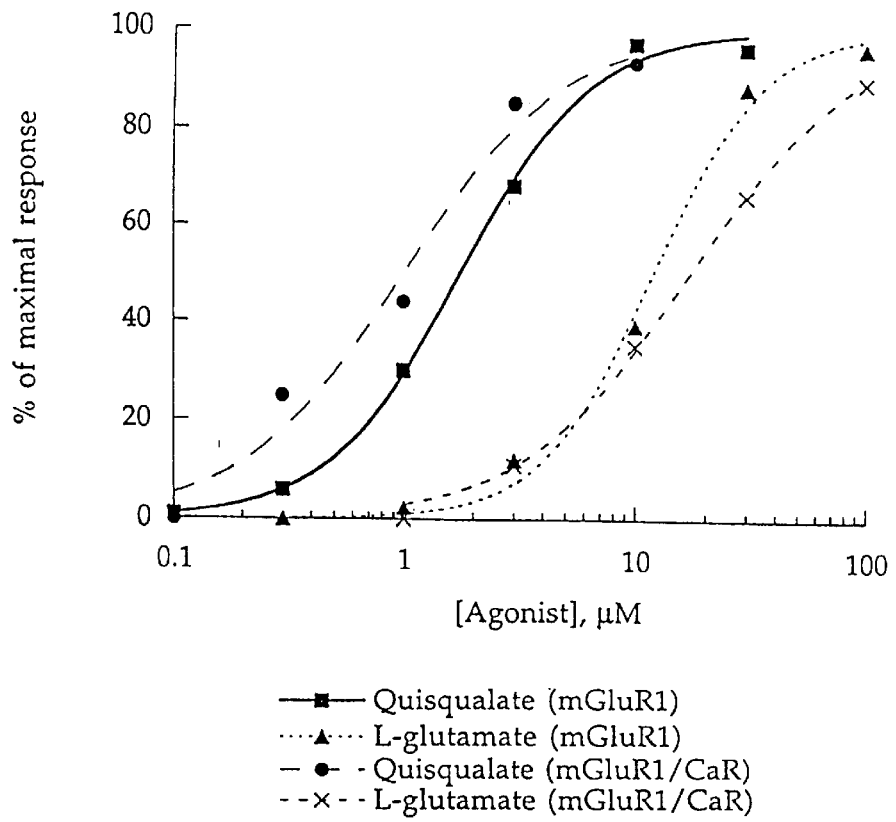
FIG. 6 is a graphical representation showing the activation of mGluR1/CaR by the mGluR1 agonists quisqualate and 1-glutamate as measured by Cl− currents generated in response to the release of intracellular Ca2+ in the oocyte.

FIG. 6 pR1/CaR vs. rat mGluR1 (glutamate and quisqualate).

Figure 7:
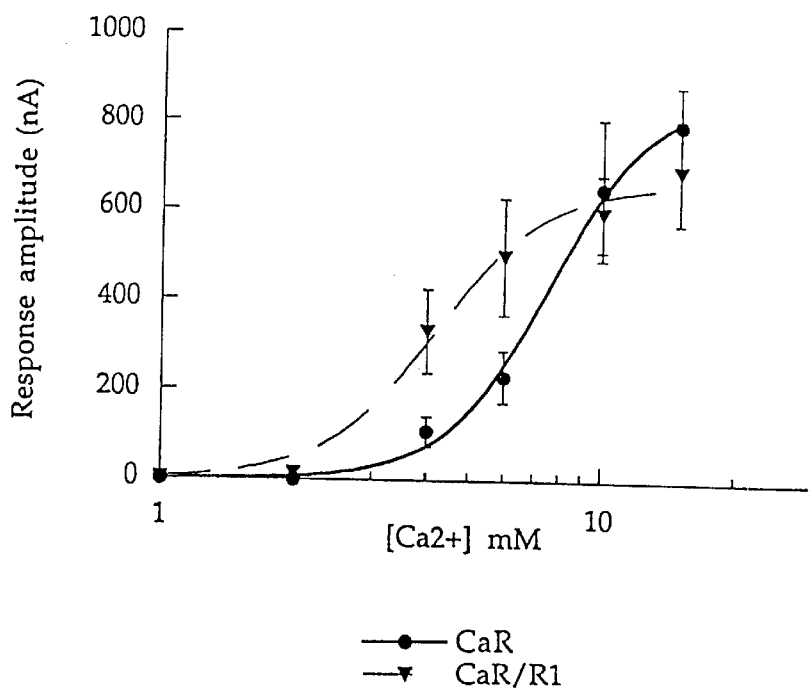
FIG. 7 is a graphical representation of activation of CaR and CaR/R1 chimera by increasing extracellular calcium. Response amplitudes (Cl− currents in response to increases in intracellular Ca2+) are shown. The data shows that CaR/R1 is activated by extracellular Ca2+ in a manner similar to CaR.

FIG. 7 CaR/R1 vs. hPCar (calcium)

FIG. 8 pratCH3 vs. rat mGluR1 and CaR (desensitization traces)

Example 7

Construction of pCEPCaR/R1 from pCaR/R1

The DNA from plasmid pCaR/R1 was digested and cloned into the commercially available episomal mammalian expression vector, pCEP4 (Invitrogen), using the restriction enzymes Kpn I and Not I. The ligation products were transfected into DH5a cells which had been made competent for DNA transformation. These cells were plated on Luria-Bertani Media (LB) plates (described in Sambrook et al., *Molecular Cloning: A Laboratory Manual*, 1989)) containing 100 ug/ml ampicillin. A clone was selected from the colonies which grew. This clone, pCEPCaR/R1 was characterized by restriction enzyme digestion.

Example 8

Transfection and Growth of HEK293/pCEPCaR/R1

Human embryonic kidney cells (293, ATCC, CRL 1573) were grown in a routine manner. Cells were plated in 10 cm cell-culture plates in Dulbecco's modified Eagle's medium (D-MEM) containing 10% fetal calf serum (FCS) and 1×Penicillin-Streptomycin (PS, Life Technologies) so that they would be ~70% confluent after an overnight incubation. To prepare DNA for transfection, the plasmid pCEPCaR/R1 was precipitated with ethanol, rinsed and resuspended in sterile water at a concentration of 1 ug/ul. Fourteen micrograms of DNA was incubated with the liposome formulation LipofectAMINE™ (Life Technologies) for 20 minutes in serum-free Opti-MEM® (Life Technologies). After the room temperature incubation, 6.8 mls of Opti-MEM® was added to the transfection mix. This solution was added to the cells which had been rinsed with 2×5 ml washes of serum-free Opti-MEM®. The cells and transfection mix were incubated at 37° C. for 5 hours at which time more media and fetal bovine serum were added to bring the serum concentration to 10%. After an overnight incubation the media was changed back to D-MEM with 10% FCS and 1×PS. After an additional 24 h incubation, cells were detached with trypsin and replated in media containing 200 ug/ml hygromycin (Boerhringer Mannheim). Those cells which grew contained pCEPCaR/R1 which encodes the hygromycin resistance gene. Individual clones were recovered and propagated using standard tissue-culture techniques. Subcultures of both individual clones and pooled stables were prepared by dissociation into fresh tissue culture media, and plated into fresh culture dishes at 1/10th the original volume.

Example 9

HEK293/pCEPCaR/R1 Fura Assay

Measurements of intracellular calcium release in response to increases in extracellular calcium is quantitated using the Fura assay (Parks et al. 1989). Stably transfected cells containing pCEPCaR/R1 are loaded with 2 $\mu$M fura-2 acetoxymethylester by incubation for 20–30 minutes at 37° C. in SPF-PCB (126 mM NaCl, 5 mM KCl, 1 mM $MgCl_2$, 20 mM HEPES, pH 7.4), containing 1.25 mM $CaCl_2$, 1 mg/ml glucose, 0.5% BSA[1]. The cells are then washed 1 to 2 times in SPF-PCB containing 0.5 mM $CaCl_2$, 0.5% BSA and resuspended to a density of 4 to 5 million cells/ml and kept at 22° C. in a plastic beaker. For recording fluorescent signals, the cells are diluted fivefold into a quartz cuvette with BSA-free 37° C. SPF-PCB to achieve a final BSA concentration of 0.1% (1.2 ml of 37° C. BSA-free SPF-PCB+0.3 ml cell suspension). Measurements of fluorescence are performed at 37° C. with constant stirring using a custom-built spectrofluorimeter (Biomedical Instrumentation Group, University of Pennsylvania). Excitation and emission wavelengths are 340 and 510 nm, respectively. To calibrate fluorescence signals, digitonin (Sigma, St. Louis, Mo.; catalog # D 5628; 50 $\mu$g/ml, final) is added to obtain $F_{max}$, and the apparent $F_{min}$ is determined by adding EGTA (10 mM, final) and Tris base (pH ~10, final). Concentrations of released intracellular $Ca^{2+}$ is calculated using a dissociation constant (Kd) of 224 nM and the equation:

$$[Ca^{2+}]_i=(F-F_{min}/F_{max}-F)\times kd$$

Figure 9:
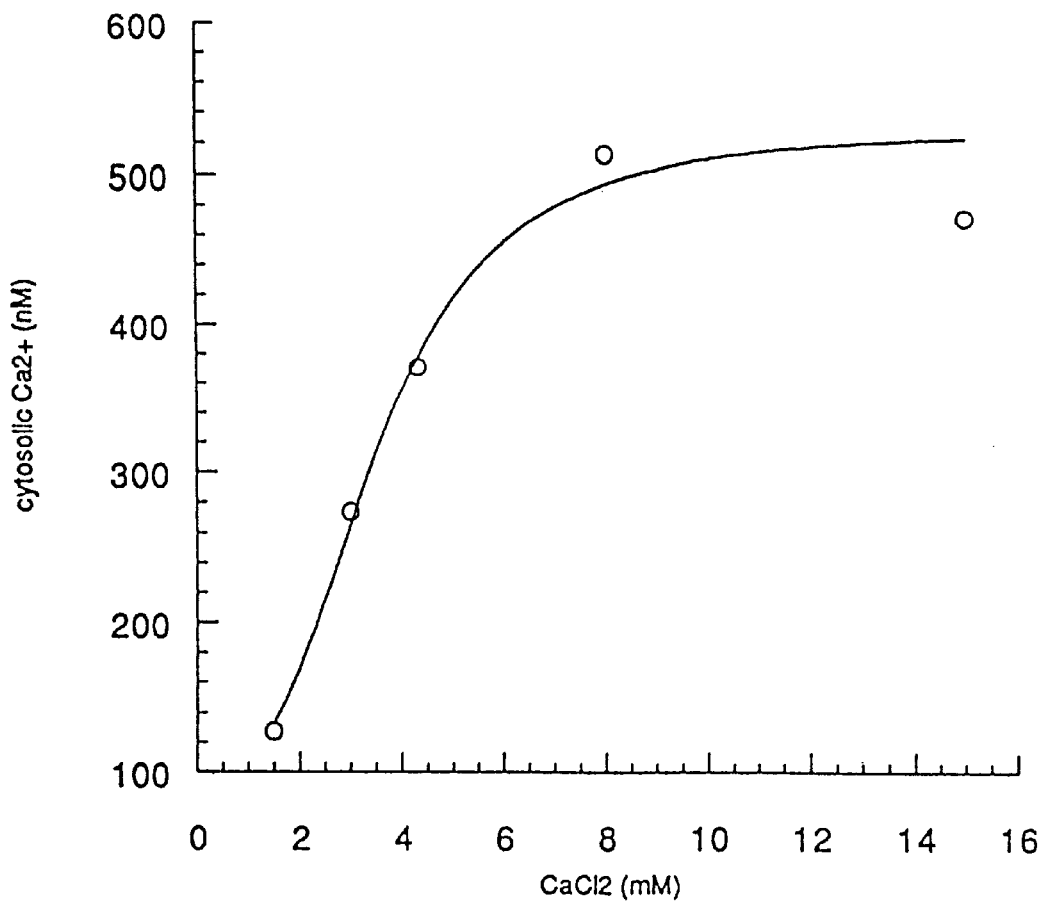
FIG. 9 is a graphical representation showing increases in intracellular calcium induced by extracellular calcium in fura-2 loaded stably transfected HEK293 cells expressing pCEPCaR/R1.

The results are graphically represented in FIG. 9.

Example 10

Recombinant Receptor Binding Assay

The following is one example of a rapid screening assay to obtain compounds modulating metabotropic glutamate receptor activity. The screening assay first measures the ability of compounds to bind to recombinant chimeric receptors, or receptor fragments or mGluR, CaR or chimeric receptors. Compounds binding to such receptors or fragments are then tested for their ability to modulate one or more activities at a metabotropic glutamate receptor.

In one procedure, a cDNA or gene clone encoding a metabotropic glutamate receptor is obtained. Distinct fragments of the clone are expressed in an appropriate expression vector to produce the smallest receptor polypeptide(s) obtainable able to bind glutamate. Such experiments can be facilitated by utilizing a stably transfected mammalian cell line (e.g., HEK 293 cells) expressing the metabotropic glutamate receptor.

The recombinant polypeptide(s) having the desired binding properties can be bound to a solid-phase support using standard chemical procedures. This solid-phase, or affinity matrix, may then be contacted with glutamate to demonstrate that glutamate can bind to the column, and to identify conditions by which glutamate may be removed from the solid-phase. This procedure may then be repeated using a large library of compounds to determine those compounds which are able to bind to the affinity matrix. Bound compounds can then can be released in a manner similar to glutamate. Alternative binding and release conditions may be utilized to obtain compounds capable of binding under conditions distinct from those used for glutamate binding (e.g., conditions which better mimic physiological conditions encountered especially in pathological states). Compounds binding to the mGluR can thus be selected from a very large collection of compounds present in a liquid medium or extract.

In an alternate method, chimeric metabotropic glutamate/calcium receptors are bound to a column or other solid phase support. Those compounds which are not competed off by reagents binding to the glutamate binding site on the receptor can then be identified. Such compounds define alternative binding sites on the receptor. Such compounds may be structurally distinct from known compounds and may define chemical classes of agonists or antagonists which may be useful as therapeutics agents.

Other embodiments are within the following claims.

What we claim is:

1. A mGluR/CaR chimeric receptor comprising the amino acid sequence of a metabotropic glutamate receptor substituted with one or more regions of at least 6 contiguous amino acids of a G-protein coupled calcium receptor, provided that said mGluR/CaR chimeric receptor comprises one or more regions of at least 6 contiguous amino acids of said metabotropic glutamate receptor.

2. The mGluR/CaR chimeric receptor of claim 1, wherein said mGluR/CaR chimeric receptor comprises an extracellular domain of said metabotropic glutamate receptor, a seven transmembrane domain of said metabotropic glutamate receptor, and an intracellular cytoplasmic tail domain of said calcium receptor.

3. The mGluR/CaR chimeric receptor of claim 1, wherein said mGluR/CaR chimeric receptor comprises an extracellular domain of said metabotropic glutamate receptor, a seven transmembrane domain of said calcium receptor, and an intracellular cytoplasmic tail domain of said metabotropic glutamate receptor.

4. The mGluR/CaR chimeric receptor of claim 1, wherein said mGluR/CaR chimeric receptor comprises an extracellular domain of said metabotropic glutamate receptor, a seven transmembrane domain of said calcium receptor, and an intracellular cytoplasmic tail domain of said calcium receptor.

5. The mGluR/CaR chimeric receptor of claim 1, wherein said mGluR/CaR chimeric receptor comprises an extracellular domain of said calcium receptor, a seven transmembrane domain of said metabotropic glutamate receptor, and an intracellular cytoplasmic tail domain of said metabotropic glutamate receptor.

6. The mGluR/CaR chimeric receptor of claim 1, wherein said mGluR/CaR chimeric receptor comprises an extracellular domain of said calcium receptor, a seven transmembrane domain of said metabotropic glutamate receptor, and an intracellular cytoplasmic tail domain of said calcium receptor.

7. The mGluR/CaR chimeric receptor of claim 1, wherein said mGluR/CaR chimeric receptor comprises an extracellular domain of said calcium receptor, a seven transmembrane domain of said calcium receptor, and an intracellular cytoplasmic tail domain of said metabotropic glutamate receptor.

8. The mGluR/CaR chimeric receptor of claim 1, wherein said calcium receptor is a human calcium receptor.

9. The mGluR/CaR chimeric receptor of claim 8, wherein said metabotropic glutamate receptor is a human metabotropic glutamate receptor.

10. The mGluR/CaR chimeric receptor of claim 9, wherein said mGluR/CaR chimeric receptor comprises an extracellular domain of said metabotropic glutamate receptor, a seven transmembrane domain of said metabotropic glutamate receptor, and an intracellular cytoplasmic tail domain of said calcium receptor.

11. The mGluR/CaR chimeric receptor of claim 9, wherein said mGluR/CaR chimeric receptor comprises an extracellular domain of said metabotropic glutamate receptor, a seven transmembrane domain of said calcium receptor, and an intracellular cytoplasmic tail domain of said metabotropic glutamate receptor.

12. The mGluR/CaR chimeric receptor of claim 9, wherein said mGluR/CaR chimeric receptor comprises an extracellular domain of said metabotropic glutamate receptor, a seven transmembrane domain of said calcium receptor, and an intracellular cytoplasmic tail domain of said calcium receptor.

13. The mGluR/CaR chimeric receptor of claim 9, wherein said mGluR/CaR chimeric receptor comprises an extracellular domain of said calcium receptor, a seven transmembrane domain of said metabotropic glutamate receptor, and an intracellular cytoplasmic tail domain of said metabotropic glutamate receptor.

14. The mGluR/CaR chimeric receptor of claim 9, wherein said mGluR/CaR chimeric receptor comprises an extracellular domain of said calcium receptor, a seven transmembrane domain of said metabotropic glutamate receptor, and an intracellular cytoplasmic tail domain of said calcium receptor.

15. The mGluR/CaR chimeric receptor of claim 9, wherein said mGluR/CaR chimeric receptor comprises an extracellular domain of said calcium receptor, a seven transmembrane domain of said calcium receptor, and an intracellular cytoplasmic tail domain of said metabotropic glutamate receptor.

16. The mGluR/CaR chimeric receptor of claim 1, wherein said mGluR/CaR chimeric receptor comprises the amino acid sequence of SEQ ID NO 5.

17. The mGluR/CaR chimeric receptor of claim 1, wherein said mGluR/CaR chimeric receptor comprises the amino acid sequence of SEQ ID NO 6.

18. The mGluR/CaR chimeric receptor of claim 1, wherein said mGluR/CaR chimeric receptor comprises the amino acid sequence of SEQ ID NO 7.

19. The mGluR/CaR chimeric receptor of claim 1, wherein said mGluR/CaR chimeric receptor comprises the amino acid sequence of SEQ ID NO 8.

20. The mGluR/CaR chimeric receptor of any one of claims 19, consisting of said metabotropic glutamate receptor substituted with one or more regions of at least 6 contiguous amino acids of said G-protein coupled calcium receptor.

21. A recombinant nucleic acid comprising a nucleotide sequence encoding the mGluR/CaR chimeric receptor of claim 20.

22. A replicable, expression vector comprising a nucleotide sequence encoding the mGluR/CaR chimeric receptor of claim 20.

23. A cell comprising the replicable expression vector of claim 22.

24. A process for producing a receptor comprising the step of growing, under suitable nutrient conditions, procaryotic or eucaryotic host cells transformed or transfected with the expression vector of claim 23, in a manner allowing expression of said mGluR/CaR chimeric receptor.

25. A method for measuring the ability of a compound to effect the activity of a chimeric receptor made up of one or more metabotropic glutamate receptor regions and one or more calcium receptor regions comprising the steps:
  a) contacting a cell expressing a mGluR/CaR chimeric receptor comprising the amino acid sequence of a metabotropic glutamate receptor substituted with one or more regions of at least 6 contiguous amino acids of a. G-protein coupled calcium receptor, provided that said mGluR/CaR chimeric receptor comprises one or more regions of at least 6 contiguous amino acids of said metabotropic glutamate receptor; and
  b) measuring the ability of said compound to modulate an activity of said mGluR/CaR chimeric receptor.

26. The method of claim 25, wherein said mGluR/CaR chimeric receptor comprises an extracellular domain of said metabotropic glutamate receptor, a seven transmembrane domain of said metabotropic glutamate receptor, and an intracellular cytoplasmic tail domain of said calcium receptor.

27. The method of claim 25, wherein said mGluR/CaR chimeric receptor comprises an extracellular domain of said metabotropic glutamate receptor, a seven transmembrane domain of said calcium receptor, and an intracellular cytoplasmic tail domain of said metabotropic glutamate receptor.

28. The method of claim 25, wherein said mGluR/CaR chimeric receptor comprises an extracellular domain of said metabotropic glutamate receptor, a seven transmembrane domain of said calcium receptor, and an intracellular cytoplasmic tail domain of said calcium receptor.

29. The method of claim 25, wherein said mGluR/CaR chimeric receptor comprises an extracellular domain of said calcium receptor, a seven transmembrane domain of said metabotropic glutamate receptor, and an intracellular cytoplasmic tail domain of said metabotropic glutamate receptor.

30. The method of claim 25, wherein said mGluR/CaR chimeric receptor comprises an extracellular domain of said calcium receptor, a seven transmembrane domain of said metabotropic glutamate receptor, and an intracellular cytoplasmic tail domain of said calcium receptor.

31. The method of claim 25, wherein said mGluR/CaR chimeric receptor comprises an extracellular domain of said calcium receptor, a seven transmembrane domain of said calcium receptor, and an intracellular cytoplasmic tail domain of said metabotropic glutamate receptor.

32. The method of claim 25, wherein said calcium receptor is a human calcium receptor.

33. The method of claim 32, wherein said metabotropic glutamate receptor is a human metabotropic glutamate receptor.

34. The method of claim 33, wherein said mGluR/CaR chimeric receptor comprises an extracellular domain of said metabotropic glutamate receptor, a seven transmembrane domain of said metabotropic glutamate receptor, and an intracellular cytoplasmic tail domain of said calcium receptor.

35. The method of claim 33, wherein said mGluR/CaR chimeric receptor comprises an extracellular domain of said metabotropic glutamate receptor, a seven transmembrane domain of said calcium receptor, and an intracellular cytoplasmic tail domain of said metabotropic glutamate receptor.

36. The method of claim 33, wherein said mGluR/CaR chimeric receptor comprises an extracellular domain of said metabotropic glutamate receptor, a seven transmembrane domain of said calcium receptor, and an intracellular cytoplasmic tail domain of said calcium receptor.

37. The method of claim 33, wherein said mGluR/CaR chimeric receptor comprises an extracellular domain of said calcium receptor, a seven transmembrane domain of said metabotropic glutamate receptor, and an intracellular cytoplasmic tail domain of said metabotropic glutamate receptor.

38. The method of claim 33, wherein said mGluR/CaR chimeric receptor comprises an extracellular domain of said calcium receptor, a seven transmembrane domain of said metabotropic glutamate receptor, and an intracellular cytoplasmic tail domain of said calcium receptor.

39. The method of claim 33, wherein said mGluR/CaR chimeric receptor comprises an extracellular domain of said calcium receptor, a seven transmembrane domain of said calcium receptor, and an intracellular cytoplasmic tail domain of said metabotropic glutamate receptor.

40. The method of claim 25, wherein said mGluR/CaR chimeric receptor comprises the amino acid sequence of SEQ ID NO 5.

41. The method of claim 25, wherein said mGluR/CaR chimeric receptor comprises the amino acid sequence of SEQ ID NO 6.

42. The method of claim 25, wherein said mGluR/CaR chimeric receptor comprises the amino acid sequence of SEQ ID NO 7.

43. The method of claim 25, wherein said chimeric mGluR/CaR receptor comprises the amino acid sequence of SEQ ID NO 8.

44. The method of claim 25, wherein said compound modulates the activity of a metabotropic glutamate receptor and said method repeats said step (a) and step (b) one or more times using a different one of said mGluR/CaR chimeric receptor to identify a metabotropic glutamate receptor ligand binding region.

45. The method of claim 25, wherein said compound modulates the activity of a calcium receptor and said method repeats said step (a) and said step (b) one or more times using a different one of said mGluR/CaR chimeric receptor to identify a calcium receptor ligand binding region.

46. The method of any one of claims 25–43 wherein said chimeric mGluR/CaR receptor consists of said metabotropic glutamate receptor substituted with one or more regions of at least 6 contiguous amino acids of said G-protein coupled calcium receptor.

47. The method of any one of claims 25–43 wherein said compound modulates a metabotropic glutamate receptor activity.

48. The method of any one of claims 25–43 wherein said compound modulates a calcium receptor activity.

* * * * *

UNITED STATES PATENT AND TRADEMARK OFFICE
CERTIFICATE OF CORRECTION

PATENT NO. : 5,981,195
DATED : November 9, 1999
INVENTOR(S) : Fuller et al.

It is certified that error appears in the above-identified patent and that said Letters Patent is hereby corrected as shown below:

<u>Column 88,</u>
Line 19, change "claim 19" to -- claims 1-19 --.

Signed and Sealed this

Thirtieth Day of July, 2002

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES:    8

(2) INFORMATION FOR SEQ ID NO: 1:

(i) SEQUENCE CHARACTERISTICS:
        (A) LENGTH:        3384 base pairs
        (B) TYPE:          nucleic acid
        (C) STRANDEDNESS:   single
        (D) TOPOLOGY:      linear (xi) SEQUENCE DESCRIPTION: SEQ ID NO: 1:

```
CGCCACAATG GTCCGGCTCC TCTTGATTTT CTTCCCAATG ATCTTTTTGG AGATGTCCAT      60

TTTGCCCAGG ATGCCTGACA GAAAAGTATT GCTGGCAGGT GCCTCGTCCC AGCGCTCCGT     120

GGCGAGAATG GACGGAGATG TCATCATCGG AGCCCTCTTC TCAGTCCATC ACCAGCCTCC     180

AGCCGAGAAG GTACCCGAAA GGAAGTGTGG GGAGATCAGG GAACAGTATG GTATCCAGAG     240

GGTGGAGGCC ATGTTCCACA CGTTGGATAA GATTAACGCG GACCCGGTGC TCCTGCCCAA     300

CATCACTCTG GGCAGTGAGA TCCGGGACTC CTGCTGGCAC TCTTCAGTGG CTCTCGAACA     360

GAGCATCGAA TTCATCAGAG ACTCCCTGAT TTCCATCCGA GATGAGAAGG ATGGGCTGAA     420

CCGATGCCTG CCTGATGGCC AGACCCTGCC CCCTGGCAGG ACTAAGAAGC CTATTGCTGG     480

AGTGATCGGC CCTGGCTCCA GCTCTGTGGC CATTCAAGTC CAGAATCTTC TCCAGCTGTT     540

CGACATCCCA CAGATCGCCT ATTCTGCCAC AAGCATAGAC CTGAGTGACA AAACTTTGTA     600

CAAATACTTC CTGAGGGTGG TCCCTTCTGA CACTTTGCAG GCAAGGGCGA TGCTCGACAT     660

AGTCAAGCGT TACAACTGGA CCTATGTCTC AGCAGTCCAC ACAGAAGGGA ATTACGGCGA     720

GAGTGGAATG GATGCTTTCA AAGAACTGGC TGCCCAGGAA GGCCTCTGCA TCGCACACTC     780
```

-continued

| | |
|---|---|
| GGACAAAATC TACAGCAATG CTGGCGAGAA GAGCTTTGAC CGGCTCCTGC GTAAACTCCG | 840 |
| GGAGCGGCTT CCCAAGGCCA GGGTTGTGGT CTGCTTCTGC GAGGGCATGA CAGTGCGGGG | 900 |
| CTTACTGAGT GCCATGCGCC GCCTGGGCGT CGTGGGCGAG TTCTCACTCA TTGGAAGTGA | 960 |
| TGGATGGGCA GACAGAGATG AAGTCATCGA AGGCTATGAG GTGGAAGCCA ACGGAGGGAT | 1020 |
| CACAATAAAG CTTCAGTCTC CAGAGGTCAG GTCATTTGAT GACTACTTCC TGAAGCTGAG | 1080 |
| GCTGGACACC AACACAAGGA ATCCTTGGTT CCCTGAGTTC TGGCAACATC GCTTCCAGTG | 1140 |
| TCGCCTACCT GGACACCTCT TGGAAAACCC CAACTTTAAG AAAGTGTGCA CAGGAAATGA | 1200 |
| AAGCTTGGAA GAAAACTATG TCCAGGACAG CAAAATGGGA TTTGTCATCA ATGCCATCTA | 1260 |
| TGCCATGGCA CATGGGCTGC AGAACATGCA CCATGCTCTG TGTCCCGGCC ATGTGGGCCT | 1320 |
| GTGTGATGCT ATGAAACCCA TTGATGGCAG GAAGCTCCTG GATTTCCTCA TCAAATCCTC | 1380 |
| TTTTGTCGGA GTGTCTGGAG AGGAGGTGTG GTTCGATGAG AAGGGGGATG CTCCCGGAAG | 1440 |
| GTATGACATT ATGAATCTGC AGTACACAGA AGCTAATCGC TATGACTATG TCCACGTGGG | 1500 |
| GACCTGGCAT GAAGGAGTGC TGAATATTGA TGATTACAAA ATCCAGATGA ACAAAAGCGG | 1560 |
| AATGGTACGA TCTGTGTGCA GTGAGCCTTG CTTAAAGGGT CAGATTAAGG TCATACGGAA | 1620 |
| AGGAGAAGTG AGCTGCTGCT GGATCTGCAC GGCCTGCAAA GAGAATGAGT TTGTGCAGGA | 1680 |
| CGAGTTCACC TGCAGAGCCT GTGACCTGGG GTGGTGGCCC AACGCAGAGC TCACAGGCTG | 1740 |
| TGAGCCCATT CCTGTCCGTT ATCTTGAGTG GAGTGACATA GAAGGGATCG CACTCACCCT | 1800 |
| CTTTGCCGTG CTGGGCATTT TCCTGACAGC CTTTGTGCTG GGTGTGTTTA TCAAGTTCCG | 1860 |
| CAACACACCC ATTGTCAAGG CCACCAACCG AGAGCTCTCC TACCTCCTCC TCTTCTCCCT | 1920 |
| GCTCTGCTGC TTCTCCAGCT CCCTGTTCTT CATCGGGGAG CCCCAGGACT GGACGTGCCG | 1980 |
| CCTGCGCCAG CCGGCCTTTG GCATCAGCTT CGTGCTCTGC ATCTCATGCA TCCTGGTGAA | 2040 |
| AACCAACCGT GTCCTCCTGG TGTTTGAGGC CAAGATCCCC ACCAGCTTCC ACCGCAAGTG | 2100 |
| GTGGGGGCTC AACCTGCAGT TCCTGCTGGT TTTCCTCTGC ACCTTCATGC AGATTGTCAT | 2160 |
| CTGTGTGATC TGGCTCTACA CCGCGCCCCC CTCAAGCTAC CGCAACCAGG AGCTGGAGGA | 2220 |
| TGAGATCATC TTCATCACGT GCCACGAGGG CTCCCTCATG GCCCTGGGCT TCCTGATCGG | 2280 |
| CTACACCTGC CTGCTGGCTG CCATCTGCTT CTTCTTTGCC TTCAAGTCCC GGAAGCTGCC | 2340 |
| GGAGAACTTC AATGAAGCCA AGTTCATCAC CTTCAGCATG CTCATCTTCT TCATCGTCTG | 2400 |
| GATCTCCTTC ATTCCAGCCT ATGCCAGCAC CTATGGCAAG TTTGTCTCTG CCGTAGAGGT | 2460 |
| GATTGCCATC CTGGCAGCCA GCTTTGGCTT GCTGGCGTGC ATCTTCTTCA ACAAGATCTA | 2520 |
| CATCATTCTC TTCAAGCCAT CCCGCAACAC CATCGAGGAG GTGCGTTGCA GCACCGCAGC | 2580 |
| TCACGCTTTC AAGGTGGCTG CCCGGGCCAC GCTGCGCCGC AGCAACGTCT CCCGCAAGCG | 2640 |
| GTCCAGCAGC CTTGGAGGCT CCACGGGATC CACCCCCTCC TCCTCCATCA GCAGCAAGAG | 2700 |
| CAACAGCGAA GACCCATTCC CACAGCCCGA GAGGCAGAAG CAGCAGCAGC CGCTGGCCCT | 2760 |
| AACCCAGCAA GAGCAGCAGC AGCAGCCCCT GACCCTCCCA CAGCAGCAAC GATCTCAGCA | 2820 |
| GCAGCCCAGA TGCAAGCAGA AGGTCATCTT TGGCAGCGGC ACGGTCACCT TCTCACTGAG | 2880 |
| CTTTGATGAG CCTCAGAAGA ACGCCATGGC CCACGGGAAT TCTACGCACC AGAACTCCCT | 2940 |
| GGAGGCCCAG AAAAGCAGCG ATACGCTGAC CCGACACCAG CCATTACTCC CGCTGCAGTG | 3000 |
| CGGGGAAACG GACTTAGATC TGACCGTCCA GGAAACAGGT CTGCAAGGAC CTGTGGGTGG | 3060 |
| AGACCAGCGG CCAGAGGTGG AGGACCCTGA AGAGTTGTCC CCAGCACTTG TAGTGTCCAG | 3120 |
| TTCACAGAGC TTTGTCATCA GTGGTGGAGG CAGCACTGTT ACAGAAAACG TAGTGAATTC | 3180 |

```
ATAAAATGGA AGGAGAAGAC TGGGCTAGGG AGAATGCAGA GAGGTTTCTT GGGGTCCCAG        3240

GGATGAGGAA TCGCCCCAGA CTCCTTTCCT CTGAGGAAGA AGGGATAATA GACACATCAA        3300

ATGCCCCGAA TTTAGTCACA CCATCTTAAA TGACAGTGAA TTGACCCATG TTCCCTTTAA        3360

AAAAAAAAAA AAAAAAGCGG CCGC                                              3384

(2) INFORMATION FOR SEQ ID NO: 2:

(i) SEQUENCE CHARACTERISTICS:
        (A) LENGTH:           4000 base pairs
        (B) TYPE:             nucleic acid
        (C) STRANDEDNESS:     single
        (D) TOPOLOGY:         linear (xi) SEQUENCE DESCRIPTION: SEQ ID NO: 2:

CTAGCTGTCT CATCCCTTGC CCTGGAGAGA CGGCAGAACC ATGGCATTTT ATAGCTGCTG          60

CTGGGTCCTC TTGGCACTCA CCTGGCACAC CTCTGCCTAC GGGCCAGACC AGCGAGCCCA         120

AAAGAAGGGG GACATTATCC TTGGGGGGCT CTTTCCTATT CATTTTGGAG TAGCAGCTAA         180

AGATCAAGAT CTCAAATCAA GGCCGGAGTC TGTGGAATGT ATCAGGTATA ATTTCCGTGG         240

GTTTCGCTGG TTACAGGCTA TGATATTTGC CATAGAGGAG ATAAACAGCA GCCCAGCCCT         300

TCTTCCCAAC TTGACGCTGG GATACAGGAT ATTTGACACT TGCAACACCG TTTCTAAGGC         360

CTTGGAAGCC ACCCTGAGTT TTGTTGCTCA AAACAAAATT GATTCTTTGA ACCTTGATGA         420

GTTCTGCAAC TGCTCAGAGC ACATTCCCTC TACGATTGCT GTGGTGGGAG CAACTGGCTC         480

AGGCGTCTCC ACGGCAGTGG CAAATCTGCT GGGGCTCTTC TACATTCCCC AGGTCAGTTA         540

TGCCTCCTCC AGCAGACTCC TCAGCAACAA GAATCAATTC AAGTCTTTCC TCCGAACCAT         600

CCCCAATGAT GAGCACCAGG CCACTGCCAT GGCAGACATC ATCGAGTATT CCGCTGGAA          660

CTGGGTGGGC ACAATTGCAG CTGATGACGA CTATGGGCGG CCGGGGATTG AGAAATTCCG         720

AGAGGAAGCT GAGGAAAGGG ATATCTGCAT CGACTTCAGT GAACTCATCT CCCAGTACTC         780

TGATGAGGAA GAGATCCAGC ATGTGGTAGA GGTGATTCAA AATTCCACGG CCAAAGTCAT         840

CGTGGTTTTC TCCAGTGGCC CAGATCTTGA GCCCCTCATC AAGGAGATTG TCCGGCGCAA         900

TATCACGGGC AAGATCTGGC TGGCCAGCGA GGCCTGGGCC AGCTCCTCCC TGATCGCCAT         960

GCCTCAGTAC TTCCACGTGG TTGGCGGCAC CATTGGATTC GCTCTGAAGG CTGGGCAGAT        1020

CCCAGGCTTC CGGGAATTCC TGAAGAAGGT CCATCCCAGG AAGTCTGTCC ACAATGGTTT        1080

TGCCAAGGAG TTTTGGGAAG AAACATTTAA CTGCCACCTC AAGAAGGTG CAAAAGGACC         1140

TTTACCTGTG GACACCTTTC TGAGAGGTCA CGAAGAAAGT GGCGACAGGT TTAGCAACAG        1200

CTCGACAGCC TTCCGACCCC TCTGTACAGG GGATGAGAAC ATCAGCAGTG TCGAGACCCC        1260

TTACATAGAT TACACGCATT TACGGATATC CTACAATGTG TACTTAGCAG TCTACTCCAT        1320

TGCCCACGCC TTGCAAGATA TATATACCTG CTTACCTGGG AGAGGCTCT TCACCAATGG        1380

CTCCTGTGCA GACATCAAGA AAGTTGAGGC GTGGCAGGTC CTGAAGCACC TACGGCATCT        1440

AAACTTTACA AACAATATGG GGGAGCAGGT GACCTTTGAT GAGTGTGGTG ACCTGGTGGG        1500

GAACTATTCC ATCATCAACT GGCACCTCTC CCCAGAGGAT GGCTCCATCG TGTTTAAGGA        1560

AGTCGGGTAT TACAACGTCT ATGCCAAGAA GGGAGAAAGA CTCTTCATCA ACGAGGAGAA        1620

AATCCTGTGG AGTGGGTTCT CCAGGGAGGT GCCCTTCTCC AACTGCAGCC GAGACTGCCT        1680

GGCAGGGACC AGGAAAGGGA TCATTGAGGG GGAGCCCACC TGCTGCTTTG AGTGTGTGGA        1740

GTGTCCTGAT GGGGAGTATA GTGATGAGAC AGATGCCAGT GCCTGTAACA AGTGCCCAGA        1800

TGACTTCTGG TCCAATGAGA ACCACACCTC CTGCGAGCCC ATTCCTGTCC GTTATCTTGA        1860
```

-continued

```
GTGGAGTGAC ATAGAATCTA TCATAGCCAT CGCCTTTTCT TGCCTGGGCA TCCTCGTGAC      1920

GCTGTTTGTC ACCCTCATCT TCGTTCTGTA CCGGGACACA CCCGTGGTCA AATCCTCCAG      1980

TAGGGAGCTC TGCTATATCA TTCTGGCTGG TATTTTCCTC GGCTATGTGT GCCCTTTCAC      2040

CCTCATCGCC AAACCTACTA CCACATCCTG CTACCTCCAG CGCCTCCTAG TTGGCCTCTC      2100

TTCTGCCATG TGCTACTCTG CTTTAGTGAC CAAAACCAAT CGTATTGCAC GCATCCTGGC      2160

TGGCAGCAAG AAGAAGATCT GCACCCGGAA GCCCAGATTC ATGAGCGCTT GGGCCCAAGT      2220

GATCATAGCC TCCATTCTGA TTAGTGTACA GCTAACACTA GTGGTGACCT TGATCATCAT      2280

GGAGCCTCCC ATGCCCATTT TGTCCTACCC GAGTATCAAG AAGTCTACC TTATCTGCAA       2340

TACCAGCAAC CTGGGTGTAG TGGCCCCTGT GGGTTACAAT GGACTCCTCA TCATGAGCTG      2400

TACCTACTAT GCCTTCAAGA CCCGCAACGT GCCGGCCAAC TTCAATGAGG CTAAATACAT      2460

CGCCTTCACC ATGTACACTA CCTGCATCAT CTGGCTGGCT TTCGTTCCCA TTTACTTTGG      2520

GAGCAACTAC AAGATCATCA CTACCTGCTT CGCGGTGAGC CTCAGTGTGA CGGTGGCCCT      2580

GGGGTGCATG TTTACTCCGA AGATGTACAT CATCATTGCC AAACCTGAGA GGAACGTCCG      2640

CAGTGCCTTC ACGACCTCTG ATGTTGTCCG CATGCACGTC GGTGATGGCA AACTGCCGTG      2700

CCGCTCCAAC ACCTTCCTCA ACATTTTCCG GAGAAAGAAG CCCGGGGCAG GAATGCCAA       2760

TTCTAACGGC AAGTCTGTGT CATGGTCTGA ACCAGGTGGA AGACAGGCGC CAAGGGACA      2820

GCACGTGTGG CAGCGCCTCT CTGTGCACGT GAAGACCAAC GAGACGGCCT GTAACCAAAC     2880

AGCCGTAATC AAACCCCTCA CTAAAAGTTA CCAAGGCTCT GGCAAGAGCC TGACCTTTTC     2940

AGATGCCAGC ACCAAGACCC TTTACAATGT GGAAGAAGAG GACAATACCC CTTCTGCTCA     3000

CTTCAGCCCT CCCAGCAGCC CTTCTATGGT GGTGCACCGA CGCGGGCCAC CCGTGGCCAC     3060

CACACCACCT CTGCCACCCC ATCTGACCGC AGAAGAGACC CCCCTGTTCC TGGCTGATTC     3120

CGTCATCCCC AAGGGCTTGC CTCCTCCTCT CCCGCAGCAG CAGCCACAGC AGCCGCCCCC     3180

TCAGCAGCCC CCGCAGCAGC CCAAGTCCCT GATGGACCAG CTGCAAGGCG TAGTCACCAA     3240

CTTCGGTTCG GGGATTCCAG ATTTCCATGC GGTGCTGGCA GGCCCGGGGA CACCAGGAAA     3300

CAGCCTGCGC TCTCTGTACC CGCCCCCGCC TCCGCCGCAA CACCTGCAGA TGCTGCCCCT     3360

GCACCTGAGC ACCTTCCAGG AGGAGTCCAT CTCCCCTCCT GGGGAGGACA TCGATGATGA     3420

CAGTGAGAGA TTCAAGCTCC TGCAGGAGTT CGTGTACGAG CGCGAAGGGA ACACCGAAGA     3480

AGATGAATTG GAAGAGGAGG AGGACCTGCC CACAGCCAGC AAGCTGACCC CTGAGGATTC     3540

TCCTGCCCTG ACGCCTCCTT CTCCTTTCCG AGATTCCGTG GCCTCTGGCA GCTCAGTGCC     3600

CAGTTCCCCC GTATCTGAGT CGGTCCTCTG CACCCCTCCA AATGTAACCT ACGCTCTGT      3660

CATTCTGAGG GACTACAAGC AAAGCTCTTC CACCCTGTAG TGTGTGTGTG TGTGTGGGGG     3720

CGGGGGGAGT GCGCATGGAG AAGCCAGAGA TGCCAAGGAG TGTCAACCCT TCCAGAAATG     3780

TGTAGAAAGC AGGGTGAGGG ATGGGATGG AGGACCACGG TCTGCAGGGA AGAAAAAAA       3840

AATGCTGCGG CTGCCTTAAA GAAGGAGAGG ACGATGCCA ACTGAACAGT GGTCCTGGCC      3900

AGGATTGTGA CTCTTGAATT ATTCAAAAAC CTTCTCTAGA AGAAAGGGA ATTATGACAA      3960

AGCACAATTC CATATGGTAT GTAACTTTTA TCGAAAAAAA                           4000
```

(2) INFORMATION FOR SEQ ID NO: 3:

(i) SEQUENCE CHARACTERISTICS:
        (A) LENGTH:        3219 base pairs
        (B) TYPE:          nucleic acid
        (C) STRANDEDNESS:   single (D) TOPOLOGY: linear (xi) SEQUENCE DESCRIPTION: SEQ ID NO: 3:

| | | | | | |
|---|---|---|---|---|---|
| GCGGTGGACC | GCGTCTTCGC | CACAATGGTC | CGGCTCCTCT | TGATTTTCTT | CCCAATGATC | 60
| TTTTTGGAGA | TGTCCATTTT | GCCCAGGATG | CCTGACAGAA | AAGTATTGCT | GGCAGGTGCC | 120
| TCGTCCCAGC | GCTCCGTGGC | GAGAATGGAC | GGAGATGTCA | TCATCGGAGC | CCTCTTCTCA | 180
| GTCCATCACC | AGCCTCCAGC | CGAGAAGGTA | CCCGAAAGGA | AGTGTGGGGA | GATCAGGGAA | 240
| CAGTATGGTA | TCCAGAGGGT | GGAGGCCATG | TTCCACACGT | TGGATAAGAT | TAACGCGGAC | 300
| CCGGTGCTCC | TGCCCAACAT | CACTCTGGGC | AGTGAGATCC | GGGACTCCTG | CTGGCACTCT | 360
| TCAGTGGCTC | TCGAACAGAG | CATCGAATTC | ATCAGAGACT | CCCTGATTTC | CATCCGAGAT | 420
| GAGAAGGATG | GGCTGAACCG | ATGCCTGCCT | GATGGCCAGA | CCCTGCCCCC | TGGCAGGACT | 480
| AAGAAGCCTA | TTGCTGGAGT | GATCGGCCCT | GGCTCCAGCT | CTGTGGCCAT | TCAAGTCCAG | 540
| AATCTTCTCC | AGCTGTTCGA | CATCCCACAG | ATCGCCTATT | CTGCCACAAG | CATAGACCTG | 600
| AGTGACAAAA | CTTTGTACAA | ATACTTCCTG | AGGGTGGTCC | CTTCTGACAC | TTTGCAGGCA | 660
| AGGGCGATGC | TCGACATAGT | CAAGCGTTAC | AACTGGACCT | ATGTCTCAGC | AGTCCACACA | 720
| GAAGGGAATT | ACGGCGAGAG | TGGAATGGAT | GCTTTCAAAG | AACTGGCTGC | CCAGGAAGGC | 780
| CTCTGCATCG | CACACTCGGA | CAAAATCTAC | AGCAATGCTG | GCGAGAAGAG | CTTTGACCGG | 840
| CTCCTGCGTA | AACTCCGGGA | GCGGCTTCCC | AAGGCCAGGG | TTGTGGTCTG | CTTCTGCGAG | 900
| GGCATGACAG | TGCGGGGCTT | ACTGAGTGCC | ATGCGCCGCC | TGGGCGTCGT | GGGCGAGTTC | 960
| TCACTCATTG | GAAGTGATGG | ATGGGCAGAC | AGAGATGAAG | TCATCGAAGG | CTATGAGGTG | 1020
| GAAGCCAACG | GAGGGATCAC | AATAAAGCTT | CAGTCTCCAG | AGGTCAGGTC | ATTTGATGAC | 1080
| TACTTCCTGA | AGCTGAGGCT | GGACACCAAC | ACAAGGAATC | CTTGGTTCCC | TGAGTTCTGG | 1140
| CAACATCGCT | TCCAGTGTCG | CCTACCTGGA | CACCTCTTGG | AAAACCCCAA | CTTTAAGAAA | 1200
| GTGTGCACAG | GAAATGAAAG | CTTGGAAGAA | AACTATGTCC | AGGACAGCAA | AATGGGATTT | 1260
| GTCATCAATG | CCATCTATGC | CATGGCACAT | GGGCTGCAGA | ACATGCACCA | TGCTCTGTGT | 1320
| CCCGGCCATG | TGGGCCTGTG | TGATGCTATG | AAACCCATTG | ATGGCAGGAA | GCTCCTGGAT | 1380
| TTCCTCATCA | AATCCTCTTT | TGTCGGAGTG | TCTGGAGAGG | AGGTGTGGTT | CGATGAGAAG | 1440
| GGGGATGCTC | CCGGAAGGTA | TGACATTATG | AATCTGCAGT | ACACAGAAGC | TAATCGCTAT | 1500
| GACTATGTCC | ACGTGGGGAC | CTGGCATGAA | GGAGTGCTGA | ATATTGATGA | TTACAAAATC | 1560
| CAGATGAACA | AAAGCGGAAT | GGTACGATCT | GTGTGCAGTG | AGCCTTGCTT | AAAGGGTCAG | 1620
| ATTAAGGTCA | TACGGAAAGG | AGAAGTGAGC | TGCTGCTGGA | TCTGCACGGC | CTGCAAAGAG | 1680
| AATGAGTTTG | TGCAGGACGA | GTTCACCTGC | AGAGCCTGTG | ACCTGGGGTG | GTGGCCCAAC | 1740
| GCAGAGCTCA | CAGGCTGTGA | GCCCATTCCT | GTCCGTTATC | TTGAGTGGAG | TGACATAGAA | 1800
| TCTATCATAG | CCATCGCCTT | TTCTTGCCTG | GGCATCCTCG | TGACGCTGTT | TGTCACCCTC | 1860
| ATCTTCGTTC | TGTACCGGGA | CACACCCGTG | GTCAAATCCT | CCAGTAGGGA | GCTCTGCTAT | 1920
| ATCATTCTGG | CTGGTATTTT | CCTCGGCTAT | GTGTGCCCTT | TCACCCTCAT | CGCCAAACCT | 1980
| ACTACCACAT | CCTGCTACCT | CCAGCGCCTC | CTAGTTGGCC | TCTCTTCTGC | CATGTGCTAC | 2040
| TCTGCTTTAG | TGACCAAAAC | CAATCGTATT | GCACGCATCC | TGGCTGGCAG | CAAGAAGAAG | 2100
| ATCTGCACCC | GGAAGCCCAG | ATTCATGAGC | GCTTGGGCCC | AAGTGATCAT | AGCCTCCATT | 2160
| CTGATTAGTG | TACAGCTAAC | ACTAGTGGTG | ACCTTGATCA | TCATGGAGCC | TCCCATGCCC | 2220
| ATTTTGTCCT | ACCCGAGTAT | CAAGGAAGTC | TACCTTATCT | GCAATACCAG | CAACCTGGGT | 2280

```
GTGGTGGCCC CTTTGGGCTA CAATGGACTC CTCATCATGA GCTGTACCTA CTATGCCTTC      2340

AAGACCCGCA ACGTGCCCGC CAACTTCAAC GAGGCCAAAT ATATCGCGTT CACCATGTAC      2400

ACCACCTGTA TCATCTGGCT AGCTTTTGTG CCCATTTACT TTGGGAGCAA CTACAAGATC      2460

ATCACAACTT GCTTTGCAGT GAGTCTCAGT GTAACAGTGG CTCTGGGGTG CATGTTCACT      2520

CCCAAGATGT ACATCATTAT TGCCAAGCCT GAGAGGAATA CCATCGAGGA GGTGCGTTGC      2580

AGCACCGCAG CTCACGCTTT CAAGGTGGCT GCCCGGGCCA CGCTGCGCCG CAGCAACGTC      2640

TCCCGCAAGC GGTCCAGCAG CCTTGGAGGC TCCACGGGAT CCACCCCCTC CTCCTCCATC      2700

AGCAGCAAGA GCAACAGCGA AGACCCATTC CCACAGCCCG AGAGGCAGAA GCAGCAGCAG      2760

CCGCTGGCCC TAACCCAGCA AGAGCAGCAG CAGCAGCCCC TGACCCTCCC ACAGCAGCAA      2820

CGATCTCAGC AGCAGCCCAG ATGCAAGCAG AAGGTCATCT TTGGCAGCGG CACGGTCACC      2880

TTCTCACTGA GCTTTGATGA GCCTCAGAAG AACGCCATGG CCCACGGGAA TTCTACGCAC      2940

CAGAACTCCC TGGAGGCCCA GAAAAGCAGC GATACGCTGA CCCGACACCA GCCATTACTC      3000

CCGCTGCAGT GCGGGGAAAC GGACTTAGAT CTGACCGTCC AGGAAACAGG TCTGCAAGGA      3060

CCTGTGGGTG GAGACCAGCG GCCAGAGGTG GAGGACCCTG AAGAGTTGTC CCCAGCACTT      3120

GTAGTGTCCA GTTCACAGAG CTTTGTCATC AGTGGTGGAG GCAGCACTGT TACAGAAAAC      3180

GTAGTGAATT CATAAAATGG AAGGAGAAGA CTGGGCTAG                             3219

(2) INFORMATION FOR SEQ ID NO: 4:

(i) SEQUENCE CHARACTERISTICS:
        (A) LENGTH:            3219 base pairs
        (B) TYPE:              nucleic acid
        (C) STRANDEDNESS:      single
        (D) TOPOLOGY:          linear (xi) SEQUENCE DESCRIPTION: SEQ ID NO: 4:

GCGGTGGACC GCGTCTTCGC CACAATGGTC CGGCTCCTCT TGATTTTCTT CCCAATGATC        60

TTTTTGGAGA TGTCCATTTT GCCCAGGATG CCTGACAGAA AAGTATTGCT GGCAGGTGCC       120

TCGTCCCAGC GCTCCGTGGC GAGAATGGAC GGAGATGTCA TCATCGGAGC CCTCTTCTCA       180

GTCCATCACC AGCCTCCAGC CGAGAAGGTA CCCGAAAGGA AGTGTGGGGA GATCAGGGAA       240

CAGTATGGTA TCCAGAGGGT GGAGGCCATG TTCCACACGT TGGATAAGAT TAACGCGGAC       300

CCGGTGCTCC TGCCCAACAT CACTCTGGGC AGTGAGATCC GGGACTCCTG CTGGCACTCT       360

TCAGTGGCTC TCGAACAGAG CATCGAATTC ATCAGAGACT CCCTGATTTC CATCCGAGAT       420

GAGAAGGATG GGCTGAACCG ATGCCTGCCT GATGGCCAGA CCCTGCCCCC TGGCAGGACT       480

AAGAAGCCTA TTGCTGGAGT GATCGGCCCT GGCTCCAGCT CTGTGGCCAT TCAAGTCCAG       540

AATCTTCTCC AGCTGTTCGA CATCCCACAG ATCGCCTATT CTGCCACAAG CATAGACCTG       600

AGTGACAAAA CTTTGTACAA ATACTTCCTG AGGGTTGTCC CTTCTGACAC TTTGCAGGCA       660

AGGGCCATGC TTGACATAGT CAAACGTTAC AATTGGACCT ATGTCTCTGC AGTCCACACG       720

GAAGGGAATT ATGGGGAGAG CGGAATGGAC GCTTTCAAAG AGCTGGCTGC CAGGAAGGC       780

CTCTGTATCG CCCATTCTGA CAAAATCTAC AGCAACGCTG GGGAGAAGAG CTTTGACCGA       840

CTCTTGCGCA AACTCCGAGA GAGGCTTCCC AAGGCTAGAG TGGTGGTCTG CTTCTGTGAA       900

GGCATGACAG TGCGAGGACT CCTGAGCGCC ATGCGGCGCC TTGGCGTCGT GGGCGAGTTC       960

TCACTCATTG GAAGTGATGG ATGGGCAGAC AGAGATGAAG TCATTGAAGG TTATGAGGTG       1020

GAAGCCAACG GGGAATCAC GATAAAGCTG CAGTCTCCAG AGGTCAGGTC ATTTGATGAT       1080

TATTTCCTGA AACTGAGGCT GGACACTAAC ACGAGGAATC CTGGTTCCC TGAGTTCTGG       1140
```

-continued

```
CAACATCGGT TCCAGTGCCG CCTTCCAGGA CACCTTCTGG AAAATCCCAA CTTTAAACGA    1200

ATCTGCACAG GCAATGAAAG CTTAGAAGAA AACTATGTCC AGGACAGTAA GATGGGGTTT    1260

GTCATCAATG CCATCTATGC CATGGCACAT GGGCTGCAGA ACATGCACCA TGCCCTCTGC    1320

CCTGGCCACG TGGGCCTCTG CGATGCCATG AAGCCCATCG ACGGCAGCAA GCTGCTGGAC    1380

TTCCTCATCA AGTCCTCATT CATTGGAGTA TCTGGAGAGG AGGTGTGGTT TGATGAGAAA    1440

GGAGACGCTC CTGGAAGGTA TGATATCATG AATCTGCAGT ACACTGAAGC TAATCGCTAT    1500

GACTATGTGC ACGTTGGAAC CTGGCATGAA GGAGTGCTGA ACATTGATGA TTACAAAATC    1560

CAGATGAACA AGAGTGGAGT GGTGCGGTCT GTGTGCAGTG AGCCTTGCTT AAAGGGCCAG    1620

ATTAAGGTTA TACGGAAAGG AGAAGTGAGC TGCTGCTGGA TTTGCACGGC CTGCAAAGAG    1680

AATGAATATG TGCAAGATGA GTTCACCTGC AAAGCTTGTG ACTTGGGATG GTGGCCCAAT    1740

GCAGATCTAA CAGGCTGTGA GCCCATTCCT GTGCGCTATC TTGAGTGGAG CAACATCGAA    1800

CCCATTATAG CCATCGCCTT TTCATGCCTG GGAATCCTTG TTACCTTGTT TGTCACCCTA    1860

ATCTTTGTAC TGTACCGGGA CACACCAGTG GTCAAATCCT CCAGTCGGGA GCTCTGCTAC    1920

ATCATCCTAG CTGGCATCTT CCTTGGTTAT GTGTGCCCAT TCACTCTCAT TGCCAAACCT    1980

ACTACCACCT CCTGCTACCT CCAGCGCCTC TTGGTTGGCC TCTCCTCTGC GATGTGCTAC    2040

TCTGCTTTAG TGACTAAAAC CAATCGTATT GCACGCATCC TGGCTGGCAG CAAGAAGAAG    2100

ATCTGCACCC GGAAGCCCAG GTTCATGAGT GCCTGGGCTC AGGTGATCAT TGCCTCAATT    2160

CTGATTAGTG TGCAACTAAC CCTGGTGGTA ACCCTGATCA TCATGGAACC CCCTATGCCC    2220

ATTCTGTCCT ACCCAAGTAT CAAGGAAGTC TACCTTATCT GCAATACCAG CAACCTGGGT    2280

GTGGTGGCCC CTTTGGGCTA CAATGGACTC CTCATCATGA GCTGTACCTA CTATGCCTTC    2340

AAGACCCGCA ACGTGCCCGC CAACTTCAAC GAGGCCAAAT ATATCGCGTT CACCATGTAC    2400

ACCACCTGTA TCATCTGGCT AGCTTTTGTG CCCATTTACT TTGGGAGCAA CTACAAGATC    2460

ATCACAACTT GCTTTGCAGT GAGTCTCAGT GTAACAGTGG CTCTGGGGTG CATGTTCACT    2520

CCCAAGATGT ACATCATTAT TGCCAAGCCT GAGAGGAATA CCATCGAGGA GGTGCGTTGC    2580

AGCACCGCAG CTCACGCTTT CAAGGTGGCT GCCCGGGCCA CGCTGCGCCG CAGCAACGTC    2640

TCCCGCAAGC GGTCCAGCAG CCTTGGAGGC TCCACGGGAT CCACCCCCTC CTCCTCCATC    2700

AGCAGCAAGA GCAACAGCGA AGACCCATTC CCACAGCCCG AGAGGCAGAA GCAGCAGCAG    2760

CCGCTGGCCC TAACCCAGCA AGAGCAGCAG CAGCAGCCCC TGACCCTCCC ACAGCAGCAA    2820

CGATCTCAGC AGCAGCCCAG ATGCAAGCAG AAGGTCATCT TTGGCAGCGG CACGGTCACC    2880

TTCTCACTGA GCTTTGATGA GCCTCAGAAG AACGCCATGG CCCACGGGAA TTCTACGCAC    2940

CAGAACTCCC TGGAGGCCCA GAAAAGCAGC GATACGCTGA CCCGACACCA GCCATTACTC    3000

CCGCTGCAGT GCGGGGAAAC GGACTTAGAT CTGACCGTCC AGGAAACAGG TCTGCAAGGA    3060

CCTGTGGGTG GAGACCAGCG GCCAGAGGTG GAGGACCCTG AAGAGTTGTC CCCAGCACTT    3120

GTAGTGTCCA GTTCACAGAG CTTTGTCATC AGTGGTGGAG GCAGCACTGT TACAGAAAAC    3180

GTAGTGAATT CATAAAATGG AAGGAGAAGA CTGGGCTAG                           3219
```

(2) INFORMATION FOR SEQ ID NO: 5:

(i) SEQUENCE CHARACTERISTICS:
        (A) LENGTH:       1058 amino acids
        (B) TYPE:         amino acid
        (C) STRANDEDNESS:  single
        (D) TOPOLOGY:     linear (ii) MOLECULE TYPE: Protein (xi) SEQUENCE DESCRIPTION: SEQ ID NO: 5:

```
Met Val Arg Leu Leu Ile Phe Phe Pro Met Ile Phe Leu Glu Met
 1               5                  10                  15

Ser Ile Leu Pro Arg Met Pro Asp Arg Lys Val Leu Leu Ala Gly Ala
            20                  25                  30

Ser Ser Gln Arg Ser Val Ala Arg Met Asp Gly Asp Val Ile Ile Gly
        35                  40                  45

Ala Leu Phe Ser Val His His Gln Pro Pro Ala Glu Lys Val Pro Glu
50                  55                  60

Arg Lys Cys Gly Glu Ile Arg Glu Gln Tyr Gly Ile Gln Arg Val Glu
65                  70                  75                  80

Ala Met Phe His Thr Leu Asp Lys Ile Asn Ala Asp Pro Val Leu Leu
                85                  90                  95

Pro Asn Ile Thr Leu Gly Ser Glu Ile Arg Asp Ser Cys Trp His Ser
            100                 105                 110

Ser Val Ala Leu Glu Gln Ser Ile Glu Phe Ile Arg Asp Ser Leu Ile
        115                 120                 125

Ser Ile Arg Asp Glu Lys Asp Gly Leu Asn Arg Cys Leu Pro Asp Gly
130                 135                 140

Gln Thr Leu Pro Pro Gly Arg Thr Lys Lys Pro Ile Ala Gly Val Ile
145                 150                 155                 160

Gly Pro Gly Ser Ser Ser Val Ala Ile Gln Val Gln Asn Leu Leu Gln
                165                 170                 175

Leu Phe Asp Ile Pro Gln Ile Ala Tyr Ser Ala Thr Ser Ile Asp Leu
            180                 185                 190

Ser Asp Lys Thr Leu Tyr Lys Tyr Phe Leu Arg Val Val Pro Ser Asp
        195                 200                 205

Thr Leu Gln Ala Arg Ala Met Leu Asp Ile Val Lys Arg Tyr Asn Trp
210                 215                 220

Thr Tyr Val Ser Ala Val His Thr Glu Gly Asn Tyr Gly Glu Ser Gly
225                 230                 235                 240

Met Asp Ala Phe Lys Glu Leu Ala Ala Gln Glu Gly Leu Cys Ile Ala
                245                 250                 255

His Ser Asp Lys Ile Tyr Ser Asn Ala Gly Glu Lys Ser Phe Asp Arg
            260                 265                 270

Leu Leu Arg Lys Leu Arg Glu Arg Leu Pro Lys Ala Arg Val Val Val
        275                 280                 285

Cys Phe Cys Glu Gly Met Thr Val Arg Gly Leu Leu Ser Ala Met Arg
290                 295                 300

Arg Leu Gly Val Val Gly Glu Phe Ser Leu Ile Gly Ser Asp Gly Trp
305                 310                 315                 320

Ala Asp Arg Asp Glu Val Ile Glu Gly Tyr Glu Val Glu Ala Asn Gly
                325                 330                 335

Gly Ile Thr Ile Lys Leu Gln Ser Pro Glu Val Arg Ser Phe Asp Asp
            340                 345                 350

Tyr Phe Leu Lys Leu Arg Leu Asp Thr Asn Thr Arg Asn Pro Trp Phe
        355                 360                 365

Pro Glu Phe Trp Gln His Arg Phe Gln Cys Arg Leu Pro Gly His Leu
370                 375                 380

Leu Glu Asn Pro Asn Phe Lys Lys Val Cys Thr Gly Asn Glu Ser Leu
385                 390                 395                 400
```

-continued

| | | | | | | | | | | | |
|---|---|---|---|---|---|---|---|---|---|---|---|
|Glu|Glu|Asn|Tyr|Val|Gln|Asp|Ser|Lys|Met|Gly|Phe|Val|Ile|Asn|Ala
| | | |405| | | |410| | | |415

Ile Tyr Ala Met Ala His Gly Leu Gln Asn Met His His Ala Leu Cys
            420              425              430

Pro Gly His Val Gly Leu Cys Asp Ala Met Lys Pro Ile Asp Gly Arg
            435              440              445

Lys Leu Leu Asp Phe Leu Ile Lys Ser Ser Phe Val Gly Val Ser Gly
        450              455              460

Glu Glu Val Trp Phe Asp Glu Lys Gly Asp Ala Pro Gly Arg Tyr Asp
465              470              475              480

Ile Met Asn Leu Gln Tyr Thr Glu Ala Asn Arg Tyr Asp Tyr Val His
                485              490              495

Val Gly Thr Trp His Glu Gly Val Leu Asn Ile Asp Asp Tyr Lys Ile
            500              505              510

Gln Met Asn Lys Ser Gly Met Val Arg Ser Val Cys Ser Glu Pro Cys
            515              520              525

Leu Lys Gly Gln Ile Lys Val Ile Arg Lys Gly Glu Val Ser Cys Cys
        530              535              540

Trp Ile Cys Thr Ala Cys Lys Glu Asn Glu Phe Val Gln Asp Glu Phe
545              550              555              560

Thr Cys Arg Ala Cys Asp Leu Gly Trp Trp Pro Asn Ala Glu Leu Thr
                565              570              575

Gly Cys Glu Pro Ile Pro Val Arg Tyr Leu Glu Trp Ser Asp Ile Glu
            580              585              590

Gly Ile Ala Leu Thr Leu Phe Ala Val Leu Gly Ile Phe Leu Thr Ala
        595              600              605

Phe Val Leu Gly Val Phe Ile Lys Phe Arg Asn Thr Pro Ile Val Lys
        610              615              620

Ala Thr Asn Arg Glu Leu Ser Tyr Leu Leu Leu Phe Ser Leu Leu Cys
625              630              635              640

Cys Phe Ser Ser Ser Leu Phe Phe Ile Gly Glu Pro Gln Asp Trp Thr
                645              650              655

Cys Arg Leu Arg Gln Pro Ala Phe Gly Ile Ser Phe Val Leu Cys Ile
            660              665              670

Ser Cys Ile Leu Val Lys Thr Asn Arg Val Leu Leu Val Phe Glu Ala
        675              680              685

Lys Ile Pro Thr Ser Phe His Arg Lys Trp Trp Gly Leu Asn Leu Gln
690              695              700

Phe Leu Leu Val Phe Leu Cys Thr Phe Met Gln Ile Val Ile Cys Val
705              710              715              720

Ile Trp Leu Tyr Thr Ala Pro Pro Ser Ser Tyr Arg Asn Gln Glu Leu
            725              730              735

Glu Asp Glu Ile Ile Phe Ile Thr Cys His Glu Gly Ser Leu Met Ala
        740              745              750

Leu Gly Phe Leu Ile Gly Tyr Thr Cys Leu Leu Ala Ala Ile Cys Phe
        755              760              765

Phe Phe Ala Phe Lys Ser Arg Lys Leu Pro Glu Asn Phe Asn Glu Ala
        770              775              780

Lys Phe Ile Thr Phe Ser Met Leu Ile Phe Phe Ile Val Trp Ile Ser
785              790              795              800

Phe Ile Pro Ala Tyr Ala Ser Thr Tyr Gly Lys Phe Val Ser Ala Val
            805              810              815

Glu Val Ile Ala Ile Leu Ala Ala Ser Phe Gly Leu Leu Ala Cys Ile
            820              825              830

Phe Phe Asn Lys Ile Tyr Ile Ile Leu Phe Lys Pro Ser Arg Asn Thr
            835                 840                 845

Ile Glu Glu Val Arg Cys Ser Thr Ala Ala His Ala Phe Lys Val Ala
850                 855                 860

Ala Arg Ala Thr Leu Arg Arg Ser Asn Val Ser Arg Lys Arg Ser Ser
865                 870                 875                 880

Ser Leu Gly Gly Ser Thr Gly Ser Thr Pro Ser Ser Ile Ser Ser
            885                 890                 895

Lys Ser Asn Ser Glu Asp Pro Phe Pro Gln Pro Glu Arg Gln Lys Gln
            900                 905                 910

Gln Gln Pro Leu Ala Leu Thr Gln Gln Glu Gln Gln Gln Pro Leu
            915                 920                 925

Thr Leu Pro Gln Gln Gln Arg Ser Gln Gln Gln Pro Arg Cys Lys Gln
            930                 935                 940

Lys Val Ile Phe Gly Ser Gly Thr Val Thr Phe Ser Leu Ser Phe Asp
945                 950                 955                 960

Glu Pro Gln Lys Asn Ala Met Ala His Gly Asn Ser Thr His Gln Asn
            965                 970                 975

Ser Leu Glu Ala Gln Lys Ser Ser Asp Thr Leu Thr Arg His Gln Pro
            980                 985                 990

Leu Leu Pro Leu Gln Cys Gly Glu Thr Asp Leu Asp Leu Thr Val Gln
            995                 1000                1005

Glu Thr Gly Leu Gln Gly Pro Val Gly Gly Asp Gln Arg Pro Glu Val
            1010                1015                1020

Glu Asp Pro Glu Glu Leu Ser Pro Ala Leu Val Val Ser Ser Gln
025                 1030                1035                1040

Ser Phe Val Ile Ser Gly Gly Ser Thr Val Thr Glu Asn Val Val
            1045                1050                1055

Asn Ser (2) INFORMATION FOR SEQ ID NO: 6:

(i) SEQUENCE CHARACTERISTICS:
        (A) LENGTH:        1219 amino acids
        (B) TYPE:          amino acid
        (C) STRANDEDNESS:   single
        (D) TOPOLOGY:     linear (ii) MOLECULE TYPE:      Protein (xi) SEQUENCE DESCRIPTION: SEQ ID NO: 6:

Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
            35                  40                  45

Gln Asp Leu Lys Ser Arg Pro Glu Ser Val Glu Cys Ile Arg Tyr Asn
50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
            85                  90                  95

Ile Phe Asp Thr Cys Asn Thr Val Ser Lys Ala Leu Glu Ala Thr Leu
            100                 105                 110

```
Ser Phe Val Ala Gln Asn Lys Ile Asp Ser Leu Asn Leu Asp Glu Phe
            115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
                180                 185                 190

Gln Ala Thr Ala Met Ala Asp Ile Ile Glu Tyr Phe Arg Trp Asn Trp
            195                 200                 205

Val Gly Thr Ile Ala Ala Asp Asp Tyr Gly Arg Pro Gly Ile Glu
            210                 215                 220

Lys Phe Arg Glu Glu Ala Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255

Glu Val Ile Gln Asn Ser Thr Ala Lys Val Ile Val Phe Ser Ser
                260                 265                 270

Gly Pro Asp Leu Glu Pro Leu Ile Lys Glu Ile Val Arg Arg Asn Ile
    275                 280                 285

Thr Gly Lys Ile Trp Leu Ala Ser Glu Ala Trp Ala Ser Ser Ser Leu
    290                 295                 300

Ile Ala Met Pro Gln Tyr Phe His Val Val Gly Thr Ile Gly Phe
305                 310                 315                 320

Ala Leu Lys Ala Gly Gln Ile Pro Gly Phe Arg Glu Phe Leu Lys Lys
            325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
            355                 360                 365

Pro Val Asp Thr Phe Leu Arg Gly His Glu Glu Ser Gly Asp Arg Phe
    370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                405                 410                 415

Ser Tyr Asn Val Tyr Leu Ala Val Tyr Ser Ile Ala His Ala Leu Gln
                420                 425                 430

Asp Ile Tyr Thr Cys Leu Pro Gly Arg Gly Leu Phe Thr Asn Gly Ser
            435                 440                 445

Cys Ala Asp Ile Lys Lys Val Glu Ala Trp Gln Val Leu Lys His Leu
    450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
                500                 505                 510

Val Tyr Ala Lys Lys Gly Glu Arg Leu Phe Ile Asn Glu Glu Lys Ile
            515                 520                 525

Leu Trp Ser Gly Phe Ser Arg Glu Val Pro Phe Ser Asn Cys Ser Arg
    530                 535                 540
```

-continued

```
Asp Cys Leu Ala Gly Thr Arg Lys Gly Ile Ile Glu Gly Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asn Lys Cys Pro Asp Asp Phe Trp Ser Asn
                580                 585                 590

Glu Asn His Thr Ser Cys Glu Pro Ile Pro Val Arg Tyr Leu Glu Trp
            595                 600                 605

Ser Asp Ile Glu Ser Ile Ile Ala Ile Ala Phe Ser Cys Leu Gly Ile
            610                 615                 620

Leu Val Thr Leu Phe Val Thr Leu Ile Phe Val Leu Tyr Arg Asp Thr
625                 630                 635                 640

Pro Val Val Lys Ser Ser Arg Glu Leu Cys Tyr Ile Ile Leu Ala
                645                 650                 655

Gly Ile Phe Leu Gly Tyr Val Cys Pro Phe Thr Leu Ile Ala Lys Pro
                660                 665                 670

Thr Thr Thr Ser Cys Tyr Leu Gln Arg Leu Leu Val Gly Leu Ser Ser
            675                 680                 685

Ala Met Cys Tyr Ser Ala Leu Val Thr Lys Thr Asn Arg Ile Ala Arg
690                 695                 700

Ile Leu Ala Gly Ser Lys Lys Ile Cys Thr Arg Lys Pro Arg Phe
705                 710                 715                 720

Met Ser Ala Trp Ala Gln Val Ile Ile Ala Ser Ile Leu Ile Ser Val
                725                 730                 735

Gln Leu Thr Leu Val Val Thr Leu Ile Ile Met Glu Pro Pro Met Pro
            740                 745                 750

Ile Leu Ser Tyr Pro Ser Ile Lys Glu Val Tyr Leu Ile Cys Asn Thr
            755                 760                 765

Ser Asn Leu Gly Val Val Ala Pro Val Gly Tyr Asn Gly Leu Leu Ile
            770                 775                 780

Met Ser Cys Thr Tyr Tyr Ala Phe Lys Thr Arg Asn Val Pro Ala Asn
785                 790                 795                 800

Phe Asn Glu Ala Lys Tyr Ile Ala Phe Thr Met Tyr Thr Thr Cys Ile
                805                 810                 815

Ile Trp Leu Ala Phe Val Pro Ile Tyr Phe Gly Ser Asn Tyr Lys Ile
                820                 825                 830

Ile Thr Thr Cys Phe Ala Val Ser Leu Ser Val Thr Val Ala Leu Gly
            835                 840                 845

Cys Met Phe Thr Pro Lys Met Tyr Ile Ile Ile Ala Lys Pro Glu Arg
850                 855                 860

Asn Val Arg Ser Ala Phe Thr Thr Ser Asp Val Val Arg Met His Val
865                 870                 875                 880

Gly Asp Gly Lys Leu Pro Cys Arg Ser Asn Thr Phe Leu Asn Ile Phe
                885                 890                 895

Arg Arg Lys Lys Pro Gly Ala Gly Asn Ala Asn Ser Asn Gly Lys Ser
                900                 905                 910

Val Ser Trp Ser Glu Pro Gly Gly Arg Gln Ala Pro Lys Gly Gln His
            915                 920                 925

Val Trp Gln Arg Leu Ser Val His Val Lys Thr Asn Glu Thr Ala Cys
930                 935                 940

Asn Gln Thr Ala Val Ile Lys Pro Leu Thr Lys Ser Tyr Gln Gly Ser
945                 950                 955                 960
```

-continued

```
Gly Lys Ser Leu Thr Phe Ser Asp Ala Ser Thr Lys Thr Leu Tyr Asn
            965                 970                 975

Val Glu Glu Glu Asp Asn Thr Pro Ser Ala His Phe Ser Pro Pro Ser
            980                 985                 990

Ser Pro Ser Met Val Val His Arg Arg Gly Pro Pro Val Ala Thr Thr
            995                1000                1005

Pro Pro Leu Pro Pro His Leu Thr Ala Glu Glu Thr Pro Leu Phe Leu
           1010                1015                1020

Ala Asp Ser Val Ile Pro Lys Gly Leu Pro Pro Leu Pro Gln Gln
025                1030                1035                1040

Gln Pro Gln Gln Pro Pro Gln Gln Pro Pro Gln Gln Pro Lys Ser
           1045                1050                1055

Leu Met Asp Gln Leu Gln Gly Val Val Thr Asn Phe Gly Ser Gly Ile
           1060                1065                1070

Pro Asp Phe His Ala Val Leu Ala Gly Pro Gly Thr Pro Gly Asn Ser
           1075                1080                1085

Leu Arg Ser Leu Tyr Pro Pro Pro Pro Pro Gln His Leu Gln Met
           1090                1095                1100

Leu Pro Leu His Leu Ser Thr Phe Gln Glu Glu Ser Ile Ser Pro Pro
105                1110                1115                1120

Gly Glu Asp Ile Asp Asp Asp Ser Glu Arg Phe Lys Leu Leu Gln Glu
           1125                1130                1135

Phe Val Tyr Glu Arg Glu Gly Asn Thr Glu Glu Asp Glu Leu Glu Glu
           1140                1145                1150

Glu Glu Asp Leu Pro Thr Ala Ser Lys Leu Thr Pro Glu Asp Ser Pro
           1155                1160                1165

Ala Leu Thr Pro Pro Ser Pro Phe Arg Asp Ser Val Ala Ser Gly Ser
           1170                1175                1180

Ser Val Pro Ser Ser Pro Val Ser Glu Ser Val Leu Cys Thr Pro Pro
185                1190                1195                1200

Asn Val Thr Tyr Ala Ser Val Ile Leu Arg Asp Tyr Lys Gln Ser Ser
           1205                1210                1215

Ser Thr Leu
```

(2) INFORMATION FOR SEQ ID NO: 7:

(i) SEQUENCE CHARACTERISTICS:
        (A) LENGTH:        1056 amino acids
        (B) TYPE:          amino acid
        (C) STRANDEDNESS:   single
        (D) TOPOLOGY:      linear (ii) MOLECULE TYPE:      Protein (xi) SEQUENCE DESCRIPTION: SEQ ID NO: 7:

```
Met Val Arg Leu Leu Leu Ile Phe Phe Pro Met Ile Phe Leu Glu Met
  1               5                  10                  15

Ser Ile Leu Pro Arg Met Pro Asp Arg Lys Val Leu Leu Ala Gly Ala
             20                  25                  30

Ser Ser Gln Arg Ser Val Ala Arg Met Asp Gly Asp Val Ile Ile Gly
             35                  40                  45

Ala Leu Phe Ser Val His His Gln Pro Ala Glu Lys Val Pro Glu
 50                  55                  60

Arg Lys Cys Gly Glu Ile Arg Glu Gln Tyr Gly Ile Gln Arg Val Glu
 65                  70                  75                  80

Ala Met Phe His Thr Leu Asp Lys Ile Asn Ala Asp Pro Val Leu Leu
             85                  90                  95
```

```
Pro Asn Ile Thr Leu Gly Ser Glu Ile Arg Asp Ser Cys Trp His Ser
            100                 105                 110

Ser Val Ala Leu Glu Gln Ser Ile Glu Phe Ile Arg Asp Ser Leu Ile
        115                 120                 125

Ser Ile Arg Asp Glu Lys Asp Gly Leu Asn Arg Cys Leu Pro Asp Gly
    130                 135                 140

Gln Thr Leu Pro Pro Gly Arg Thr Lys Lys Pro Ile Ala Gly Val Ile
145                 150                 155                 160

Gly Pro Gly Ser Ser Val Ala Ile Gln Val Gln Asn Leu Leu Gln
                165                 170                 175

Leu Phe Asp Ile Pro Gln Ile Ala Tyr Ser Ala Thr Ser Ile Asp Leu
            180                 185                 190

Ser Asp Lys Thr Leu Tyr Lys Tyr Phe Leu Arg Val Val Pro Ser Asp
        195                 200                 205

Thr Leu Gln Ala Arg Ala Met Leu Asp Ile Val Lys Arg Tyr Asn Trp
            210                 215                 220

Thr Tyr Val Ser Ala Val His Thr Glu Gly Asn Tyr Gly Glu Ser Gly
225                 230                 235                 240

Met Asp Ala Phe Lys Glu Leu Ala Ala Gln Glu Gly Leu Cys Ile Ala
                245                 250                 255

His Ser Asp Lys Ile Tyr Ser Asn Ala Gly Glu Lys Ser Phe Asp Arg
            260                 265                 270

Leu Leu Arg Lys Leu Arg Glu Arg Leu Pro Lys Ala Arg Val Val Val
        275                 280                 285

Cys Phe Cys Glu Gly Met Thr Val Arg Gly Leu Leu Ser Ala Met Arg
    290                 295                 300

Arg Leu Gly Val Val Gly Glu Phe Ser Leu Ile Gly Ser Asp Gly Trp
305                 310                 315                 320

Ala Asp Arg Asp Glu Val Ile Glu Gly Tyr Glu Val Glu Ala Asn Gly
                325                 330                 335

Gly Ile Thr Ile Lys Leu Gln Ser Pro Glu Val Arg Ser Phe Asp Asp
            340                 345                 350

Tyr Phe Leu Lys Leu Arg Leu Asp Thr Asn Thr Arg Asn Pro Trp Phe
        355                 360                 365

Pro Glu Phe Trp Gln His Arg Phe Gln Cys Arg Leu Pro Gly His Leu
    370                 375                 380

Leu Glu Asn Pro Asn Phe Lys Lys Val Cys Thr Gly Asn Glu Ser Leu
385                 390                 395                 400

Glu Glu Asn Tyr Val Gln Asp Ser Lys Met Gly Phe Val Ile Asn Ala
                405                 410                 415

Ile Tyr Ala Met Ala His Gly Leu Gln Asn Met His His Ala Leu Cys
            420                 425                 430

Pro Gly His Val Gly Leu Cys Asp Ala Met Lys Pro Ile Asp Gly Arg
        435                 440                 445

Lys Leu Leu Asp Phe Leu Ile Lys Ser Ser Phe Val Gly Val Ser Gly
    450                 455                 460

Glu Glu Val Trp Phe Asp Glu Lys Gly Asp Ala Pro Gly Arg Tyr Asp
465                 470                 475                 480

Ile Met Asn Leu Gln Tyr Thr Glu Ala Asn Arg Tyr Asp Tyr Val His
                485                 490                 495

Val Gly Thr Trp His Glu Gly Val Leu Asn Ile Asp Asp Tyr Lys Ile
            500                 505                 510
```

```
Gln Met Asn Lys Ser Gly Met Val Arg Ser Val Cys Ser Glu Pro Cys
        515                 520                 525

Leu Lys Gly Gln Ile Lys Val Ile Arg Lys Gly Val Ser Cys Cys
    530                 535                 540

Trp Ile Cys Thr Ala Cys Lys Glu Asn Glu Phe Val Gln Asp Glu Phe
545                 550                 555                 560

Thr Cys Arg Ala Cys Asp Leu Gly Trp Trp Pro Asn Ala Glu Leu Thr
                565                 570                 575

Gly Cys Glu Pro Ile Pro Val Arg Tyr Leu Glu Trp Ser Asp Ile Glu
                580                 585                 590

Ser Ile Ile Ala Ile Ala Phe Ser Cys Leu Gly Ile Leu Val Thr Leu
                595                 600                 605

Phe Val Thr Leu Ile Phe Val Leu Tyr Arg Asp Thr Pro Val Val Lys
        610                 615                 620

Ser Ser Ser Arg Glu Leu Cys Tyr Ile Ile Leu Ala Gly Ile Phe Leu
625                 630                 635                 640

Gly Tyr Val Cys Pro Phe Thr Leu Ile Ala Lys Pro Thr Thr Thr Ser
                645                 650                 655

Cys Tyr Leu Gln Arg Leu Leu Val Gly Leu Ser Ser Ala Met Cys Tyr
                660                 665                 670

Ser Ala Leu Val Thr Lys Thr Asn Arg Ile Ala Arg Ile Leu Ala Gly
        675                 680                 685

Ser Lys Lys Lys Ile Cys Thr Arg Lys Pro Arg Phe Met Ser Ala Trp
690                 695                 700

Ala Gln Val Ile Ile Ala Ser Ile Leu Ile Ser Val Gln Leu Thr Leu
705                 710                 715                 720

Val Val Thr Leu Ile Ile Met Glu Pro Pro Met Pro Ile Leu Ser Tyr
                725                 730                 735

Pro Ser Ile Lys Glu Val Tyr Leu Ile Cys Asn Thr Ser Asn Leu Gly
                740                 745                 750

Val Val Ala Pro Leu Gly Tyr Asn Gly Leu Leu Ile Met Ser Cys Thr
                755                 760                 765

Tyr Tyr Ala Phe Lys Thr Arg Asn Val Pro Ala Asn Phe Asn Glu Ala
        770                 775                 780

Lys Tyr Ile Ala Phe Thr Met Tyr Thr Thr Cys Ile Ile Trp Leu Ala
785                 790                 795                 800

Phe Val Pro Ile Tyr Phe Gly Ser Asn Tyr Lys Ile Ile Thr Thr Cys
                805                 810                 815

Phe Ala Val Ser Leu Ser Val Thr Val Ala Leu Gly Cys Met Phe Thr
                820                 825                 830

Pro Lys Met Tyr Ile Ile Ile Ala Lys Pro Glu Arg Asn Thr Ile Glu
        835                 840                 845

Glu Val Arg Cys Ser Thr Ala Ala His Ala Phe Lys Val Ala Ala Arg
850                 855                 860

Ala Thr Leu Arg Arg Ser Asn Val Ser Arg Lys Arg Ser Ser Ser Leu
865                 870                 875                 880

Gly Gly Ser Thr Gly Ser Thr Pro Ser Ser Ser Ile Ser Ser Lys Ser
                885                 890                 895

Asn Ser Glu Asp Pro Phe Pro Gln Pro Glu Arg Gln Lys Gln Gln Gln
                900                 905                 910

Pro Leu Ala Leu Thr Gln Gln Glu Gln Gln Gln Gln Pro Leu Thr Leu
        915                 920                 925

Pro Gln Gln Gln Arg Ser Gln Gln Gln Pro Arg Cys Lys Gln Lys Val
930                 935                 940
```

Ile Phe Gly Ser Gly Thr Val Thr Phe Ser Leu Ser Phe Asp Glu Pro
945                 950                 955                 960

Gln Lys Asn Ala Met Ala His Gly Asn Ser Thr His Gln Asn Ser Leu
            965                 970                 975

Glu Ala Gln Lys Ser Ser Asp Thr Leu Thr Arg His Gln Pro Leu Leu
            980                 985                 990

Pro Leu Gln Cys Gly Glu Thr Asp Leu Asp Leu Thr Val Gln Glu Thr
            995                 1000                1005

Gly Leu Gln Gly Pro Val Gly Gly Asp Gln Arg Pro Glu Val Glu Asp
    1010                1015                1020

Pro Glu Glu Leu Ser Pro Ala Leu Val Val Ser Ser Ser Gln Ser Phe
025                 1030                1035                1040

Val Ile Ser Gly Gly Gly Ser Thr Val Thr Glu Asn Val Val Asn Ser
            1045                1050                1055

(2) INFORMATION FOR SEQ ID NO: 8:

(i) SEQUENCE CHARACTERISTICS:
        (A) LENGTH:         1056 amino acids
        (B) TYPE:           amino acid
        (C) STRANDEDNESS:   single
        (D) TOPOLOGY:       linear (ii) MOLECULE TYPE:         Protein (xi) SEQUENCE DESCRIPTION: SEQ ID NO: 8:

Met Val Arg Leu Leu Ile Phe Phe Pro Met Ile Phe Leu Glu Met
1               5                   10                  15

Ser Ile Leu Pro Arg Met Pro Asp Arg Lys Val Leu Leu Ala Gly Ala
            20                  25                  30

Ser Ser Gln Arg Ser Val Ala Arg Met Asp Gly Asp Val Ile Ile Gly
            35                  40                  45

Ala Leu Phe Ser Val His His Gln Pro Pro Ala Glu Lys Val Pro Glu
    50                  55                  60

Arg Lys Cys Gly Glu Ile Arg Glu Gln Tyr Gly Ile Gln Arg Val Glu
65                  70                  75                  80

Ala Met Phe His Thr Leu Asp Lys Ile Asn Ala Asp Pro Val Leu Leu
            85                  90                  95

Pro Asn Ile Thr Leu Gly Ser Glu Ile Arg Asp Ser Cys Trp His Ser
            100                 105                 110

Ser Val Ala Leu Glu Gln Ser Ile Glu Phe Ile Arg Asp Ser Leu Ile
            115                 120                 125

Ser Ile Arg Asp Glu Lys Asp Gly Leu Asn Arg Cys Leu Pro Asp Gly
            130                 135                 140

Gln Thr Leu Pro Pro Gly Arg Thr Lys Lys Pro Ile Ala Gly Val Ile
145                 150                 155                 160

Gly Pro Gly Ser Ser Ser Val Ala Ile Gln Val Gln Asn Leu Leu Gln
            165                 170                 175

Leu Phe Asp Ile Pro Gln Ile Ala Tyr Ser Ala Thr Ser Ile Asp Leu
            180                 185                 190

Ser Asp Lys Thr Leu Tyr Lys Tyr Phe Leu Arg Val Val Pro Ser Asp
            195                 200                 205

Thr Leu Gln Ala Arg Ala Met Leu Asp Ile Val Lys Arg Tyr Asn Trp
    210                 215                 220

Thr Tyr Val Ser Ala Val His Thr Glu Gly Asn Tyr Gly Glu Ser Gly
225                 230                 235                 240

-continued

```
Met Asp Ala Phe Lys Glu Leu Ala Ala Gln Glu Gly Leu Cys Ile Ala
            245                 250                 255

His Ser Asp Lys Ile Tyr Ser Asn Ala Gly Glu Lys Ser Phe Asp Arg
            260                 265                 270

Leu Leu Arg Lys Leu Arg Glu Arg Leu Pro Lys Ala Arg Val Val Val
            275                 280                 285

Cys Phe Cys Glu Gly Met Thr Val Arg Gly Leu Leu Ser Ala Met Arg
290                 295                 300

Arg Leu Gly Val Val Gly Glu Phe Ser Leu Ile Gly Ser Asp Gly Trp
305                 310                 315                 320

Ala Asp Arg Asp Glu Val Ile Glu Gly Tyr Glu Val Glu Ala Asn Gly
                325                 330                 335

Gly Ile Thr Ile Lys Leu Gln Ser Pro Glu Val Arg Ser Phe Asp Asp
                340                 345                 350

Tyr Phe Leu Lys Leu Arg Leu Asp Thr Asn Thr Arg Asn Pro Trp Phe
            355                 360                 365

Pro Glu Phe Trp Gln His Arg Phe Gln Cys Arg Leu Pro Gly His Leu
370                 375                 380

Leu Glu Asn Pro Asn Phe Lys Arg Ile Cys Thr Gly Asn Glu Ser Leu
385                 390                 395                 400

Glu Glu Asn Tyr Val Gln Asp Ser Lys Met Gly Phe Val Ile Asn Ala
                405                 410                 415

Ile Tyr Ala Met Ala His Gly Leu Gln Asn Met His His Ala Leu Cys
            420                 425                 430

Pro Gly His Val Gly Leu Cys Asp Ala Met Lys Pro Ile Asp Gly Ser
            435                 440                 445

Lys Leu Leu Asp Phe Leu Ile Lys Ser Ser Phe Ile Gly Val Ser Gly
            450                 455                 460

Glu Glu Val Trp Phe Asp Glu Lys Gly Asp Ala Pro Gly Arg Tyr Asp
465                 470                 475                 480

Ile Met Asn Leu Gln Tyr Thr Glu Ala Asn Arg Tyr Asp Tyr Val His
                485                 490                 495

Val Gly Thr Trp His Glu Gly Val Leu Asn Ile Asp Asp Tyr Lys Ile
            500                 505                 510

Gln Met Asn Lys Ser Gly Val Val Arg Ser Val Cys Ser Glu Pro Cys
            515                 520                 525

Leu Lys Gly Gln Ile Lys Val Ile Arg Lys Gly Glu Val Ser Cys Cys
530                 535                 540

Trp Ile Cys Thr Ala Cys Lys Glu Asn Glu Tyr Val Gln Asp Glu Phe
545                 550                 555                 560

Thr Cys Lys Ala Cys Asp Leu Gly Trp Trp Pro Asn Ala Asp Leu Thr
                565                 570                 575

Gly Cys Glu Pro Ile Pro Val Arg Tyr Leu Glu Trp Ser Asn Ile Glu
            580                 585                 590

Pro Ile Ile Ala Ile Ala Phe Ser Cys Leu Gly Ile Leu Val Thr Leu
            595                 600                 605

Phe Val Thr Leu Ile Phe Val Leu Tyr Arg Asp Thr Pro Val Val Lys
            610                 615                 620

Ser Ser Ser Arg Glu Leu Cys Tyr Ile Ile Leu Ala Gly Ile Phe Leu
625                 630                 635                 640

Gly Tyr Val Cys Pro Phe Thr Leu Ile Ala Lys Pro Thr Thr Thr Ser
                645                 650                 655

Cys Tyr Leu Gln Arg Leu Leu Val Gly Leu Ser Ser Ala Met Cys Tyr
            660                 665                 670
```

```
Ser Ala Leu Val Thr Lys Thr Asn Arg Ile Ala Arg Ile Leu Ala Gly
            675                 680                 685

Ser Lys Lys Lys Ile Cys Thr Arg Lys Pro Arg Phe Met Ser Ala Trp
        690                 695                 700

Ala Gln Val Ile Ile Ala Ser Ile Leu Ile Ser Val Gln Leu Thr Leu
705                     710                 715                 720

Val Val Thr Leu Ile Ile Met Glu Pro Pro Met Pro Ile Leu Ser Tyr
                    725                 730                 735

Pro Ser Ile Lys Glu Val Tyr Leu Ile Cys Asn Thr Ser Asn Leu Gly
                740                 745                 750

Val Val Ala Pro Leu Gly Tyr Asn Gly Leu Leu Ile Met Ser Cys Thr
            755                 760                 765

Tyr Tyr Ala Phe Lys Thr Arg Asn Val Pro Ala Asn Phe Asn Glu Ala
    770                 775                 780

Lys Tyr Ile Ala Phe Thr Met Tyr Thr Thr Cys Ile Ile Trp Leu Ala
785                 790                 795                 800

Phe Val Pro Ile Tyr Phe Gly Ser Asn Tyr Lys Ile Ile Thr Thr Cys
                805                 810                 815

Phe Ala Val Ser Leu Ser Val Thr Val Ala Leu Gly Cys Met Phe Thr
                820                 825                 830

Pro Lys Met Tyr Ile Ile Ile Ala Lys Pro Glu Arg Asn Thr Ile Glu
        835                 840                 845

Glu Val Arg Cys Ser Thr Ala Ala His Ala Phe Lys Val Ala Ala Arg
850                 855                 860

Ala Thr Leu Arg Arg Ser Asn Val Ser Arg Lys Arg Ser Ser Ser Leu
865                 870                 875                 880

Gly Gly Ser Thr Gly Ser Thr Pro Ser Ser Ser Ile Ser Ser Lys Ser
                885                 890                 895

Asn Ser Glu Asp Pro Phe Pro Gln Pro Glu Arg Gln Lys Gln Gln Gln
            900                 905                 910

Pro Leu Ala Leu Thr Gln Gln Glu Gln Gln Gln Gln Pro Leu Thr Leu
        915                 920                 925

Pro Gln Gln Gln Arg Ser Gln Gln Gln Pro Arg Cys Lys Gln Lys Val
    930                 935                 940

Ile Phe Gly Ser Gly Thr Val Thr Phe Ser Leu Ser Phe Asp Glu Pro
945                 950                 955                 960

Gln Lys Asn Ala Met Ala His Gly Asn Ser Thr His Gln Asn Ser Leu
                965                 970                 975

Glu Ala Gln Lys Ser Ser Asp Thr Leu Thr Arg His Gln Pro Leu Leu
            980                 985                 990

Pro Leu Gln Cys Gly Glu Thr Asp Leu Asp Leu Thr Val Gln Glu Thr
        995                 1000                1005

Gly Leu Gln Gly Pro Val Gly Gly Asp Gln Arg Pro Glu Val Glu Asp
    1010                1015                1020

Pro Glu Glu Leu Ser Pro Ala Leu Val Val Ser Ser Ser Gln Ser Phe
1025                1030                1035                1040

Val Ile Ser Gly Gly Gly Ser Thr Val Thr Glu Asn Val Val Asn Ser
                1045                1050                1055
```